US008067668B2

(12) United States Patent
Kogel et al.

(10) Patent No.: US 8,067,668 B2
(45) Date of Patent: Nov. 29, 2011

(54) METHOD FOR OBTAINING THE PATHOGENIC RESISTANCE IN PLANTS

(75) Inventors: Karl-Heinz Kogel, Lollar (DE); Ralph Hückelhoven, Freising (DE); Marco Trujillo, Gieβen (DE)

(73) Assignee: BASF Plant Science GmbH, Ludwigshafen (DE)

( * ) Notice: Subject to any disclaimer, the term of this patent is extended or adjusted under 35 U.S.C. 154(b) by 906 days.

(21) Appl. No.: 10/522,106

(22) PCT Filed: Jul. 14, 2003

(86) PCT No.: PCT/EP03/07589
§ 371 (c)(1), (2), (4) Date: Jan. 24, 2005

(87) PCT Pub. No.: WO2004/009820
PCT Pub. Date: Jan. 29, 2004

(65) Prior Publication Data

US 2008/0047033 A1 Feb. 21, 2008

(30) Foreign Application Priority Data

Jul. 22, 2002 (DE) ................................. 10 233 327

(51) Int. Cl.
*A01H 1/00* (2006.01)
*A01H 5/00* (2006.01)
*C12N 15/09* (2006.01)
*C12N 15/82* (2006.01)
*C12N 15/29* (2006.01)

(52) U.S. Cl. ........ 800/279; 800/278; 800/298; 800/295; 800/320; 435/320.1; 435/468; 435/419; 536/23.6

(58) Field of Classification Search ........................ None
See application file for complete search history.

(56) References Cited

U.S. PATENT DOCUMENTS 6,506,559 B1 * 1/2003 Fire et al. .......................... 435/6

FOREIGN PATENT DOCUMENTS

WO WO-98/04586 2/1998
WO WO-99/47552 9/1999
WO WO 00/01722 1/2000

OTHER PUBLICATIONS

Schiene et al. Mol Gen Genet (2000) 263:761-770.*
Chuang et al. PNAS (2000) 97(9): 4985-4990).*
Wesley et al. Plant Journal (2001) 27(6), 581-590.*
S.J. et al. Plant Mol Biol. Jun. 1998;37(3):535-47).*
Guo et al. PNAS, 101: 9205-9210, 2004.*
Fourgoux-Nicol et al. Plant Molecular Biology (1999) 40: 857-872.*
Keskin et al. Protein Science (2004) 13:1043-1055.*
Torres, M., et al., "*Arabidopsis* gp91 *phox* homologues *AtrbohD* and *AtrbohF* are required for accumulation of reactive oxygen intermediates in the plant defense response", Proceedings of the National Academy of Sciences of the U.S., vol. 99, No. 1, Jan. 8, 2002, pp. 517-522.
Hückelhoven, R., et al., "Tissue-Specific Superoxide Generation at Interaction Sites in Resistant and Susceptible Near-Isogenic Barley Lines Attacked by the Powdery Mildew Fungus (*Erysiphe graminis f. sp. hordei*)", Molecular Plant-Microbe Interactions, vol. 11, No. 4, 1998, pp. 292-300.
Sagi, M., et al., "Superoxide Production by Plant Homologues of the gp91*phox* NADPH Oxidase. Modulation of Activity by Calcium and by Tobacco Mosaic Virus Infection", Plant Physiology, vol. 126, Jul. 2001, pp. 1281-1290.
Bolwell, G. Paul, et al., "The apoplastic oxidative burst in response to biotic stress in plants: a three-component system", Journal of Experimental Botany, vol. 53, No. 372, May 2002, pp. 1367-1376.
Hückelhoven, R., et al., "Functional Studies on the Role of Reactive Oxygen Intermediates in the Resistance of Barley against Powdery Mildew", Plant Protection Science, vol. 38, No. 2, 2002, pp. 458-460.
Borden, S., et al., "Hydrogen peroxide plays a critical role in the defence response of tomato to *Cladosporium fulvum*", Physiological and Molecular Plant Pathology, vol. 61, 2002, pp. 227-236.
Mahalingam, R., et al., "Stress response, cell death and signalling: the many faces of reactive oxygen species", Physiologia Plantarum, vol. 119, 2003, pp. 56-68.
Büschges, R., et al., "The Barley *Mlo* Gene: A Novel Control Element of Plant Pathogen Resistance", Cell, vol. 88, Mar. 7, 1997, pp. 695-705.
Jørgensen, J. Helms, "Spectrum of Resistance Conferred by *ML-O* Powdery Mildew Resistance Genes in Barley", Euphytica, vol. 26, 1977, pp. 55-62.
Lyngkjær, M.F., et al., "A Japanese powdery mildew isolate with exceptionally large infection efficiency on Mlo-resistant barley", Plant Pathology, vol. 44, 1995, pp. 786-790.
Schulze-Lefert, P., et al., "Closing the ranks to attack by powdery mildrew", Trends Plant Science, vol. 5, No. 8, Aug. 2000, pp. 343-348.
Wolter, M., et al., "The *mlo* resistance alleles to powdery mildew infection in barley trigger a developmentally controlled defence mimic phenotype", Mol. Gen. Genet., vol. 239, 1993, pp. 122-128.
Jarosch, B., et al., "The Ambivalence of the Barley *Mlo* Locus: Mutations Conferring Resistance Against Powdery Mildew (*Blumeria graminis* f. sp. *hordei*) Enchance Susceptibility to the Rice Blast Fungus *Magnaporthe grisea*", Molecular Plant-Microbe Interactions, vol. 12, No. 6, 1999, pp. 508-514.
Lamb, C., et al., "The Oxidative Burst in Plant Disease Resistance", Annu. Rev. Plant Physiol. Plant Mol. Biol., vol. 48, 1997, pp. 251-275.
Schweizer, P., et al., "Double-stranded RNA interferes with gene function at the single-cell level in cereals", The Plant Journal, vol. 24, No. 6, 2000, pp. 895-903.
Torres, M., et al., "Six *Arabidopsis thaliana* homologues of the human respiratory burst oxidase gp91$^{phox}$)", The Plant Journal, vol. 14, No. 3, 1998, pp. 365-370.
Yu L., et al., "Functional Analysis of NADPH Oxidase in Granulocytic Cells Expressing a Δ 488-497 gp91$^{phox}$ Deletion Mutant", Blood, vol. 94, No. 7, Oct. 1, 1999, pp. 2497-2504.

(Continued)

*Primary Examiner* — Medina A Ibrahim
(74) *Attorney, Agent, or Firm* — Connolly Bove Lodge & Hutz, LLP

(57) ABSTRACT

The invention relates to methods for generating or increasing a pathogen resistance in plants by reducing the expression, activity or function of an NADPH oxidase.

23 Claims, 1 Drawing Sheet

OTHER PUBLICATIONS

Doke, N., "Involvement of superoxide anion generation in the hypersensitive response of potato tuber tissues to infection with an incompatible race of *Phytophthora infestans* and to the hyphal wall components", Physiological Plant Pathology, 1983, vol. 23, pp. 345-357.
Levine, A., et al., "$H_2O_2$ from the Oxidative Burst Orchestrates the Plant Hypersensitive Disease Resistance Response", Cell, vol. 79, Nov. 18, 1994, pp. 583-593.
Tenhaken, R., et al., "Function of the oxidative burst in hypersensitive disease resistance", Proc. Natl. Acad. Sci., USA, vol. 92, May 1995, pp. 4158-4163.
Altschul, S., et al., "Gapped Blast and PSI-Blast: a new generation of protein database search programs", Nucleic Acids Research, vol. 25, No. 17, 1997, pp. 3389-3402.
Kølster, P., et al., "Near-Isogenic Barley Lines with Genes for Resistance to Powdery Mildew", Crop Science, vol. 26, Sep.-Oct. 1986, pp. 903-907.
Kumar, J., et al., "A Compromised Mlo Pathway Affects the Response of Barley to the Necrotrophic Fungus *Bipolaris sorokiniana* , (Teleomorph: *Cochliobolus sativus*) and Its Toxins", Phytopathology, vol. 91, No. 2, 2001, pp. 127-133.

* cited by examiner

METHOD FOR OBTAINING THE PATHOGENIC RESISTANCE IN PLANTS

RELATED APPLICATIONS

This application is a national stage application (under 35 U.S.C. §371) of PCT/EP2003/007589, filed Jul. 14, 2003, which claims benefit of German application 10233327.0, filed Jul. 22, 2002.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing__12810__00067. The size of the text file is 205 KB, and the text file was created on Dec. 15, 2009.

FIELD OF THE INVENTION

The invention relates to methods for generating or increasing a pathogen resistance in plants by reducing the expression, activity or function of an NADPH oxidase.

BACKGROUND OF THE INVENTION

The aim of plant biotechnology work is the generation of plants with advantageous novel properties, for example for increasing agricultural productivity. The plants' natural defense mechanisms against pathogens are frequently insufficient. Fungal diseases alone result in annual yield losses of many billions of US$. The introduction of foreign genes from plants, animals or microbial sources can increase the defenses. Examples are the protection against feeding damage by insects by expressing *Bacillus thuringiensis* endotoxins (Vaeck et al. (1987) Nature 328:33-37) or the protection against fungal infection by expressing a bean chitinase (Broglie et al. (1991) Science 254:1194-1197). However, most of the approaches described only offer resistance to a single pathogen or a narrow spectrum of pathogens.

Only a few approaches exist which impart a resistance to a broader spectrum of pathogens to plants. Systemic acquired resistance (SAR)—a defense mechanism in a variety of plant/pathogen interactions —can be conferred by the application of endogenous messenger substances such as jasmonic acid (JA) or salicylic acid (SA) (Ward, et al. (1991) Plant Cell 3:1085-1094; Uknes, et al. (1992) Plant Cell 4(6):645-656). Similar effects can also be achieved by synthetic compounds such as 2,6-dichloroisonicotinic acid (INA) or S-methyl benzo(1,2,3)thiadiazole-7-thiocarboxylate (BTH; Bion200 ) (Friedrich et al. (1996) Plant J 10(1) :61-70; Lawton et al. (1996) Plant J. 10:71-82). The expression of pathogenesis-related (PR) proteins, which are upregulated in the case of SAR, may also cause pathogen resistance in some cases.

In barley, the Mlo locus has been described as a negative regulator of the defense against pathogens. The loss of the Mlo gene causes an increased and, above all, race-unspecific resistance against a large number of mildew species (Büschges R et al. (1997) Cell 88:695-705; Jorgensen J H (1977) Euphytica 26:55-62; Lyngkjaer M F et al. (1995) Plant Pathol 44:786-790). Ml-deficient barley varieties obtained by conventional breeding are already being used in agriculture. Despite intensive cultivation, the resistance has proved to be durable, presumably due to the fact that it is recessive. Mlo-like resistances in other plants, in particular in cereal species, are not described. The Mlo gene and various homologs from other cereal species have been identified and cloned (Büschges R et al. (1997) Cell 88:695-705; WO 98/04586; Schulze-Lefert P, Vogel J (2000) Trends Plant Sci. 5:343-348). Various methods using these genes for obtaining a pathogen resistance are described (WO 98/04586; WO 00/01722; WO 99/47552). The disadvantage is that the Mlo-mediated defense mechanism comprises a spontaneous die-off of leaf cells (Wolter M et al. (1993) Mol Gen Genet 239:122-128). Another disadvantage is that the Mlo-deficient genotypes show hypersensitivity to hemibiotrophic pathogens such as *Magnaporte grisea* (*M. grisea*) and *Cochliobolus sativus* (*Bipolaris sorokiniana*) (Jarosch B et al. (1999) Mol Plant Microbe Interact 12:508-514; Kumar J et al. (2001) Phytopathology 91:127-133).

The liberation of reactive oxygen species (ROS; for example superoxide ($O_{2-}$) , hydroxyl radicals and $H_2O_2$) is ascribed an important protection function in the reaction on plant pathogens (Wojtaszek P (1997) Biochem J 322:681-692). A variety of ways of how a cell can produce ROS are known. In the macrophages of mammals, it is in particular the enzyme NADPH oxidase, which is able to transfer electrons to molecular oxygen, which must be mentioned. Homologous enzymes have also been identified in plants (Lamb & Dixon (1997) Annu Rev Plant Physiol Plant Mol Biol 48:251).

It has been shown that mutations in the catalytic subunit of NADPH oxidase in *Arabidopsis thaliana* show a reduced accumulation of reactive oxygen intermediates (ROI). With regard to the hypersensitive reaction (HR), the results were heterogeneous: while infection with the aviralulent and bactrium *Pseudomonas syringae* showed a reduced HR in a double mutant, the virulent oomycete *Peronospora parasitica* showed an increased HR. Growth—both of virulent and of avirulent P. syringae strains—was not changed in comparison with wild-type plants, however (Torres M A et al. (2002) Proc Natl Acad Sci USA 99:517-522). Likewise, the inhibition of NADPH oxidase by means of the inhibitor diphenyleneiodonium chloride (DPI)—at physiologically relevant concentrations—had no effect on the development of pathogenic fungi (Hückelhoven R & Kogel K H (1998) Mol Plant Microbe Interact 11:292-300). A cDNA fragment of a phagocytic barley NADPH oxidase (pNAox, homolog of the large subunit gp91phox of a phagocytic NADPH oxidase) is described under the GenBank Acc.-No.: AJ251717).

BRIEF SUMMARY OF THE INVENTION

The present invention aims at providing novel compounds for the defense against pathogens in plants, which compounds bring about an efficient defense against as broad as possible a pathogen spectrum in as many different plant species as possible, preferably the crop plants used in agriculture. We have found that this object is achieved by the present method.

DETAILED DESCRIPTION OF THE INVENTION

Figure 1:
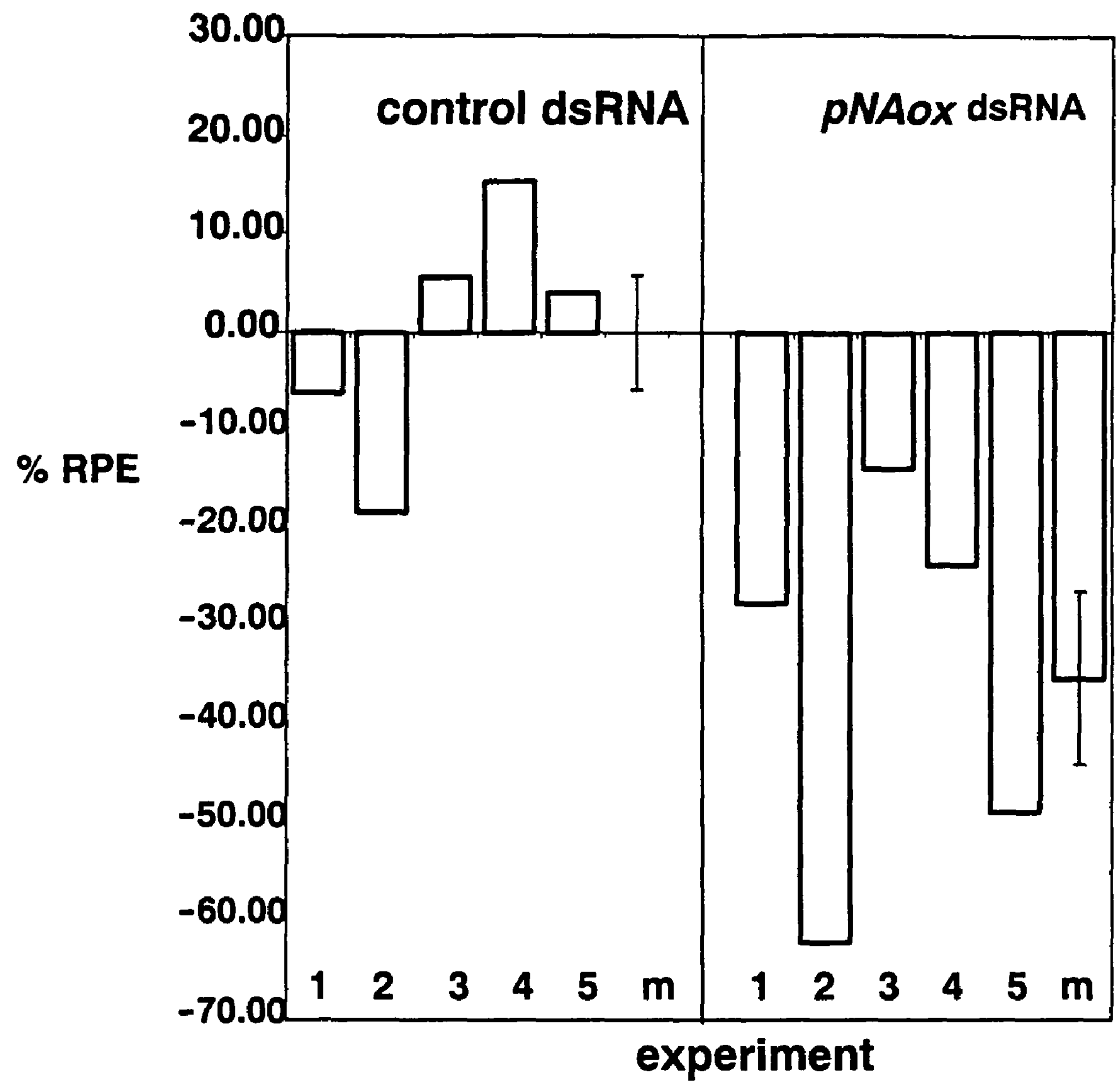
FIG. 1: RNA interference with pNAox-dsRNA reduces the penetration efficiency of powdery mildew of barley BghA6 in barley.

A first aspect of the invention comprises a method for generating or increasing the resistance to at least one pathogen in plants, which comprises the following operating steps:

a) reduction of the protein quantity, activity or function of an NADPH oxidase in a plant or a tissue, organ, part or cell thereof, and b) selection of the plants in which—in contrast or in comparison with the starting plant—the resistance to at least one pathogen exists or is increased.

Surprisingly, the reduction of the expression of a barley NADPH oxidase (pNAox) in the epidermal cell by a sequence-specific RNA interference approach using double-stranded pNAox-dsRNA ("gene silencing") shows a significantly reduced disease level following Bgh infection (measured with reference to the formulation of Haustoria). This finding is particularly surprising because the release of reactive oxygen species ("oxidative burst"), which is associated with NADPH oxidase, is generally ascribed a protective function.

Similar to Mlo, the reduction of the NADPH oxidase expression mediates a broad resistance to various isolates of *Blumeria graminis* f.sp. *hordei*. In transient gene silencing experiments, the penetration efficiency (development of Haustoria) of Bgh is reduced significantly by more than 35%—an effect which, in its intensity, corresponds to the effect obtained by means of Mlo-dsRNA (Schweizer P et al. (2000) Plant J 24:895-903). In the wild-type barley variety Pallas, approximately 40% of the fungal penetrations result in the development of haustoria, while the penetration rate in the case of reduced NADPH oxidase expression by introduction of a double-stranded RNA of NADPH oxidase (pNAox-dsRNA) only amounts to approximately 25%. The fact that even in pathogen-sensitive wild-type varieties such as Pallas only a penetration rate of approximately 40 to 50% can be observed can be attributed to the basal resistance, which is always present. Owing to these findings, the enzyme NADPH oxidase can be considered a key element for the successful penetration of a pathogen such as Bgh into the plant cell. In addition, the method is superior to all those methods where a pathogen-resistant phenotype is generated by overexpression of a resistance-mediating protein. Switching off a gene can be done without expression of a (foreign) protein. In the ideal case, only the endogenous gene is de-activated This has not inconsiderable advantages regarding approval and acceptance by the consumer, who is frequently unsure about plants with foreign proteins. Very especially advantageous in this context is the use of inducible promoters for reducing the NADPH oxidase quantity, activity or function, which, for example in the case of pathogen-inducible promoters, makes possible an expression only when required (i.e. attack by pathogens) In principle, the method according to the invention can be applied to all plant species, preferably to those in which an NADPH oxidase or a functional equivalent thereof is expressed naturally.

For the purposes of the invention, "plant" means all genera and species of higher and lower plants of the Plant Kingdom. Included in this expression are the mature plants, seed, shoots and seedlings, and parts, propagation material, plant organs, tissues, protoplasts, callus and other cultures, for example cell cultures, derived from them, and all other types of groups of plant cells which give functional or structural units. Mature plants refers to plants at any developmental stage beyond that of the seedling. Seedling means a young, immature plant in an early developmental stage. "Plant" comprises all annual and perennial monocotyledonous and dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

The term "plant" preferably comprises monocotyledonous crop plants, such as, for example, cereal species such as wheat, barley, millet, rye, triticale, maize, rice, sorghum or oats, and sugar cane.

The term furthermore comprises dicotyledonous crop plants such as, for example

Brassicaceae such as oilseed rape, canola, cress, *Arabidopsis, cabbages or canola, Leguminosae such as soybean, alfalfa, pea, beans or peanut*

Solanaceae such as potato, tobacco, tomato, egg plant or paprika, Asteraceae such as sunflower, Tagetes, lettice or Calendula, Cucurbitaceae such as melon, pumpkin/squash or zucchini, and linseed, cotton, hemp, clover, spinach, flax, red pepper, carrot, beet, radish, sugar beet, sweet potato, cucumber, chicory, cauliflower, broccoli, asparagus, onion, garlic, celeriac, strawberry, raspberry, blackberry, pineapple, avocado, and the various tree, bush, nut and vine species. Tree species preferably comprises plum, cherry, peach, nectarine, apricot, banana, paw paw, mango, apple, pear, quince.

Furthermore comprised are ornamental plants, useful or ornamental trees, flowers, cut flowers, shrubs or lawn, by way of example but not by way of limitation, the families of the Rosaceae such as rose, Ericaceae such as rhododendrons and azaleas, Euphorbiaceae such as poinsettias and croton, Caryophyllaceae such as carnations, Solanaceae such as petunias, Gesneriaceae such as African violets, Balsaminaceae such as touch-me-not, Orchidaceae such as orchids, Iridaceae such as gladioli, iris, freesia and crocus, Compositae such as calendula, Geraniaceae such as geraniums, Liliaceae such as dracaena, Moraceae such as ficus, Araceae such as philodendron, and many others.

Preferred for the purposes of the invention are those plants which are employed as food or feedstuff, very especially preferably monocotyledonous genera and species, such as the above-described cereal species.

The method is very especially preferably applied to monocotyledonous plants, most preferably to plants with agricultural importance such as wheat, oats, millet, barley, rye, maize, rice, buckwheat, sorghum, triticale, spelt, linseed or sugar cane.

"Pathogen resistance" denotes the reduction or weakening of disease symptoms of a plant following infection by a pathogen. The symptoms can be manifold, but preferably comprise those which directly or indirectly have an adverse effect on the quality of the plant, the quantity of the yield, the suitability for use as feedstuff or foodstuff, or else which make sowing, planting, harvesting or processing of the crop difficult.

"Conferring", "existing", "generating" or "increasing" a pathogen resistance means that the defense mechanisms of a specific plant species or variety is increasingly resistant to one or more pathogens due to the use of the method according to the invention in comparison with the wild type of the plant ("original plant"), to which the method according to the invention has not been applied, under otherwise identical conditions (such as, for example, climatic conditions, growing conditions, pathogen species and the like). The increased resistance manifests itself preferably in a reduced manifestation of the disease symptoms, disease symptoms comprising—in addition to the abovementioned adverse effects—for example also the penetration efficiency of a pathogen into the plant or plant cells or the proliferation efficiency in or on the same. In this context, the disease symptoms are preferably reduced by at least 10% or at least 20%, especially preferably by at least 40% or 60%, very especially preferably by at least 70% or 80% and most preferably by at least 90% or 95%.

"Selections" with regard to plants in which—as opposed or as compared to the original plant—resistance to at least one pathogen exists or is increased means all those methods which are suitable for recognizing an existing or increased resistance to pathogens. These may be symptoms of pathogen infection (for example the development of haustoria in the case of fungal infection), but may also comprise the above-described symptoms which relate to the quality of the plant, the quantity of the yield, the suitability for use as feedstuff or foodstuff and the like.

"Pathogen" within the scope of the invention means by way of example but not by limitation viruses or viroids, bacteria, fungi, animal pests such as, for example, insects or nematodes. Especially preferred are fungi, such as mildew. However, it can be assumed that the expression of an NADPH oxidase, its activity or its function also brings about resistance to other pathogens. The following pathogens may be mentioned by way of example but not by limitation:

1. Fungal Pathogens and Fungus-like Pathogens:

Fungal pathogens and fungus-like pathogens (such as, for example, Chromista) are preferably from the group comprising Plasmodiophoramycota, Oomycota, Ascomycota, Chytridiomycetes, Zygomycetes, Basidiomycota and Deuteromycetes (Fungi imperfecti). The pathogens mentioned in Tables 1 and 2 and the diseases with which they are associated may be mentioned by way of example but not by limitation.

TABLE 1

| Fungal plant diseases | |
|---|---|
| Disease | Pathogen |
| Leaf ruse | *Puccinia recondita* |
| Yellow rust | *P. striiformis* |
| Powdery mildew | *Erysiphe graminis/Blumeria graminis* |
| Glume blotch | *Septoria nodorum* |
| Leaf blotch | *Septoria tritici* |
| Ear fusarioses | *Fusarium* spp. |
| Eyespot | *Pseudocercosporella herpotrichoides* |
| Smut | *Ustilago* spp. |
| Bunt | *Tilletia caries* |
| Take-all | *Gaeumannomyces graminis* |
| Anthrocnose leaf blight | *Colletotrichum graminicola* (teleomorph: |
| Anthracnose stalk rot | *Glomerella graminicola Politis*); *Glomerella tucumanensis* (anamorph: *Glomerella falcatum* Went) |
| Aspergillus ear and kernel rot | *Aspergillus flavus* |
| Banded leaf and sheath spot | *Rhizoctonia solani* Kuhn = *Rhizoctonia microsclerotia* J. Matz (telomorph: *Thanatephorus cucumeris*) |
| Black bundle disease | *Acremonium strictum* W. Gams = *Cephalosporium acremonium* Auct. non Corda |
| Black kernel rot | *Lasiodiplodia theobromae= Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium ear rot* | *Thanatephorus cucumeris* = *Corticium sasakii* |
| *Curvularia* leaf spot | *Curvularia clavata*, *C. eragrostidis* = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodia* leaf *macrospora* |

TABLE 2

| Downy mildew | |
|---|---|
| Disease | Pathogen |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |

TABLE 2-continued

| Downy mildew | |
|---|---|
| Disease | Pathogen |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii* |
| Ergot (horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria pedicellata*) |
| *Hormodendrum* ear rot (*Cladosporium* rot) | *Cladosporium cladosporioides* = *Hormodendrum cladosporioides*, *C. herbarum* (teleomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides,* *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris* zeicola = *Helminthosporium carbonum*) |
| *Penicillium ear rot* (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk rot and root rot | *Phoma terrestris* = *Pyrenochaeta terrestris* |

TABLE 2-continued

| Downy mildew | |
|---|---|
| Disease | Pathogen |
| *Pythium* root rot | *Pythium* spp., *P. arrhenomanes*, *P. graminicola* |
| *Pythium* stalk rot | *Pythium aphanidermatum* = *P. butleri L.* |
| Red kernel disease (ear mold, leaf and seed rot) | *Epicoccum nigrum* |
| *Rhizoctonia* ear rot (sclerotial rot) | *Rhizoctonia zeae* (teleomorph: *Waitea circinata*) |
| *Rhizoctonia* root rot and stalk rot | *Rhizoctonia solani*, *Rhizoctonia zeae* |
| Root rots, minor | *Alternaria alternata, Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (*Helminthosporium* leaf disease, ear and stalk rot) | *Setosphaeria rostrata*, (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M ruber* |
| Smut, common | *Ustilago zeae* = *U. maydis* |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi, Fusarium episphaeria, F. merismoides*, *F. oxysporum* Schlechtend, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |
| Tar spot | *Phyllachora maydis* |
| *Trichoderma* ear rot and root rot | *Trichoderma viride* = *T. lignorum* teleomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred

Plasmodiophoromycota such as *Plasmodiophora brassicae* (clubroot of crucifers), *Spongospora subterranea* (powdery scab of potato tubers), *Polymyxa graminis* (root disease of cereals and grasses), Oomycota such as *Bremia lactucae* (downy mildew of lettuce), *Peronospora* (downy mildew) in snapdragon (*P. antirrhini*), onion (*P. destructor*), spinach (*P. effuse*), soybean (*P. manchurica*), tobacco ("blue mold"; *P. tabacina*), alfalfa and clover (*P. Trifolium*), *Pseudoperonospora humuli* (downy mildew of hops), *Plasmopara* (downy mildew in grapevines) (*P. Viticola*) and sunflower (*P. halstedii*), *Sclerophtohra macrospora* (downy mildew in cereals and grasses), *Pythium* (seed rot, seedling damping-off, and root rot of all types of plants, for example damping-off of Beta beet caused by *P. debaryanum*), *Phytophthora infestans* (blight in potato, brown rot in tomato and the like), *Albugo* spec. (white rust on cruciferous plants).

Ascomycota such as *Microdochium nivale* (snow mold of rye and wheat), *Fusarium graminearum, Fusarium culmorum* (partial ear sterility mainly in wheat), *Fusarium oxysporum* (*Fusarium wilt* of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria canker* of fruit trees), *Uncinula necator* (powdery mildew of grapevine), *Pseudopeziza tracheiphila* (red fire disease of grapevine), Claviceps purpurea (ergot on, for example, rye and grasses), *Gaeumannomyces graminis* (take-all on wheat, rye and other grasses), *Magnaporthe grisea* (rice blast disease), *Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (typhula blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium wilt*), *Colletotrichum lindemuthianum* (bean anthracnose), *Phoma lingam* (blackleg of cabbage and oilseed rape), *Botrytis cinerea* (gray mold of grapevine, strawberry, tomato, hops and the like).

Most preferred are *Phytophthora infestans* (potato blight, brown rot in tomato and the like), *Microdochium nivale* (previously *Fusarium nivale*; snow mold of rye and wheat), *Fusarium graminearum, Fusarium culmorum* (partial ear sterility of wheat), *Fusarium oxysporum (Fusarium wilt* of tomato), *Blumeria graminis* (powdery mildew of barley (f. sp. *hordei*) and wheat (f. sp. *tritici*)), *Magnaporthe grisea* (rice blast disease), *Sclerotinia sclerotium* (stalk break, stem rot), *Septoria nodorum* and *Septoria tritici* (glume blotch of wheat), *Alternaria brassicae* (black spot of oilseed rape, cabbage and other crucifers), *Phoma lingam* (blackleg of cabbage and oilseed rape).

2. Bacterial Pathogens:

The pathogens and diseases associated with them, all of which are mentioned in table 3, may be mentioned by way of example, but not by limitation.

TABLE 3

| Bacterial diseases | |
|---|---|
| Disease | Pathogen |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | Enterobacter dissolvens = *Erwinia dissolvens* |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv. *nebraskense* |
| Holcus spot | *Pseudomonas syringae* pv. *syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

Very especially preferred are the following pathogenic bacteria: *Corynebacterium sepedonicum* (potato bacterial ring rot), *Erwinia carotovora* (potato bacterial soft rot), *Erwinia amylovora* (fire blight on pear, apple, quince), *Streptomyces scabies* (potato scab), *Pseudomonas syringae* pv. *tabaci* (tobacco black fire), *Pseudomonas syringae* pv. *phaseolicola* (bean grease spot), *Pseudomonas syringae* pv. *tomato* (*tomato* bacterial speck), *Xanthomonas campestris* pv. *malvacearum* (cotton bacterial blight) and *Xanthomonas campestris* pv. *oryzae* (bacterial leaf blight on rice and other grasses).

3. Viral Pathogens:

"Viral pathogens" includes all plant viruses such as, for example, tobacco or cucumber mosaic virus, ringspot virus, necroses virus, maize dwarf mosaic virus and the like.

Pathogens and the diseases associated with them may be mentioned in table 4 by way of example, but not by limitation.

TABLE 4

| Viral diseases | |
|---|---|
| Disease | Pathogen |
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |

TABLE 4-continued

| Viral diseases | |
|---|---|
| Disease | Pathogen |
| Corn chlorotic vein banding (Braizilian maize mosaic) | Corn chlorotic vein banding virus (CCVBV) |
| Corn lethal necrosis | Virus complex of Maize chlorotic mottle virus (MCMV) and Maize dwarf mosaic virus (MDMV) A or B or Wheat streak mosaic virus(WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| maize rayado fino (fine striping disease) | Maize rayado fino virus (MRFV) |
| Maize red leaf and red stripe | Mollicute |
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |
| Maize sterile stunt | Maize sterile stunt virus (strains of barley yellow striate virus) |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (also: sugarcane mosaic virus (SCMV) strains H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

4. Animal Pests 4.1 Insect pathogens:

Insects such as, for example, beetles, caterpillars, lice or mites may be mentioned by way of example, but not by limitation. Preferred are insects of the genera *Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera*, and the like. Especially preferred are *Coleoptera* and *Lepidoptera* insects such as, for example, the European corn borer (ECB), *Diabrotica barberi* ("northern corn rootworm"), *Diabrotica undecimpunctata* ("southern corn rootworm"), *Diabrotica virgifera* ("Western corn rootworm"), *Agrotis ipsilon* ("black cutworm", *Crymodes devastator* ("glassy cutworm"), *Feltia ducens* ("dingy cutworm"), *Agrotis gladiaria* ("claybacked cutworm"), *Melanotus* spp., *Aeolus mellillus* ("wireworm"), *Aeolus mancus* ("wheat wireworm"), *Horistonotus uhlerii* ("sand wireworm"), *Sphenophorus maidis* ("maize billbug"), *Sphenophorus zeae* ("timothy billbug"), *Sphenophorus parvulus* ("bluegrass billbug"), *Sphenophorus callosus* ("southern corn billbug"), *Phyllogphaga* spp. ("white grubs"), *Anuraphis maidiradicis* ("corn root aphid"), *Delia platura* ("seedcorn maggot"), *Colaspis brunnea* ("grape colaspis"), *Stenolophus lecontei* ("seedcorn beetle") and *Clivinia impressifrons* ("lender seedcorn beetle").

Others which may be mentioned are: the cereal leaf beetle (*Oulema melanopus*), the frit fly (*Oscinella frit*), wireworms (*Agrotis lineatus*) and aphids (such as, for example, the oat grain aphid *Rhopalosiphum padi*, the blackberry aphid *Sitobion avenae*).

4.2 Nematodes:

Pathogens and the diseases associated with them may be mentioned by way of example, but not by way of limitation, in table 6.

TABLE 6

| Parasitic nematodes | |
|---|---|
| Disease | Pathogenic Nematode |
| Awl | *Dolichodorus* spp., *D. heterocephalus* |
| Bulb and stem nematode disease; Europe | *Ditylenchus dipsaci* |
| Burrowing | *Radopholus similis* |
| Cyst nematode disease | *Heterodera avenae*, *H. zeae*, *Punctodera chalcoensis* |
| Dagger | *Xiphinema* spp., *X. americanum X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus*, *P. crenatus*, *P. hexincisus*, *P. neglectus*, *P. penetrans*, *P. scribneri*, *P. thornei*, *P. zeae* |
| Needle | *Longidorus* spp., *L. breviannulatus* |
| Ring | *Criconemella* spp., *C. ornata* |
| Root-knot disease | *Meloidogyne* spp., *M. chitwoodi*, *M. incognita*, *M. javanica* |
| Spiral | *Helicotylenchus* spp. |
| Sting | *Belonolaimus* spp., *B. longicaudatus* |
| Stubby-root | *Paratrichodorus* spp., *P. christiei*, *P. minor*, *Quinisulcius acutus*, *Trichodorus* spp. |
| Stunt | *Tylenchorhynchus dubius* |

Very especially preferred are *Globodera rostochiensis* and *G. pallida* (cyst eelworm on potato, tomato and other Solanaceae), *Heterodera schachtii* (beet eelworm on sugar and fodder beet, oilseed rape, cabbage and the like), *Heterodera avenae* (cereal cyst nematode on oat and other cereal species), *Ditylenchus dipsaci* (stem or bulb eelworm, stem eelworm of rye, oats, maize, clover, tobacco, beet), *Anguina tritici* (earcockle nematode, cockle disease of wheat (spelt, rye), *Meloidogyne hapla* (root-knot nematode of carrot, cucumber, lettuce, tomato, potato, sugar beet, alfalfa).

Examples of fungal or viral pathogens which are preferred for the individual varieties are the following:

1. Barley:

fungal, bacterial and viral pathogens: *Puccinia graminis* f.sp. *hordei* (barley stem rust), *Blumeria* (*Erysiphe*)

*graminis* f.sp. *hordei* (Barley Powdery Mildew), barley yellow dwarf virus (BYDV), Pathogenic insects/nematodes: *Ostrinia nubilalis* (European corn borer); *Agrotis ipsilon* (black cutworm); *Schizaphis gramineum* (greenbug); *Blissus leucopterus leucopterus* (chinch bug); *Acrosternum hilare* (green stink bug); *Euschistus servus* (brown stink bug); *Delia platura* (seedcorn maggot); *Mayetiola destructor* (*Hessian fly*); *Petrobia latens* (brown wheat mite).

2. Soybean:

Fungal, bacterial or viral pathogens: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manchurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffussa, Fusarium semitectum, Phialophora gregata*, Soybean mosaic virus, *Glomerella glycines*, Tobacco Ring spot virus, Tobacco Streak virus, *Phakopsora-pachyrhizi, Pythium aphanidermatum, Pythium ultimum, Pythium Debaryanum*, Tomato spotted wilt virus, *Heterodera glycines, Fusarium solani.*

Pathogenic insects/nematodes: Pseudoplusia includens (soybean looper); *Anticarsia gemmatalis* (velvetbean caterpillar);

*Plathypena scabra* (green cloverworm); *Ostrinia nubilalis* (European corn borer); *Agrotis ipsilon* (black cutworm); *Spodoptera exigua* (beet armyworm); *Heliothis virescens* (cotton budworm); *Helicoverpa zea* (cotton bollworm); *Epilachna varivestis* (Mexican bean beetle); *Myzus persicae* (green peach aphid); *Empoasca fabae* (potato leaf hopper); *Acrosternum hilare* (green stink bug); *Melanoplus femurrubrum* (redlegged grasshopper); *Melanoplus differentialis* (differential grasshopper); *Hylemya platura* (seedcorn maggot); *Sericothrips variabilis* (soybean thrips); *Thrips tabaci* (onion thrips); *Tetranychus turkestani* (strawberry spider mite); *Tetranychus urticae* (two-spotted spider mite).

3. Canola:

Fungal, bacterial or viral pathogens: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata.*

4. Alfalfa:

Fungal, bacterial or viral pathogens: *Clavibacter michiganense* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae.*

5. Wheat:

Fungal, bacterial or viral pathogens: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil-Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus, *Puccinia graminis* f.sp. *tritici* (Wheat stem rust), *Blumeria* (*Erysiphe*) *graminis* f.sp. *tritici* (Wheat Powdery Mildew)

Pathogenic insects/nematodes: *Pseudaletia unipunctata* (army worm); *Spodoptera frugiperda* (fall armyworm); *Elasmopalpus lignosellus* (lesser cornstalk borer); *Agrotis orthogonia* (western cutworm); *Elasmopalpus Zignosellus* (lesser cornstalk borer); *Oulema melanopus* (cereal leaf beetle); *Hypera punctata* (clover leaf weevil); *Diabrotica undecimpunctata howardi* (southern corn rootworm); Russian wheat aphid; *Schizaphis graminum* (greenbug); *Macrosiphum avenae* (English grain aphid); *Melanoplus femurrubrum* (redlegged grasshopper); *Melanoplus differentialis* (differential grasshopper); *Melanoplus sanguinipes* (migratory grasshopper); *Mayetiola destructor* (Hessian fly); *Sitodiplosis mosellana* (wheat midge); *Meromyza americana* (wheat stem maggot); *Hylemya coarctata* (wheat bulb fly); *Frankliniella fusca* (tobacco thrips); *Cephus cinctus* (wheat stem sawfly); *Aceria tulipae* (wheat curl mite).

6. Sunflower:

Fungal, bacterial or viral pathogens: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis.*

Pathogenic insects/nematodes: *Suleima helianthana* (sunflower bud moth); *Homoeosoma electellum* (sunflower moth); *zygogramma exclamationis* (sunflower beetle); *Bothyrus gibbosus* (carrot beetle); *Neolasioptera murtfeldtiana* (sunflower seed midge).

7. Maize:

Fungal, bacterial or viral pathogens: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* 0, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum,*

*Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* p.v. *Zea, Erwinia corotovora, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zeae, Cephalosporium maydis, Caphalosporium acremonium*, Maize Chlorotic Mottle Virus, High Plains Virus, Maize Mosaic Virus, Maize Rayado Fino Virus, Maize Streak Virus (MSV), Maize Stripe Virus, Maize Rough Dwarf Virus.

Pathogenic insects/nematodes: *Ostrinia nubilalis* (European corn borer); *Agrotis ipsilon* (black cutworm); *Helicoverpa zea* (corn earworm); *Spodoptera frugiperda* (fall armyworm); *Diatraea grandiosella* (southwestern corn borer); *Elasmopalpus lignosellus* (lesser cornstalk borer); *Diatraea saccharalis* (surgarcane borer); *Diabrotica virgifera* (western corn rootworm); *Diabrotica longicornis barberi* (northern corn rootworm); *Diabrotica undecimpunctata howardi* (southern corn rootworm); *Melanotus* spp. (wireworms); *Cyclocephala borealis* (northern masked chafer; white grub); *Cyclocephala immaculata* (southern masked chafer; white grub); *Popillia japonica* (Japanese beetle); *Chaetocnema pulicaria* (corn flea beetle); *Sphenophorus maidis* (maize billbug); *Rhopalosiphum maidis* (corn leaf aphid); *Anuraphis maidiradicis* (corn root aphid); *Blissus leucopterus leucopterus* (chinch bug); *Melanoplus femurrubrum* (redlegged grasshopper); *Melanoplus sanguinipes* (migratory grasshopper); *Hylemva platura* (seedcorn maggot); *Agromyza parvicornis* (corn blot leafminer); *Anaphothrips obscrurus* (grass thrips); *Solenopsis milesta* (thief ant); *Tetranychus urticae* (twospotted spider mite).

8. Sorghum:

Fungal, bacterial or viral pathogens: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi, Sugarcane mosaic* H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola.*

Pathogenic insects/nematodes: *Chilo partellus* (sorghum borer); *Spodoptera frugiperda* (fall armyworm); *Helicoverpa zea* (corn earworm); *Elasmopalpus lignosellus* (lesser cornstalk borer); *Feltia subterranea* (granulate cutworm); *Phyllophaga crinita* (white grub); *Eleodes, Conoderus* and *Aeolus* spp. (wireworm); *Oulema melanopus* (cereal leaf beetle); *Chaetocnema pulicaria* (corn flea beetle); *Sphenophorus maidis* (maize billbug); *Rhopalosiphum maidis* (corn leaf aphid); *Siphaflava* (yellow sugarcane aphid); *Blissus leucopterus leucopterus* (chinch bug); *Contarinia sorghicola* (sorghum midge); *Tetranychus cinnabarinus* (carmine spider mite); *Tetranychus urticae* (two-spotted spider mite).

9. Cotton:

Pathogenic insects/nematodes: *Heliothis virescens* (cotton budworm); *Helicoverpa zea* (cotton bollworm); *Spodoptera exigua* (beet armyworm); *Pectinophora gossypiella* (pink bollworm); *Anthonomus grandis grandis* (boll weevil); *Aphis gossypii* (cotton aphid); *Pseudatomoscelis seriatus* (cotton fleahopper); *Trialeurodes abutilonea* (bandedwinged whitefly); *Lygus lineolaris* (tarnished plant bug); *Melanoplus femurrubrum* (redlegged grasshopper); *Melanoplus differentialis* (differential grasshopper); *Thrips tabaci* (onion thrips); *Franklinkiella fusca* (tobacco thrips); *Tetranychus cinnabarinus* (carmine spider mite); *Tetranychus urticae* (twospotted spider mite).

10. Rice:

Pathogenic insects/nematodes: *Diatraea saccharalis* (sugar-cane borer); *Spodoptera frugiperda* (fall armyworm); *Helicoverpa zea* (corn earworm); *Colaspis brunnea* (grape colaspis); *Lissorhoptrus oryzophilus* (rice water weevil); *Sitophilus oryzae* (rice weevil); *Nephotettix nigropictus* (rice leafhopper); *Blissus leucopterus leucopterus* (chinch bug); *Acrosternum hilare* (green stink bug).

11. Oilseed Rape:

Pathogenic insects/nematodes: *Brevicoryne brassicae* (cabbage aphid); *Phyilotreta cruciferae* (Flea beetle); *Mamestra conjugrata* (Bertha armyworm); *Plutella xylostella* (Diamondback moth); *Delia* ssp. (Root maggots).

For the purposes of the invention, "NADPH oxidase" means all those enzymes whose essential characteristic is that they are capable, by means of a single electron transfer, of converting molecular oxygen ($O_2$) into superoxide ($O_{2-}$). Preferred are those enzymes which are described by the EC class E.C.1.23.45.3. In this context, the NADPH oxidases can consist of one or more polypeptides which may be identical or different.

Preferably, the NADPH oxidase is a flavocytochrome protein and comprises, as prosthetic groups, a cytochrome b and/or an FAD unit. The NADPH oxidase may consist of an $\alpha1\beta1$ heterodimer, the $\beta$ subunit being the functional subunit of the flavocytochrome, which may comprise, as glycoprotein, the electron transport components (a hydrophilic, cytosolic, C-terminal domain, comprising NADPH and FAD, and 4 to 6 N-terminal, putative transmembrane $\alpha$-helices, comprising two histidine-complexed prosthetic heme groups). The $\alpha$-subunit may comprise a C-terminal, prolin-rich sequence which is capable of binding potential cytosolic, activating factors of the NADPH oxidase. Activation may take place by binding the cytosolic phox proteins (for example p47-phox, p67-phox, p40-phox) and p21rac, a GTP-binding protein.

The skilled worker is familiar with a large number of NADPH oxidases from plant organisms (Torres M A et al. (1998) Plant J 14:365-370, inter alia). Sequences which may be mentioned by way of example, but not by limitation, are those with the following GenBank Acc. Nos.: AJ251717 (*Hordeum vulgare*), AP003560 (*Oryza sativa* var. *japonica*), AJ320505 (*Nicotiana tabacum*), AB050660 (*Solanum Tuberosum*), AF088276 (*Lycopersicon esculentum*), AB008111 (*Arabidopsis thaliana*; Atrboh F), AF055357

(*Arabidopsis thaliana*; RbohD), AJ309006 (*Nicotiana tabacum*; rboh), AP003271 (*Oryza sativa* cv. *japonica*), AF055355 (*Arabidopsis thaliana*; RbohC), AF055353 (*Arabidopsis thaliana*; RbohA). Especially preferred are the NADPH oxidases which comprise a sequence as shown in SEQ ID: 2, 4, 6, 8, 10, 12, 14, 16, 18, 20 or 22.

The sequences from other plants which are homologous to the NADPH oxidase sequences disclosed within the present invention can be found readily for example by database search or by screening genetic libraries using the NADPH oxidase sequences as search sequence or probe. Examples which may be mentioned are sequences with the following GenBank Acc. Nos.: CAC51517.1, AJ251717, T03973, BAB68079.1, AP003560, T02024, CAC87256.1, AJ320505, BAB70750.1, AB050660, AF088276__1, NP__564821.1, NM__105079, T00265 AC007764__16, NP__192862.1, NM__117194, AF147783__1, AAM28891.1, AF506374, CAC84140.1, AJ309006, T51804, NP__199602.1, NM__124165, BAB89740.1, AP003271, AAC39477.1, AF055355, NP__199919.1, NM__124485, AAC39475.1, AF055353, NP__196356.1, NM__120821, NP__194239.1, NM__118641, BAB08369.1, AB015475, AAC39478.1, AF055356, AC069143__9, NP__173357.1, NM__101781, NP__172383.1, NM__100780, AAB70398.1, AC000106, AAC39476.1, AF055354, BAB70751.1, AB050661, BAB63664.1, AP003275, AAD24966.1, AF109150.

The polypeptide sequence of the NADPH oxidase especially preferably comprises at least one sequence motif selected from the group of sequence motifs consisting of i) AL(K/R)GL(K/R)
ii) DK(N/D)XDG(R/K)(I/L/V)(T/N)E
iii) LSASAN
iv) IIVIEELDP
v) K(F/L)NMA(I/L)(I/V)LXPVCRN
vi) (E/Q)WHPFSIT
vii) S(A/S)PXDD(Q/Y)(L/I)S(I/V)H(V/I/L)R
viii) DGPYG(S/A)PAGDY
ix) L(N)GLGIGATP
x) FYWVTREQGSF
xi) GVFYCG The peptide sequence very especially preferably comprises at least 2 or 3, very especially preferably at least 4 or 5, most preferably all of the sequence motifs selected from the group of the sequence motifs i), ii), iii), iv), v), vi), vii), viii), ix) x) and xi). (Letters in brackets mean alternative amino acids which are possible at this position, for example (V/I) means that valine or isoleucine are possible at this position).

NADPH oxidase may also mean any other unit of an NADPH oxidase enzyme complex which is essential for activity of the NADPH oxidase.

"Protein quantity" means the amount of a NADPH oxidase polypeptide in an organism, a tissue, a cell or a cell compartment. "Reduction" of the protein quantity means the quantitative reduction of the amount of an NADPH oxidase in an organism, a tissue, a cell or a cell compartment—for example by one of the methods described hereinbelow—in comparison with the wild-type of the same genus and species to which this method has not been applied, under otherwise identical conditions (such as, for example, culture conditions, age of the plants and the like). In this context, the reduction amounts to at least 10%, preferably at least 10% or at least 20%, especially preferably by at least 40% or 60%, very especially preferably by at least 70% or 80%, most preferably by at least 90% or 95%.

"Activity" means the ability of an NADPH oxidase of converting molecular oxygen ($O_2$) into superoxide ($O_{2}$_). "Reduction" of the activity means the reduction of the total activity of an NADPH oxidase protein in an organism, a tissue, a cell or a cell compartment—for example by one of the methods described hereinbelow —in comparison with the wild type of the same genus and species, to which this method has not been applied, under otherwise identical conditions (such as, for example, culture conditions, age of the plants and the like). In this context, the reduction amounts to at least 10%, preferably at least 10% or at least 20%, especially preferably to at least 40% or 60%, very especially preferably to at least 70% or 80%, most preferably to at least 90% or 95%.

"Function" preferably means the substrate binding capacity of an NADPH oxidase in an organism, a tissue, a cell or a cell compartment. Suitable substrates are low-molecular-weight compounds such as NADPH or FAD, but also the protein interaction partners of an NADPH oxidase.

"Reduction" of the function means, for example, the quantitative reduction of the binding capacity or binding strength of an NADPH oxidase for at least one substrate in an organism, a tissue, a cell or a cell compartment—for example by one of the methods described hereinbelow—in comparison with the wild-type of the same genus and species to which this method has not been applied, under otherwise identical conditions (such as, for example, culture conditions, age of the plants and the like). "Reduction" is also understood as meaning the change in substrate specificity as expressed, for example, by the kcat/Km value. In this context, the reduction amounts to at least 10%, preferably at least 10% or at least 20%, especially preferably to at least 40% or 60%, very especially preferably to at least 70% or 80%, most preferably to at least 90% or 95%. Binding partners for NADPH oxidase can be identified for example by the yeast-2-hybrid system in the manner with which the skilled worker is familiar.

Methods for determining the protein quantity, the activity of NADPH oxidases or the substrate binding capacity are known to the skilled worker. For example, it is possible to measure the NADPH-dependent $O_{2}$_ or $H_2O_2$ production which can be inhibited by DPI (for example via Nitro Blue Tetrazolium [NBT] or cytochrome c reduction). The protein quantity can be determined for example immunologically, using suitable antibodies. Suitable methods are described (Yu L et al. (1999) Blood 94(7):2497-504; Doke N (1983a) Physiol Plant Pathol 23:345-357; Levine A et al. (1994) Cell 79:583-593; Tenhaken R et al. (1995) Proc Nat Acad Sci USA 92: 4158-4163; Sagi M & Fluhr R. (2001) Plant Physiol 126(3):1281-90; Hückelhoven R & Kogel K H (1998) Mol Plant Microbe Interact 11:292-300; and references cited in the above papers).

"Functional equivalents" of an NADPH oxidase protein preferably means those sequences which are derived from an NADPH oxidase comprising a polypeptide sequence as shown in SEQ ID NO: 2, 4, 6, 8, 10, 12, 14, 16, 18, 20 or 22 or which are homologous with the former and which have the same essential characteristics.

In this context, the efficiency of the pathogen resistance may deviate both upwards and downwards in comparison with a value obtained when reducing one of the NADPH oxidases comprising a polypeptide sequence as shown in SEQ ID NO: 2, 4, 6, 8, 10, 12, 14, 25 16, 18, 20 or 22. Preferred functional equivalents are those where the efficiency of the pathogen resistance—measured for example with the aid of the penetration efficiency of a pathogen (development of haustora)—differs by not more than 50%, preferably 25%, especially preferably 10%, from a comparative value obtained by reducing an NADPH oxidase comprising a polypeptide sequence as described in SEQ ID NO: 2, 4, 6, 8, 10, 12, 14, 16, 18, 20 or 22. Especially preferred are those sequences whose reduction has the result that the efficiency of the pathogen resistance quantitatively exceeds a comparative value obtained by reducing one of the NAPDH oxidases comprising a polypeptide sequence as shown in SEQ ID NO: 2, 4, 6, 8, 10, 12, 14, 16, 18, 20 or 22 by more than 50%, preferably 100%, especially preferably 500%, very especially preferably 1000%.

The comparison is preferably carried out under analogous conditions. "Analogous conditions" means that all framework conditions such as, for example, culture or growth conditions, assay conditions (such as buffer, temperature, substrates, pathogen concentration and the like) between the experiments to be compared are kept identical and that the set-ups differ only by the sequence of the NAPDH oxidases to be compared, their organism of origin and, if appropriate, the pathogen. When selecting the pathogen for the comparison, the pathogen to be selected for the comparison is that which is most similar to the corresponding other pathogen, taking into consideration the species specificity.

In particular, "functional equivalents" means natural or artificial mutations of the NADPH oxidases comprising a polypeptide sequence as shown in SEQ ID NO: 2, 4, 6, 8, 10, 12, 14, 16, 18, 20 or 22 and homologous polypeptides from other plants which continue to have essentially identical characteristics. Homologous polypeptides from the above-described preferred plants are preferred. The sequences from other plants (for example *Arabidopsis Thaliana*) which are homologous to the NAPDH oxidase sequences disclosed within the scope of the present invention can be found readily for example by database search or screening genetic libraries, using the NADPH oxidase sequences as search sequence or probe. Such sequences are detailed above by way of example together with their GenBank Acc No.

Mutations comprise substitutions, additions, deletions, inversions or insertions of one or more amino acid residues. Thus, the present invention also comprises for example those polypeptides which are obtained by modification of a polypeptide comprising a polypeptide sequence as shown in SEQ ID NO: 2, 4, 6, 8, 10, 12; 25 14, 16, 18, 20 or 22.

Homology between two nucleic acid sequences is understood as meaning the identity of the two nucleic acid sequences over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 50 | Length weight: 3 |
| Average match: 10 | Average mismatch: 0 |

For example a sequence which has at least 80% homology with sequence SEQ ID NO: 1 at the nucleic acid level is understood as meaning a sequence which, upon comparison with the sequence SEQ ID NO: 1 by the above program algorithm with the above parameter set, has at least 80% homology.

Homology between two polypeptides is understood as meaning the identity of the two nucleic acid sequences over in each case the entire sequence length which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389 et seq.), setting the following parameters:

| | |
|---|---|
| Gap weight: 8 | Length weight: 2 |
| Average match: 2,912 | Average mismatch: −2,003 |

For example a sequence which has at least 80% homology with sequence SEQ ID NO: 2 at the protein level is understood as meaning a sequence which, upon comparison with the sequence SEQ ID NO: 2 by the above program algorithm with the above parameter set, has at least 80% homology.

Functional equivalents derived from an NADPH oxidase comprising a polypeptide sequence as shown in SEQ ID NO: 2, 4, 6, 8, 10, 12, 14, 16, 18, 20 or 22 by substitution, insertion or deletion have at least 50%, preferably at least 70%, by preference at least 90%, especially preferably at least 95%, very especially preferably at least 98% homology with a polypeptide comprising a polypeptide sequence as shown in SEQ ID NO: 2, 4, 6, 8, 10, 12, 14, 16, 18, 20 or 22 and are distinguished by identical essential characteristics as the former.

Functional equivalents derived from an NAPDH oxidase nucleic acid sequence comprising a sequence as shown in SEQ ID NO: 1, 3, 5, 7, 9, 11, 13, 15, 17, 19 or 21 by substitution, insertion or deletion, have at least 50%, preferably at least 70%, by preference at least 90%, especially preferably at least 95%, very especially preferably at least 98% homology with one of the polypeptides according to the invention as shown in SEQ ID NO: 1, 3, 5, 7, 9, 11, 13, 15, 17, 19 or 21 and encode polypeptides with the same essential characteristics as a polypeptide comprising a sequence as shown in SEQ ID NO: 2, 4, 6, 8, 10, 12, 14, 16, 18, 20 or 22.

Also, screening cDNA libraries or genomic libraries of other organisms, preferably of the plant species which are mentioned further below as being suitable hosts for the transformation, using the nucleic acid sequences described under SEQ ID NO: 1, 3, 5, 7, 9, 11, 13, 15, 17, 19 or 21 or parts of these as probe, is a method known to the skilled worker for identifying homologs in other species. In this context, the probes derived from the nucleic acid sequences as shown in SEQ ID NO: 1, 3, 5, 7, 9, 11, 13, 15, 17, 19 or 21 have a length of at least 20 bp, preferably at least 50 bp, especially preferably at least 100 bp, very especially preferably at least 200 bp, most preferably at least 400 bp. A DNA strand which is complementary to the sequences described under SEQ ID NO: 1, 3, 5, 7, 9, 11, 13, 15, 17, 19 or 21 may also be employed for screening the libraries. Functional equivalents comprises DNA sequences which hybridize under standard conditions with the NAPDH oxidase nucleic acid sequences described under SEQ ID NO: 1, 3, 5, 7, 9, 11, 13, 15, 17, 19 or 21, the nucleic acid sequence complementary thereto or parts of the above and which, as complete sequences, encode proteins which have the same essential characteristics as a polypeptide comprising a sequence as shown in SEQ ID NO: 2, 4, 6, 8, 10, 12, 14, 16, 18, 20 or 22.

"Standard hybridization conditions" is to be understood in the broad sense and means stringent or else less stringent hybridization conditions. Such hybridization conditions are described, inter alia, by Sambrook J, Fritsch E F, Maniatis T et al., in Molecular Cloning (A Laboratory Manual), 2nd Edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the wash step can be selected from the range of conditions delimited by low-stringency conditions (approximately ×SSC at 50° C.) and high-stringency conditions (approximately 0.2×SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65°0 C. Both of the parameters, salt concentration and temperature, can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Some examples of conditions for hybridization and wash step are shown hereinbelow:

(1) Hybridization conditions can be selected, for example, from the following conditions:

a) 4×SSC at 65° C. (with—optionally—100 μg/ml denatured fragmented fish sperm DNA )
b) 6×SSC at 45° C. (with—optionally—100 μg/ml denatured fragmented fish sperm DNA ),
c) 6×SSC, 0.5% SDS, 50% formamide at 42° C. (with—optionally—100 μg/ml denatured fragmented fish sperm DNA)
d) 4×SSC, 50% formamide at 42° C. (with—optionally—100 μg/ml denatured fragmented fish sperm DNA)
e) 2×or 4×SSC at 50° C. (low-stringency condition),
f) 30 to 40% formamide, 2× or 4×SSC at 42° C. (low-stringency condition).

(2) Wash steps can be selected, for example, from the following conditions:

a) 0.015 M NaCl/0.0015 M sodium citrate/0.1% SDS at 50° C.
b) 0.1×SSC at 65° C.
c) 0.1×SSC, 0.5% SDS at 68° C.
d) 0.1×SSC, 0.5% SDS, 50% formamide at 42° C.
e) 0.2×SSC, 0.1% SDS at 42° C.
f) 2×SSC at 65° C. (low-stringency condition).

The reduction of the expression of an NADPH oxidase protein, the NADPH oxidase activity or the NADPH oxidase function can be performed in many ways.

"Reduction" or "to reduce" in connection with an NADPH oxidase, an NADPH oxidase activity or NADPH oxidase function is to be interpreted in the broad sense and comprises the partial or essentially complete prevention or blocking (due to a variety of cell-biological mechanisms) of the functionality of an NAPDH oxidase in a plant or a part, tissue, organ, cells or seed derived therefrom. A reduction for the purposes of the invention also comprises a quantitative reduction of an NADPH oxidase down to an essentially complete absence of the NAPDH oxidase (i.e. lack of detectability of NADPH oxidase activity or NADPH oxidase function, or lack of immunological detectability of the NADPH oxidase protein). In this context, one or more essential units of the NADPH oxidase can be reduced. In this context, the expression of a certain NADPH oxidase or the NADPH oxidase activity or NADPH oxidase function in a cell or an organism is reduced by preferably more than 50%, especially preferably more than 80%, very especially preferably more than 90%.

A variety of strategies for reducing the expression of an NADPH oxidase protein, the NADPH oxidase activity or NADPH oxidase function are comprised in accordance with the invention. Strategies which may be mentioned by way of example, but not by limitation, are:

a) Introducing a double-stranded NADPH oxidase RNA nucleic acid sequence (NAox-dsRNA) or (an) expression cassette(s) ensuring its expression;
b) Introducing an NADPH oxidase antisense nucleic acid sequence or an expression cassette ensuring its expression. Comprised are those methods in which the antisense nucleic acid sequence is directed against an NADPH oxidase gene (that is to say, genomic DNA sequences) or an NADPH oxidase gene transcript (that is to say, RNA sequences). Also comprised are α-anomeric nucleic acid sequences.
c) Introducing an NADPH oxidase antisense nucleic acid sequence in combination with a ribozyme or an expression cassette ensuring its expression
d) Introducing NADPH oxidase sense nucleic acid sequences for inducing a cosuppression or an expression cassette ensuring their expression
e) Introducing DNA- or protein-binding factors against NADPH oxidase genes, RNAs or proteins or an expression cassette ensuring their expression
f) Introducing viral nucleic acid sequences and expression constructs bringing about the degradation of NADPH oxidase RNA, or an expression cassette ensuring their expression
g) Introducing constructs for inducing a homologous recombination at endogenous NADPH oxidase genes, for example for the generation of knock-out mutants.
h) Introducing mutations into endogenous NADPH oxidase genes for generating a loss of function (for example generation of stop codons, reading frame shifts and the like)

Here, each and every one of these methods can bring about a reduction of the NADPH oxidase expression, NADPH oxidase activity or NADPH oxidase function in the sense of the invention. A combined use is also feasible. Further methods are known to the skilled worker and can comprise hindering or preventing the processing of the NADPH oxidase protein, the transport of the NADPH oxidase protein or its mRNA, inhibition of the attachment of ribosomes, inhibition of RNA splicing, induction of an NADPH oxidase RNA degrading enzyme and/or inhibition of the translational elongation or termination.

The individual methods which are preferred shall be described briefly hereinbelow:

a) Introducing a Double-stranded NADPH Oxidase RNA Nucleic Acid Sequence (NAox-dsRNA)

The method of regulating genes by means of double-stranded RNA (double-stranded RNA interference; dsRNAi) has been described many times in animal and plant organisms (for example Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). The processes and methods described in the abovementioned references are expressly referred to. Efficient gene suppression can also be shown in the case of transient expression or after transient expression, for example as the result of a biolistic transformation (Schweizer P et al. (2001) Plant J 2000 24:895-903). dsRNAi methods are based on the phenomenon that the simultaneous introduction of complementary strand and counterstrand of a gene transcript brings about a highly-efficient suppression of the expression of the gene in question. The phenotype which results is very similar to a corresponding knock-out mutant (Waterhouse PM et al. (1998) Proc Natl Acad Sci USA 95:13959-64).

The dsRNAi method has proved to be particularly efficient and advantageous when reducing the NADPH oxidase expression. As described in WO 99/32619, inter alia, dsRNAi approaches are markedly superior to traditional antisense approaches.

A further aspect of the invention therefore relates to double-stranded RNA molecules (dsRNA molecules) which, when introduced into a plant (or a cell, tissue, organ or seed derived therefrom), bring about the reduction of an NADPH oxidase.

The double-stranded RNA molecule for reducing the expression of an NADPH oxidase protein comprises a) a sense RNA strand comprising at least one ribonucleotide sequence which is essentially identical to at least part of an NADPH oxidase nucleic acid sequence, and b) an antisense RNA strand which is essentially—preferably completely—complementary to. the RNA sense strand of a).

In a furthermore preferred embodiment, the double-stranded RNA molecule for reducing the expression of an NADPH oxidase protein comprises a) a sense RNA strand comprising at least one ribonucleotide sequence which is essentially identical to at least part of the sense RNA transcript of a nucleic acid sequence encoding an NADPH oxidase protein, and b) an antisense RNA strand which is essentially—preferably completely—complementary to the RNA sense strand of a).

With regard to the double-stranded RNA molecules, NADPH oxidase nucleic acid sequence preferably means a sequence comprising a sequence as shown in SEQ ID NO: 1, 3, 5, 7, 9, 11, 13, 15, 17, 19 or 21.

"Essentially identical" means that the dsRNA sequence may also have insertions, deletions and individual point mutations in comparison with the NADPH oxidase target sequence or a functional equivalent target sequence while still bringing about an efficient reduction of the expression. Preferably, the homology as defined above between the sense strand of an inhibitory dsRNA and at least part of the sense RNA transcript of a nucleic acid sequence encoding an NAPDH oxidase protein or functional equivalent thereof (or between the antisense strand of the complementary strand of a nucleic acid sequence encoding an NAPDH oxidase protein or a functional equivalent thereof) amounts to at least 75%, preferably at least 80%, very especially preferably at least 90% most preferably 100%.

The length of the part-segment amounts to at least 10 bases, preferably at least 25 bases, especially preferably at least 50 bases, very especially preferably at least 100 bases, most preferably at least 200 bases or at least 300 bases.

Alternatively, an "essentially identical" dsRNA may also be defined as a nucleic acid sequence which is capable of hybridizing with a part of a storage protein gene transcript (for example in 400 mM NaCl, 40 mM PIPES pH 6.4, 1 mM EDTA at 50° C. or 70° C. for 12 to 16 h).

"Essentially complementary" means that the antisense RNA strand may also have insertions, deletions and individual point mutations in comparison with the complement of the sense RNA strand. Preferably, the homology between the antisense RNA strand and the complement of the sense RNA strand amounts to at least 80%, preferably at least 90%, very especially preferably at least 95%, most preferably 100%.

"Part of the sense RNA transcript" of a nucleic acid sequence encoding an NADPH oxidase protein or a functional equivalent thereof means fragments of an RNA or mRNA transcribed from a nucleic acid sequence encoding an NADPH oxidase protein or a functional equivalent thereof, preferably an NADPH oxidase gene. Here, the fragments preferably have a sequence length of at least 20 bases, preferably at least 50 bases, especially preferably at least 100 bases, very especially preferably at least 200 bases, most preferably at least 500 bases. Also comprised is the complete transcribed RNA or mRNA.

Also comprised is the use of the dsRNA molecules according to the invention in the methods according to the invention for generating a pathogen resistance in plants.

The dsRNA can consist of one or more strands of polymerized ribonucleotides. Furthermore, modifications both of the sugar-phosphate skeleton and of the nucleosides may be present. For example, the phosphodiester bonds of the natural RNA can be modified in such a way that they comprise at least one nitrogen or sulfur heteroatom. Bases can be modified in such a way that the activity of, for example, adenosine deaminase is limited. These and further modifications are described hereinbelow in the methods for stabilizing antisense RNA.

To achieve the same purpose it is, of course, also possible to introduce, into the cell or the organism, a plurality of individual dsRNA molecules, each of which comprises one of the above-defined ribonucleotide sequence segments.

The dsRNA can be produced enzymatically or, fully or in parts, by chemical synthesis.

The double-stranded dsRNA structure can be formed starting from two complementary, separate RNA strands or—preferably—starting from a single, autocomplementary RNA strand.

In the case of a single, autocomplementary strand, sense and antisense sequence can be linked by a linking sequence (linker) and form for example a hairpin structure. Preferably, the linking sequence may be an intron, which is spliced out after the dsRNA has been synthesized.

The nucleic acid sequence encoding a dsRNA may comprise further elements such as, for example transcription termination signals or polyadenylation signals.

If the two strands of the dsRNA are to be combined in a cell or plant, this may take place in various ways, for example:

a) transformation of the cell or plant with a vector which comprises both expression cassettes, b) cotransformation of the cell or plant with two vectors, where one comprises the expression cassettes with the sense strand and the other comprises the expression cassettes with the antisense strand, c) hybridizing two plants, each of which has been transformed with a vector, where one comprises the expression cassettes with the sense strand and the other comprises the expression cassettes with the antisense strand.

The formation of the RNA duplex can be initiated either outside the cell or within the same. As in WO 99/53050, the dsRNA may also comprise a hairpin structure by linking sense and antisense strand by a linker (for example an intron). The autocomplementary dsRNA structures are preferred since they merely require the expression of a construct and comprise the complementary strands always in an equimolar ratio.

The expression cassettes encoding the antisense or sense strand of a dsRNA or the autocomplementary strand of the dsRNA are preferably inserted into a vector and, using the methods described hereinbelow, stably (for example using selection markers) inserted into the genome of a plant in order to ensure durable expression of the dsRNA.

The dsRNA can be introduced using such an amount that at least one copy per cell is made possible. Larger amounts (for example at least 5, 10, 100, 500 or 1000 copies per cell) may, if appropriate, bring about a more efficient reduction.

As already described, 100% sequence identity between dsRNA and an NADPH oxidase gene transcript or the gene transcript of a functionally equivalent gene is not necessarily required in order to bring about an efficient reduction of the NADPH oxidase expression. Accordingly, there is the advantage that the method tolerates sequence deviations, as may be present as the result of genetic mutations, polymorphisms or evolutionary divergences. Using the dsRNA which has been generated starting from the NADPH oxidase sequence of an organism, it is thus, for example, possible to suppress the NAPDH oxidase expression in another organism. The high degree of sequence homology between the NADPH oxidase sequences from rice, maize and barley allows the conclusion that this protein is highly conserved within plants, so that the expression of a dsRNA derived from one of the NADPH oxidase sequences comprising a sequence as shown in SEQ ID NO: 1, 3, 5, 7, 9, 11, 13, 15, 17, 19 or 21 probably also has an advantageous effect in other plant species.

Owing to the high degree of homology between the individual NADPH oxidase proteins and their functional equivalents, it is also possible to suppress the expression of further homologous NAPDH oxidase proteins and/or their functional equivalents of the same organism or else the expression of NAPDH oxidase proteins in other related species, using a single dsRNA which has been generated starting from a specific NADPH oxidase sequence of an organism. For this purpose, the dsRNA preferably comprises sequence regions of NADPH oxidase gene transcripts which correspond to conserved regions. Said conserved regions can be deduced readily from sequence alignments.

The dsRNA can be synthesized either in vivo or in vitro. To this end, a sequence encoding a dsRNA can be introduced into an expression cassette under the control of at least one genetic control element (such as, for example, promoter, enhancer, silencer, splice donor or acceptor, polyadenylation signal). Suitable advantageous constructions are described hereinbelow. A polyadenylation is not necessary, nor do elements for initiating a translation have to be present.

A dsRNA can be synthesized chemically or enzymatically. To this end, cellular RNA polymerases or bacteriophage RNA polymerases (such as, for example, T3, T7 or SP6 RNA polymerase) can be used. Such methods for the in-vitro expression of RNA are described (WO 97/32016; U.S. Pat. Nos. 5,593,874; 5,698,425, 5,712,135, 5,789,214, 5,804,693). A dsRNA which has been synthesized in vitro, either chemically or enzymatically, can be isolated fully or in part from the reaction mixture, for example by extraction, precipitation, electrophoresis, chromatography or combination of these methods, before it is introduced into a cell, tissue or organism. The dsRNA can be introduced directly into the cell or else by applied extracellularly (for example into the interstitial space).

However, the plant is preferably transformed stably using an expression construct which brings about the expression of the dsRNA. Suitable methods are described hereinbelow.

b) Introduction of an NADPH Oxidase Antisense Nucleic Acid Sequence

Methods for suppressing a particular protein by preventing the accumulation of its mRNA by antisense technology have been described many times, also in plants (Sheehy et al. (1988) Proc Natl Acad Sci USA 85: 8805-8809; U.S. Pat. No. 4,801,340; Mol J N et al. (1990) FEBS Lett 268(2):427-430). The antisense nucleic acid molecule hybridized with, or binds to, the cellular mRNA and/or genomic DNA encoding the NADPH oxidase target protein to be suppressed, which suppresses the transcription and/or translation of the target protein. The hybridization can be brought about in the traditional manner via the formation of a stable duplex or—in the case of genomic DNA—by binding the antisense nucleic acid molecule with the duplex of the genomic DNA by specific interaction in the large groove of the DNA helix.

An antisense nucleic acid sequence suitable for reducing an NADPH oxidase protein can be derived using the nucleic acid sequence which encodes this protein, for example the nucleic acid sequence comprising a sequence as shown in SEQ ID NO: 1, 3, 5, 7, 9, 11, 13, 15, 17, 19 or 21, following the Watson-Crick base pair rules. The antisense nucleic acid sequence can be complementary to all of the transcribed mRNA of said protein, may be limited to the coding region or may consist of one oligonucleotide only, which is complementary to part of the coding or noncoding sequence of the mRNA. Thus, the oligonucleotide may, for example, be complementary to the region which comprises the translation start for said protein. Antisense nucleic acid sequences can have a length of, for example, 5, 10, 15, 20, 25, 30, 35, 40, 45 or 50 nucleotides, but may also be longer and comprise at least 100, 200, 500, 1000, 2000 or 5000 nucleotides. Antisense nucleic acid sequences can be expressed recombinantly or synthetized chemically or enzymatically using methods known to the skilled worker. In the case of chemical synthesis, natural or modified nucleotides may be used. Modified nucleotides can impart an increased biochemical stability to the antisense nucleic acid sequence and may lead to an increased physical stability of the duplex formed of antisense nucleic acid sequence and sense target sequence. Nucleotides which can be used are, for example, phosphorothioate derivatives and acridine-substituted nucleotides such as 5-fluorouracil, 5-bromouracil, 5-chlorouracil, 5-iodouracil, hypoxanthin, xanthin, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 5-methyl-2-thiouracil, 3-(3-amino-3-N-2-carboxypropyl)uracil and 2,6-diaminopurine.

In a further preferred embodiment, the expression of an NADPH oxidase protein can be inhibited by nucleotide sequences which are complementary to the regulatory region of an NADPH oxidase gene (for example an NADPH oxidase promoter and/or enhancer) and form triple-helical structures with the DNA double helix therein, so that the transcription of the NADPH oxidase gene is reduced. Suitable methods are described (Helene C (1991) Anticancer Drug Res 6(6):569-84; Helene C et al. (1992) Ann NY Acad Sci 660:27-36; Maher L J (1992) Bioassays 14(12):807-815).

In a further embodiment, the antisense nucleic acid molecule can be an α-anomeric nucleic acid. Such a-anomeric nucleic acid molecules form specific double-stranded hybrids with complementary RNA in which—in contrast to the conventional β-nucleic acids—the two strands are parallel to one another (Gautier C et al. (1987) Nucleic Acids Res 15:6625-6641). The antisense nucleic acid molecule can furthermore also comprise 2'-O-methylribonucleotides (Inoue et al. (1987) Nucleic Acids Res 15:6131-6148) or chimeric RNA-DNA analogs (Inoue et al. (1987) FEBS Lett 215:327-330).

c) Introduction of an NADPH Oxidase Antisense Nucleic Acid Sequence in Combination with a Ribozyme The above-described antisense strategy can advantageously be coupled with a ribozyme method. Catalytic RNA molecules or ribozymes can be adapted to any target RNA and cleave the phosphodiester backbone at specific positions, whereby the target DNA is functionally deactivated (Tanner N K (1999) FEMS Microbiol Rev 23(3):257-275). The ribozyme itself is not modified thereby, but is capable of cleaving further target RNA molecules in an analogous manner, whereby it gains the properties of an enzyme. The incorporation of ribozyme sequences into antisense RNAs imparts to these antisense-RNAs this enzyme-like, RNA-cleaving property and thus increases their efficiency in the inactivation of the target RNA. The preparation and use of suitable ribozyme antisense RNA molecules is described for example by Haseloff et al. (1988) Nature 334:585-591.

In this manner, ribozymes (for example Hammerhead ribozymes; Haselhoff and Gerlach (1988) Nature 334:585-591) can be used for catalytically cleaving the mRNA of an enzyme to be suppressed—for example NADPH oxidase—and for preventing translation. The ribozyme technology can increase the efficiency of an antisense strategy. Methods for the expression of ribozymes for reducing certain proteins are described in (EP 0 291 533, EP 0 321 201, EP 0 360 257). Ribozyme expression in plant cells is also described (Steinecke P et al. (1992) EMBO J 11(4):1525-1530; de Feyter R et al. (1996) Mol Gen Genet. 250(3):329-338). Suitable target sequences and ribozymes can be determined for example as described by "Steinecke P, Ribozymes, Methods in Cell Biology 50, Galbraith et al. eds, Academic Press, Inc. (1995), pp. 449-460", by calculating the secondary structure of ribozyme RNA and target RNA, and by their interaction (Bayley CC et al. (1992) Plant Mol Biol. 18(2):353-361; Lloyd A M and Davis R W et al. (1994) Mol Gen Genet. 242(6):653-657). For example, it is possible to construct derivatives of the Tetrahymena L-19 IVS RNA, which have complementary regions to the mRNA of the NADPH oxidase protein to be suppressed (see also U.S. Pat. Nos. 4,987,071 and 5,116,742). Alternatively, such ribozymes can also be identified from a library of diverse ribozymes, using a selection process (Bartel D and Szostak J W (1993) Science 261:1411-1418).

d) Introducing an NADPH Oxidase Sense Nucleic Acid Sequence for Inducing a Cosuppression The expression of an NADPH oxidase nucleic acid sequence in sense orientation can lead to a cosuppression of the corresponding homologous, endogenous gene. The expression of sense RNA with homology to an endogenous gene can reduce or switch off the expression of same, similarly to what has been described for antisense approaches (Jorgensen et al. (1996) Plant Mol Biol 31(5):957-973; Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-99). Here, the introduced construct can fully or only partly represent the homologous gene to be reduced. The possibility of translation is not required. The application of this technology to plants is described for example by Napoli et al. (1990) The Plant Cell 2: 279-289 and in U.S. Pat. No. 5,034,323.

Preferably, cosuppression is carried out using a sequence which is essentially identical to at least a part of the nucleic acid sequence encoding an NADPH oxidase protein or a functional equivalent thereof, for example the nucleic acid sequence comprising a sequence as shown in SEQ ID NO: 1, 3, 5, 7, 9, 11, 13, 15, 17, 19 or 21.

e) Introducing DNA—or Protein-binding Factors Against NADPH Oxidase Genes, RNAs or Proteins A reduction of an NADPH oxidase gene expression is also possible using specific DNA-binding factors, for example with factors of the zinc finger transcription factor type. These factors anneal with the genomic sequence of the endogenous target gene, preferably in the regulatory regions, and bring about a repression of the endogenous gene. The use of such a method makes it possible to reduce the expression of an endogenous NADPH oxidase gene without it being necessary to recombinantly manipulate the sequence of the latter. Suitable methods for the generation of suitable factors are described (Dreier B et al. (2001) J Biol Chem 276(31):29466-78; Dreier B et al. (2000) J Mol Biol 303(4):489-502; Beerli R R et al. (2000) Proc Natl Acad Sci USA 97 (4):1495-1500; Beerli R R et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275 (12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

These factors may be selected using any desired portion of an NADPH oxidase gene. Preferably, this segment is located within the promoter region. For gene suppression, however, it may also be located in the region of the coding exons or introns. The corresponding segments are obtainable for the skilled worker by means of database search from the genetic library or—starting from an NADPH oxidase c whose gene is not present in the genetic library, by screening a genomic library for corresponding genomic clones. The methods required for this purpose are known to the skilled worker.

Furthermore, it is possible to introduce, into a cell, factors which inhibit the NADPH oxidase target protein itself. The protein-binding factors may be for example aptamers (Famulok M and Mayer G (1999) Curr Top Microbiol Immunol 243:123-36) or antibodies or antibody fragments or single-chain antibodies. The way in which these factors are obtained is described and known to the skilled worker. For example, a cytoplasmic scFv antibody has been employed for modulating the activity of the phytochrome A protein in genetically modified tobacco plants (Owen M et al. (1992) Biotechnology (NY) 10(7):790-794; Franken E et al. (1997) Curr Opin Biotechnol 8(4):411-416; Whitelam (1996) Trend Plant Sci 1:286-272).

Gene expression can also be suppressed by tailor-made low-molecular-weight synthetic compounds, for example of the polyamide type (Dervan P B and Bürli R W (1999) Current Opinion in Chemical Biology 3:688-693; Gottesfeld J M et al. (2000) Gene Expr 9(1-2):77-91). These oligomers consist of the units 3-(dimethylamino)propylamine, N-methyl-3-hydroxypyrrole, N-methylimidazole and N-methylpyrrole and can be adapted to any portion of double-stranded in such a way that they bind sequence-specifically in the large groove and block the expression of the gene sequences which are located therein. Suitable methods are described (see, inter alia, Bremer R E et al. (2001) Bioorg Med Chem. 9(8):2093-103; Ansari A Z et al. (2001) Chem Biol. 8(6):583-92; Gottesfeld J M et al. (2001) J Mol Biol. 309(3):615-29; Wurtz N R et al. (2001) Org Lett 3(8):1201-3; Wang C C et al. (2001) Bioorg Med Chem 9(3):653-7; Urbach A R and Dervan P B (2001) Proc Natl Acad Sci USA 98(8):4343-8; Chiang S Y et al. (2000) J Biol Chem. 275(32):24246-54).

f) Introducing Viral Nucleic Acid Sequences and Expression Constructs which Bring About the Degradation of NADPH Oxidase RNA NADPH oxidase expression can also be brought about efficiently by inducing the specific NADPH oxidase RNA degradation by the plant with the aid of a viral expression system (amplicon) (Angell, S M et al. (1999) Plant J. 20(3): 357-362). These systems—also referred to as "VIGS" (viral induced gene silencing)—introduce nucleic acid sequences with homology to the transcripts to be suppressed into the plant, using viral vectors. Then, transcription is switched off, probably mediated by plant defense mechanisms against viruses. Suitable techniques and methods are described (Ratcliff F et al. (2001) Plant J 25(2):237-45; Fagard M and Vaucheret H (2000) Plant Mol Biol 43(2-3):285-93; Anandalakshmi R et al. (1998) Proc Natl Acad Sci USA 95(22): 13079-84; Ruiz M T (1998) Plant Cell 10(6): 937-46).

g) Introducing Constructs for the Induction of a Homologous Recombination on Endogenous NADPH Oxidase Genes, for Example for the Generation of Knock-out Mutants.

To generate a homologously recombinant organism with reduced NADPH oxidase activity, for example a nucleic acid construct is used which comprises at least a part of the endogenous NADPH oxidase gene which is modified by a deletion, addition or substitution of at least one nucleotide in such a way that the functionality is reduced or nullified completely. The modification may also affect the regulatory elements (for example the promoter) of the gene, so that the coding sequence remains unaltered, but expression (transcription and/or translation) does not take place and is reduced.

In the case of conventional homologous recombination, the modified region is flanked at its 5' and 3' end by further nucleic acid sequences which must have a sufficient length for making possible the recombination. The length is, as a rule, in the range of from several hundred bases to several kilobases (Thomas K R and Capecchi M R (1987) Cell 51:503; Strepp et al. (1998) Proc Natl Acad Sci USA 95(8):4368-4373). For the homologous recombination, the host organism—for example a plant—is transformed with the recombination construct using the methods describe hereinbelow, and clones which have undergone successful recombination are selected using, for example, an antibiotic or herbicide resistance.

Homologous recombination is a relatively rare event in higher eukaryotes, especially in plants. Random integrations into the host genome predominate. A possibility of removing the randomly integrated sequences and thus of enriching cell clones with a correct homologous recombination consists in using a sequence-specific recombination system as described in U.S. Pat. No. 6,110,736, by which unspecifically integrated sequences can be deleted, which facilitates the selection of events which have integrated successfully via homologous recombination. A multiplicity of sequence-specific recombination systems can be used, examples which may be mentioned being the Cre/lox system of the bacteriophage P1, the FLP/FRT system of yeast, the Gin recombinase of the phage Mu, the Pin recombinase from *E. coli* and the R/RS system of the plasmid pSR1. Preferred are the bacteriophage P1 Cre/lox and the yeast FLP/FRT system. The FLP/FRT and cre/lox recombinase system has already been employed in plant systems (Odell et al. (1990) Mol Gen Genet 45 223: 369-378)

h) Introducing Mutations into Endogenous NADPH Oxidase Genes for Generating a Loss of Function (for Example Generation of Stop Codons, Reading Frame Shifts and the Like)

Further suitable methods for reducing the NADPH oxidase activity are the introduction of nonsense mutations into endogenous NADPH oxidase genes, for example by means of introducing RNA/DNA oligonucleotides into the plant (Zhu et al. (2000) Nat Biotechnol 18(5):555-558), and the generation of knockout mutants with the aid of, for example, T-DNA mutagenesis (Koncz et al. (1992) Plant Mol Biol 20(5):963-976), ENU (N-ethyl-N-nitrosourea) mutagenesis or homologous recombination (Hohn B and Puchta (1999) H Proc Natl Acad Sci USA 96:8321-8323). Point mutations can also be generated by means of -RNA hybrids, which are also known as chimeraplasty (Cole-Strauss et al. (1999) Nucl Acids Res 27(5):1323-1330; Kmiec (1999) Gene Therapy American Scientist 87(3):240-247). The methods of dsRNAi, cosuppression by means of sense RNA and VIGS (virus-induced gene silencing) are also referred to as post-transcriptional gene silencing (PTGS). PTGS methods, including the reduction of the NADPH oxidase function or activity with dominant-negative NADPH oxidase variants are especially advantageous since the requirements to the homology between the endogenous gene to be suppressed and the transgenically expressed sense or dsRNA nucleic acid sequence (or between the endogeous gene and its dominant-negative variant, respectively) are lower than, for example in the case of a traditional antisense approach. Suitable homology criteria are mentioned in the description of the dsRNAi method and applied generally to PTGS methods or dominant-negative approaches. Owing to the high degree of homology between the NADPH oxidase proteins from maize, rice and barley, a high degree of conservation of these protein in plants can be deduced. Thus, using the NADPH oxidase nucleic acid sequences from barley, maize or rice, it is probably also possible efficiently to suppress the expression of homologous NADPH oxidase proteins in other species, without the isolation and structural elucidation of the NADPH oxidase homologs in these species being necessarily required. This substantially reduces the labor involved. Analogously, using dominant-negative variants of an NADPH oxidase protein from rice, maize or barley, it is presumably also possible efficiently to reduce or suppress the function/activity of its homolog in other plant species.

All substances and compounds which directly or indirectly bring about a reduction of the protein quantity, RNA quantity, gene activity or protein activity of an NADPH oxidase protein, shall hereinbelow be grouped together under the term "anti-NADPH oxidase" compounds. The term "anti-NADPH oxidase" compound explicitly includes the nucleic acid sequences, peptides, proteins or other factors employed in the above-described methods. For the purposes of the invention, "introduction" comprises all those methods which are suitable for introducing an anti-NAPDH oxidase compound directly or indirectly into a plant or a cell, compartment, tissue, organ or seed thereof, or generating it therein. Direct and indirect methods are comprised. The introduction can lead to a transient presence of an anti-NADPH-oxidase compound (for example a dsRNA) or else to a stable presence.

In accordance with the different nature of the above-described approaches, the anti-NADPH-oxidase compound can exert its function directly (for example by insertion into an endogenous NADPH oxidase gene). However, the function can also be exerted indirectly after transcription into an RNA (for example in the case of antisense approaches) or after transcription and translation into a protein (for example binding factors). Both directly and indirectly acting anti-NADPH-oxidase compounds are comprised in accordance with the invention.

"Introducing" comprises for example methods such as transfection, transduction or transformation.

Thus, for example, anti-NADPH-oxidase compounds also comprise recombinant expression constructs which bring about an expression (i.e. transcription and, if appropriate, translation) of, for example, an NADPH oxidase dsRNA or an NADPH oxidase antisense RNA—preferably in a plant or a part, tissue, organ or seed thereof. In said expression constructs, a nucleic acid molecule whose expression (transcription and, if appropriate, translation) generates an anti-NADPH-oxidase compound, is preferably in functional linkage with at least one genetic control element (for example a promoter) which ensures expression in an organism, preferably in plants. If the expression construct is to be introduced directly into the plant and the anti-NADPH-oxidase compound (for example the NADPH oxidase dsRNA) is to be generated therein in plantae, then plant-specific genetic control elements (for example promoters) are preferred. However, the anti-NADPH-oxidase compound can also be generated in other organisms or in vitro and then be introduced into the plant (as described in Example 6 and 7). Here, preferred control elements are all those prokaryotic or eukaryotic genetic control elements (for example promoters) which permit the expression in the organism selected in each case for the production.

Functional linkage is to be understood as meaning, for example, the sequential arrangement of a promoter with the nucleic acid sequence to be expressed (for example an anti-NAox compound) and, if appropriate, further regulatory elements such as, for example, a terminator in such a way that each of the regulatory elements can fulfill its function when the nucleic acid sequence is expressed recombinantly depending on the arrangement of the nucleic acids into sense on antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other.

Here, the distance between the promoter sequence and the nucleic acid sequence to be expressed recombinantly is less than 200 base pairs, especially preferably less than. 100 base pairs, very especially preferably less than 50 base pairs.

Functional linkage, and an expression cassette, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (N.Y.), in Silhavy T J, Berman M L and Enquist L W (1984). Experiments with Gene Fusions, Cold Spring Harbor Laboratory, Cold Spring Harbor (N.Y.), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

However, an expression cassette also denotes those constructions in which a promoter is placed behind an endogenous NADPH oxidase gene—for example by a homologous recombination—and the reduction according to the invention, of an NADPH oxidase protein, is brought about by expressing an antisense NADPH oxidase RNA. Analogously, an anti-NADPH-oxidase compound (for example a nucleic acid compound encoding an NADPH oxidase dsRNA or an NADPH oxidase antisense RNA) can be placed behind an endogenous promoter in such a way that the same effect occurs. Both approaches lead to expression cassettes in the sense of the invention.

The term plant-specific promoters is understood as meaning, in principle, any promoter which is capable of governing the expression of genes, in particular foreign genes, in plants or plant parts, plant cells, plant tissues, or plant cultures. Here, expression may be, for example, constitutive, inducible or development-dependent.

The following are preferred:

a) Constitutive Promoters

Preferred vectors are those which make possible a constitutive expression in plants (Benfey et al. (1989) EMBO J 8:2195-2202). "Constitutive" promoter is understood as meaning those promoters which ensure expression in a large number of, preferably all, tissues over a substantial period of plant development, preferably at all stages of plant development. In particular a plant promoter or a promoter derived from a plant virus are preferably used. Particularly preferred is the promoter of the CaMV cauliflower mosaic virus 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202). Another suitable constitutive promoter is the Rubisco small subunit (SSU) promoter (U.S. Pat. No. 4,962,028), the leguminB promoter (GenBank Acc. No. X03677), the *Agrobacterium nopaline* synthase promoter, the TR dual promoter, the *Agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the ATPase subunits or the promoter of a proline-rich protein from wheat (WO 91/13991), and further promoters of genes whose constitutive expression in plants is known to the skilled worker. Especially preferred as constitutive promoter is the promoter of the nitrilase-1 (nit1) gene from A. thaliana (GenBank Acc. No.: Y07648.2, Nucleotide 2456-4340, Hillebrand et al. (1996) Gene 170:197-200).

b) Tissue-specific Promoters

Preferred are furthermore promoters with specificity for the anthers, ovaries, flower, leaves, stems, roots and seeds.

Seed-specific promoters comprise, for example, the phaseolin promoter (U.S. Pat. No. 5,504,200; Bustos M M et al. (1989) Plant Cell 1(9):839-53), the 2S albumin promoter (Joseffson L G et al. (1987) J Biol Chem 262:12196-12201), the legumin promoter (Shirsat A et al. (1989) Mol Gen Genet 215(2): 326-331), the USP (unknown seed protein) promoter (Baumlein H et al. (1991) Mol Gen Genet 225(3):459-467, the napin promoter (U.S. Pat. No. 5,608,152; Stalberg K et al. (1996) L Planta 199:515-519), the sucrose binding protein promoter (WO 00/26388), the legumin B4 promoter (LeB4; Bäumlein H et al. (1991) Mol Gen Genet 225: 121-128; Bäumlein H et al. (1992) Plant J 2(2):233-239; Fiedler U et al. (1995) Biotechnology (NY) 13(10):1090f), the *Arabidopsis oleosin* promoter (WO 98/45461), the *Brassica* Bce4 promoter (WO 91/13980). Further suitable seed-specific promoters are those of the genes encoding the high-molecular-weight glutenin (HMWG), gliadin, branching enzyme, ADP glucose pyrophosphatase (AGPase) or starch synthase. Furthermore preferred promoters are those which permit seed-specific expression in monocots such as maize, barley, wheat, rye, rice and the like. The following can be employed advantageously: the promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the kasirin gene, or the secalin gene).

Tuber-, storage-root- or root-specific promoters comprise, for example, the class I patatin promoter (B33), the potato cathepsin D inhibitor promoter.

Leaf-specific promoters comprise the potato cytosolic FBPase promoter (WO 97/05900), the Rubisco (ribulose-1, 5-bisphosphate carboxylase) SSU (small subunit) promoter or the ST-LSI promoter from potato (Stockhaus et al. (1989) EMBO J 8:2445-2451). Very especially preferred are epidermis-specific promoters such as, for example, the OXLP gene (oxalate-oxidase-like protein) promoter (Wei et al. (1998) Plant Mol Biol 36:101-112).

Flower-specific promoters comprise, for example, the phytoene synthase promoter (WO 92/16635) or the promoter of the P-rr gene (WO 98/22593).

Anther-specific promoters comprise, for example, the 5126 promoter (U.S. Pat. Nos. 5,689,049, 5,689,051), the glob-1 promoter and the γ-zein promoter.

c) Chemically Inducible Promoters

The expression cassettes can also comprise a chemically inducible promoter (review article: Gatz et al. (1997) Annu Rev Plant Physiol Plant Mol Biol 48:89-108), by which the expression of the exogenous gene in the plant at a particular point in time can be controlled. Examples which may be mentioned are the PRP1 promoter (Ward et al. (1993) Plant Mol Biol 22:361-366), a salicylic-acid-inducible promoter (WO 95/19443), a benzenesulfonamide-inducible promoter (EP 0 388 186), a tetracyclin-inducible promoter (Gatz et al. (1992) Plant J 2:397-404), an abscisic-acid-inducible promoter (EP 0 335 528) or an ethanol- or cyclohexanone-inducible promoter (WO 93/21334).

d) Stress- or Pathogen-inducible Promoters

Further preferred promoters are those which are induced by biotic or abiotic stress such as, for example, the pathogen-inducible promoter of the PRP1 gene (or gst1 promotor), for example from potato (WO 96/28561; Ward et al. (1993) Plant Mol Biol 22:361-366), the tomato high-temperature-inducible hsp70 or hsp80 promoter (U.S. Pat. No. 5,187,267), the potato low-temperature-inducible alpha-amylase promoter (WO 96/12814) or the light-inducible PPDK promoter. Further pathogen-inducible promoters comprise the flax Fis1 promoter (WO 96/34949), the Vst1 promoter (Schubert et al. (1997) Plant Mol Biol 34:417-426) and the tobacco EAS4 sesquiterpene cyclase promoter (U.S. Pat. No. 6,100,451).

Pathogen-inducible promoters furthermore comprise the promoters of genes which are induced as a consequence of infection by pathogens, such as, for example, genes of PR proteins, SAR proteins, β-1,3-glucanase, chitinase and the like (for example Redolfi et al. (1983) Neth J Plant Pathol 89:245-254; Uknes et al. (1992) Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968(1989).

Also comprised are wounding-inducible promoters such as that of the pinII gene (EP-A 0 375 091; Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin gene (McGurl et al. (1992) Science 225:1570-1573), of the WIP1gene (Rohmeier et al. (1993) Plant Mol Biol 22:783-792; Eckelkamp et al. (1993) FEBS Letters 323:73-76), of the MPI gene (Corderok et al. (1994) Plant J 6(2):141-150) and the like.

A source of further pathogen-inducible promoters is the PR gene family. A series of elements in these promoters has proved to be advantageous. Thus, the region −364 to −288 in the promoter of PR-2d mediates salicylate specificity (Buchel et al. (1996) Plant Mol Biol 30, 493-504). The sequence 5'-TCATCTTCTT-3' (SEQ ID NO: 36) occurs repeatedly in the promoter of the barley β-1,3-glucanase and in more than 30 further stress-induced genes. In tobacco, this region binds a nuclear protein whose abundance is increased by salicylate. The PR-1 promoters from tobacco and *Arabidopsis* (EP-A 0 332 104, WO 98/03536) are likewise suitable as pathogen-inducible promoters. Preferred, since especially specifically pathogen-induced, are the acidic PR-5(aPR5) promoters from barley (Schweizer et al. (1997) Plant Physiol 114:79-88) and wheat (Rebmann et al. (1991) Plant Mol Biol 16:329-331). aPR5 proteins accumulate in approximately 4 to 6 hours after pathogen attack and show only very little background expression (WO 99/66057). An approach for achieving an increased pathogen-induced specificity is the generation of synthetic promoters from combinations of known pathogen-responsive elements (Rushton et al. (2002) Plant Cell 14, 749-762; WO 00/01830; WO 99/66057). Further pathogen-inducible promoters from different species are known to the skilled worker (EP-A 1 165 794; EP-A 1 062 356; EP-A 1 041 148; EP-A 1 032 684).

e) Development-dependent Promoters

Further suitable promoters are, for example, fruit-maturation-specific promoters such as, for example, the tomato fruit-maturation-specific promoter (WO 94/21794, EP 409 625). Development-dependent promoters comprise partly the tissue-specific promoters since individual tissues develop by nature in a development-dependent fashion.

Especially preferred are constitutive promoters and also leaf-and/or stem-specific, pathogen-inducible and epidermis-specific promoters, with pathogen-inducible and epidermis-specific promoters being most preferred.

Furthermore, further promoters may be linked functionally to the nucleic acid sequence to be expressed, which promoters make possible an expression in further plant tissues or in other organisms, such as, for example, *E. coli* bacteria. Suitable plant promoters are, in principle, all of the above-described promoters.

The nucleic acid sequences present in the expression cassettes according to the invention can be linked operably to further genetic control sequences in addition to a promoter. The term "genetic control sequences" is to be understood in the broad sense and refers to all those sequences which have an effect on the generation or the function of the expression cassette according to the invention. For example, genetic control sequences modify the transcription and translation in prokaryotic or eukaryotic organisms. Preferably, the expression cassette according to the invention comprise the promoter with specificity for the embryonal epidermis and/or the flower 5'-upstream of the nucleic acid sequence in question to be expressed recombinantly, and 3'-downstream a terminator sequence as additional genetic control sequence and, if appropriate, further customary regulatory elements, in each case linked functionally to the nucleic acid sequence to be expressed recombinantly.

Genetic control sequences also comprise further promoters, promoter elements or minimal promoters, all of which can modify the expression-governing properties. Thus, for example, the tissue-specific expression may additionally depend on certain stress factors, owing to genetic control sequences. Such elements have been described, for example, for water stress, abscisic acid (Lam E and Chua N H (1991) J Biol Chem 266(26): 17131-17135) and heat stress (Schoffl F et al. (1989) Mol Gen Genetics 217(2-3):246-53).

In principle, all natural promoters together with their regulatory sequences such as those mentioned above may be used for the method according to the invention. In addition, synthetic promoters may also be used advantageously.

Genetic control sequences furthermore also comprise the 5'-untranslated regions, introns or noncoding 3'-region of genes, such as, for example, the actin-1 intron, or the Adhl-S introns 1, 2 and 6 (general reference: The Maize Handbook, Chapter 116, Freeling and Walbot, Eds., Springer, New York (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5'leader sequence (Gallie et al. (1987) Nucl Acids Res 15:8693-8711) and the like. Furthermore, they may promote tissue specificity (Rouster J et al. (1998) Plant J 15:435-440).

The expression cassette may advantageously comprise one or more of what are known as enhancer sequences, linked functionally to the promoter, which make possible an increased recombinant expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

Polyadenylation signals which are suitable as control sequences are plant polyadenylation signals, preferably those which essentially correspond to T-DNA polyadenylation signals from *Agrobacterium tumefaciens*, in particular to gene 3 of the T-DNA (octopine synthase) of the Ti plasmid pTiACHS (Gielen et al. (1984) EMBO J 3:835 et seq.) or functional equivalents thereof. Examples of terminator sequences which are especially suitable are the OCS (octopine synthase) terminator and the NOS (nopaline synthase) terminator.

Control sequences are furthermore to be understood as those which make possible homologous recombination or insertion into the genome of a host organism or which permit removal from the genome. Upon homologous recombination, for example the natural promoter of a particular gene can be exchanged to a promoter with specificity for the embryonal epidermis and/or the flower. Methods such as the cre/lox technology permit a tissue-specific, if appropriate inducible, removal of the expression cassette from the genome of the host organism (Sauer B (1998) Methods. 14(4):381-92). Here, certain flanking sequences (lox sequences), which later make possible a removal by means of the cre recombinase, are added to the target gene.

An expression cassette and vectors derived therefrom may comprise further functional elements. The term functional element is to be understood in the broad sense and refers to all those elements which have an effect on the generation, amplification or function of the expression cassettes, vectors or transgenic organisms according to the invention. The following may be mentioned by way of example, but not by limitation:

a) Selection markers which confer a resistance to metabolism inhibitors (such as 2-deoxyglucose-6-phosphate (WO 98/45456)), antibiotics or biocides, preferably herbicides, such as, for example, kanamycin, G 418, bleomycin, hygromycin or phosphinothricin etc. Especially preferred selection markers are those which confer resistance to herbicides. Examples which may be mentioned are: DNA sequences which encode phosphinothricin acetyl transferases (PAT) and which inactivate glutamin synthase inhibitors (bar and pat genes), 5-enolpyruvylshikimate-3-phosphate synthase genes (EPSP synthase genes), which confer resistance to Glyphosate® (N-(phosphonomethyl) glycine), the gox gene, which encodes Glyphosate®-degrading enzymes (glyphosate oxidoreductase), the deh gene (encoding a dehalogenase which inactivates Dalapon), sulfonylurea- and imidazolinone-inactivating acetolactate synthases, and bxn genes, which encode bromoxynil-degrading nitrilase enzymes, the aasa gene, which confers resistance to the antibiotic apectinomycin, the streptomycin phosphotransferase (spt) gene, which allows resistance to streptomycin, the neomycin phosphotransferase (nptII) gene, which confers resistance to kanamycin or geneticin, the hygromycin phosphotransferase (hpt) gene, which mediates resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and, via their color or enzyme activity, make possible an assessment of the transformation efficacy, the site of expression or the time of expression. Very especially preferred in this context are reporter proteins (Schenborn E, Groskreutz D. Mol Biotechnol. 1999; 13(1):29-44) such as the green fluorescent protein (GFP) (Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8), chloramphenicol transferase, a luciferase (Ow et al. (1986) Science 234:856-859; Millar et al. (1992) Plant Mol Biol Rep 10:324-414), the aequoringen (Prasher et al. (1985) Biochem Biophys Res Commun 126(3):1259-1268), β-galactosidase, R-locus gene (encode a protein which regulates the production of anthocyanin pigments (red coloration) in plant tissue and thus makes possible a direct analysis of the promoter activity without addition of extra adjuvants or chromogenic substrates; Dellaporta et al., In: Chromosome Structure and Function: Impact of New Concepts, 18th Stadler Genetics Symposium, 11:263-282, 1988), with β-glucuronidase being very especially preferred (Jefferson et al., EMBO J. 1987, 6, 3901-3907).

c) Origins of replication, which ensure amplification of the expression cassettes or vectors according to the invention in, for example, *E. coli*. Examples which may be mentioned are ORI (origin of DNA replication) the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are necessary for Agrobacterium-mediated plant transformation, such as, for example, the right or left border of the T-DNA or the vir region.

The introduction of an expression cassette according to the invention into an organism or cells, tissues, organs, parts or seeds thereof (preferably into plants or plant cells, tissue, organs, parts or seeds) can be effected advantageously using vectors which comprise the expression cassettes. The expression cassette can be introduced into the vector (for example a plasmid vector) via a suitable restriction cleavage site. The plasmid formed is first introduced into *E. coli*. Correctly transformed *E. coli* are selected, grown, and the recombinant plasmid is obtained by the methods familiar to the skilled worker. Restriction analysis and sequencing may serve to verify the cloning step.

Examples of vectors may be plasmids, cosmids, phages, viruses or else agrobacteria. In an advantageous embodiment, the expression cassette is introduced by means of plasmid vectors. Preferred vectors are those which make possible a stable integration of the expression cassette into the host genome.

The generation of a transformed organism (or of a transformed cell or tissue) requires that the DNA , RNA or protein in question is introduced into the corresponding host cell.

A multiplicity of methods are available for this procedure, which is termed transformation (or transduction or transfection) (Keown et al. (1990) Methods in Enzymology 185:527-537). For example, the DNA or RNA can be introduced directly by microinjection or by bombardment with DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Suitable methods have been described (for example by Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al.(1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the above-described methods of transforming and regenerating plants from plant tissues or plant cells are exploited for transient or stable transformation. Suitable methods are especially protoplast transformation by polyethylene-glycol-induced DNA uptake, the biolistic method with the gene gun, what is known as the particle bombardment method, electroporation, incubation of dry embryos in DNA-containing solution, and microinjection.

In addition to these "direct" transformation techniques, transformation can also be effected by bacterial infection by means of *Agrobacterium tumefaciens* or *Agrobacterium rhizogenes*. The Agrobacterium-mediated transformation is best suited to dicotyledonous plant cells. The methods are described, for example, by Horsch R B et al. (1985) Science 225: 1229f.

When agrobacteria are used, the expression cassette must be integrated into specific plasmids, either into a shuttle or intermediate vector, or into-a binary vector. If a Ti or Ri plasmid is to be used for the transformation, at least the right border, but in most cases the right and left border, of the Ti or Ri plasmid T-DNA is linked to the transgenic expression construct to be introduced in the form of a flanking region.

Binary vectors are preferably used. Binary vectors are capable of replication both in *E. coli* and in *Agrobacterium*. As a rule, they comprise a selection marker gene for the selection of transformed plants (see above) and a linker or polylinker flanked by the right and left T-DNA border sequence. They can be transformed directly into *Agrobacterium* (Holsters et al. (1978) Mol Gen Genet 163:181-187). Apart from the T-DNA region, they can additionally comprise elements such as a selection marker gene for the selection of transformed *E. coli* or agrobacteria (e.g. the nptIII gene). The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema, In: The Binary Plant Vector System, Offsetdrukkerij Kanters B. V., Alblasserdam, Chapter V; An et al. (1985) EMBO J 4:277-287). Various binary vectors are known, some of which are commercially available such as, for example, pBI101.2 or pBIN19 (Clontech Laboratories, Inc. USA).

Further promoters which are suitable for expression in plants are described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type.

The plasmid used need not meet any particular requirements in the case of the injection or electroporation DNA of or RNA into plant cells. Simple plasmids such as those of the pUC series can be used. If complete plants are to be regenerated from the transformed cells, it is advantageous for an additional selectable marker gene to be located on the plasmid.

Stably transformed cells, i.e. those which contain the introduced DNA integrated into the DNA of the host cell, can be selected from untransformed cells when a selectable marker is part of the DNA introduced. Examples of genes which can act as markers are all those which are capable of conferring resistance to a biocide (for example an antibiotic, herbicide or a metabolism inhibitor such as 2-deoxyglucose-6-phosphate WO 98/45456) (see above). Transformed cells which express such marker genes are capable of surviving in the presence of concentrations of a corresponding antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5:81-84). The resulting plants can be bred and hybridized in the customary fashion. Two or more generations should be grown in order to ensure that the genomic integration is stable and hereditary.

The abovementioned methods are described, for example, in Jenes B et al.(1993) Techniques for Gene Transfer, in: Transgenic Plants, Vol. 1, Engineering and Utilization, edited by S D Kung and R Wu, Academic Press, pp. 128-143 and in Potrykus (1991) Annu Rev Plant Physiol Plant Molec Biol 42:205-225. The construct to be expressed is preferably cloned into a vector which is suitable for the transformation of *Agrobacterium tumefaciens*, for example pBin19 (Bevan et al. (1984) Nucl Acids Res 12:8711f).

As soon as a transformed plant cell has been generated, a complete plant can be obtained using methods known to the skilled worker. For example, callus cultures are used as starting material. The development of shoot and root can be induced from this as yet undifferentiated cell biomass in a known fashion. The shoots obtained can be planted out and bred.

The skilled worker is familiar with such methods of regenerating intact plants from plant cells and plant parts. Methods to do so are described, for example, by Fennell et al. (1992)

Plant Cell Rep. 11: 567-570; Stoeger et al (1995) Plant Cell Rep. 14:273-278; Jahne et al. (1994) Theor Appl Genet 89:525-533. The method according to the invention can advantageously be combined with further methods which bring about a pathogen resistance (for example against insects, fungi, bacteria, nematodes and the like), stress resistance or another improvement of the plant's properties. Examples are mentioned in Dunwell J M, Transgenic approaches to crop improvement, J Exp Bot. 2000;51 Spec No; pages 487-96, inter alia.

With regard to, for example, a nucleic acid sequence, an expression cassette or a vector comprising said nucleic acid sequence or an organism transformed with said nucleic acid sequence, expression cassette or vector, "transgenic" means all those constructs which have been generated by recombinant methods in which either a) the NADPH oxidase nucleic acid sequence, or b) a genetic control sequence which is functionally linked with the NADPH oxidase nucleic acid sequence, for example a promoter, or c) (a) and (b)

are not located in their natural genetic environment or have been modified by recombinant methods, an example of a modification being a substitution, addition, deletion, inversion or insertion of one or more nucleotide residues. Natural genetic environment refers to the natural chromosomal locus in the source organism, or to the presence in a genomic library. In the case of a genomic library, the natural genetic environment of the nucleic acid sequence is preferably at least partially retained. The environment flanks the nucleic acid sequence at at least one side and has a sequence length of at least 50 bp, preferably at least 500 bp, especially preferably at least 1000 bp, very especially preferably at least 5000 bp. A naturally occurring expression cassette for example the naturally occurring combination of the NADPH oxidase promoter and the corresponding NADPH oxidase gene—becomes a transgenic expression cassette when the latter is modified by nonnatural, synthetic ("artificial") methods such as, for example, mutagenization. Suitable methods are described (U.S. Pat. No. 5,565,350; WO 00/15815; see also above).

Another aspect of the invention relates to transgenic organisms transformed with at least one nucleic acid sequence, expression cassette or vector according to the invention, and to cells, cell cultures, tissues, parts—such as, for example in the case of plant organisms, leaves, roots and the like—or propagation material derived from such organisms. Organism is to be understood in the broad sense and means prokaryotic and eukaryotic organisms, preferably bacteria, yeasts, fungi, animal and plant organisms.

The following are preferred:

a) fungi such as *Aspergillus, Eremothecium, Trichoderma, Ashbya, Neurospora, Fusarium, Beauveria* or further fungi described in Indian Chem Eng. Section B. Vol 37, No 1,2 (1995) on page 15, table 6. Especially preferred is the filamentous Hemiascomycete *Ashbya gossypii* or *Eremothecium ashbyii*, b) yeasts such as *Candida, Saccharomyces, Hansenula* or *Pichia*, with *Saccharomyces cerevisiae* or *Pichia pastoris* (ATCC Accession No. 201178) being especially preferred, c) plants in accordance with the abovementioned definition for "plants", d) vertebrates and invertebrates. Especially preferred vertebrates are nonhuman mammals such as dogs, cats, sheep, goats, chickens, mice, rats, cattle or horses. Preferred animal cells comprise CHO, COS, HEK293 cells. Preferred invertebrates comprise insect cells such as *Drosophila* S2 and Spodoptera Sf9 or Sf21 cells, e) prokaryotic organisms such as Gram-positive or Gram-negative bacteria such as *Acetobacter, Gluconobacter, Corynebacterium, Brevibacterium, Bacillus, Clostridium, Cyanobacter, Escherichia* (especially *Escherichia coli*), *Serratia, Staphylococcus, Aerobacter, Alcaligenes, Penicillium* or *Klebsiella*.

Host or starting organisms which are preferred as transgenic organisms are especially plants in accordance with the abovementioned definition. Included within the scope of the invention are all genera and species of higher and lower plants of the Plant Kingdom. Furthermore included are the mature plants, seeds, shoots and seedlings, and parts, propagation materials and culture derived from them, for example cell cultures. Mature plants means plants at any developmental stage beyond the seedling stage. Seedling means a young immature plant in an early developmental stage. Plants which are especially preferred as host organisms are plants to which the method according to the invention for obtaining a pathogen resistance in accordance with the abovementioned criteria can be applied. Very especially preferred are monocotyledonous plants such as wheat, oats, millet, barley, rye, maize, rice, buckwheat, sorghum, triticale, spelt, linseed, sugar cane, and dicotyledonous crop plants such as oilseed rape, canola, cress, *Arabidopsis*, cabbages, soybeans, alfalfa, pea, bean plants, peanut, potato, tobacco, tomato, egg plant, capsicum, sunflower, tagetes, lettuce, Calendula, melon, pumpkin/squash or zucchini.

The transgenic organisms can be generated with the above-described methods for the transformation or transfection of organisms.

A further aspect of the invention relates to the use of transgenic organisms according to the invention and of the cells, cell cultures, parts—such as for example in the case of transgenic plant organisms roots, leaves and the like—and transgenic propagation material such as seeds or fruits derived from these organisms for the production of foodstuffs, feedstuffs, pharmaceuticals or fine chemicals.

Furthermore preferred is a method for the recombinant production of pharmaceuticals or fine chemicals in host organisms, where a host organism is transformed with one of the above-described expression cassettes and this expression cassette comprises one or more structural genes which encode the desired fine chemical or catalyze the biosynthesis of the desired fine chemical, the transformed host organism is cultured, and the desired fine chemical is isolated from the culture medium. This method can be applied widely for fine chemicals such as enzymes, vitamins, amino acids, sugars, fatty acids, natural and synthetic flavorings, aroma substances and colorants. Especially preferred is the production of tocopherols and tocotrienols and of carotenoids. Culturing the transformed host organisms, and the isolation from the host organisms or from the culture medium, are carried out with methods known to the skilled worker. The production of pharmaceuticals, such as, for example, antibodies or vaccines, is described by Hood E E, Jilka J M (1999) Curr Opin Biotechnol 10(4):382-6; Ma J K, Vine N D (1999) Curr Top Microbiol Immunol 236:275-92.

Sequences

1. SEQ ID NO: 1 nucleic acid sequence encoding a barley (*Hordeum vulgare*) NADPH oxidase.
2. SEQ ID NO: 2 amino acid sequence encoding a barley (*Hordeum vulgare*) NADPH oxidase.
3. SEQ ID NO: 3 nucleic acid sequence encoding a rice (*Oryza sativa* var. *japonica*) NADPH oxidase
4. SEQ ID NO: 4 amino acid sequence encoding a rice (*Oryza sativa* var. *japonica*) NADPH oxidase 5. SEQ ID NO: 5 nucleic acid sequence encoding a *Nicotiana tabacum* NADPH oxidase
6. SEQ ID NO: 6 amino acid sequence encoding a *Nicotiana tabacum* NADPH oxidase
7. SEQ ID NO: 7 nucleic acid sequence encoding a potato (*Solanum tuberosum*) NADPH oxidase
8. SEQ ID NO: 8 amino acid sequence encoding a potato (*Solanum tuberosum*) NADPH oxidase
9. SEQ ID NO: 9 nucleic acid sequence encoding a tomato (*Lycopersicon esculentum*) NADPH oxidase
10. SEQ ID NO: 10 amino acid sequence encoding a tomato (*Lycopersicon esculentum*) NADPH oxidase
11. SEQ ID NO: 11 nucleic acid sequence encoding a NADPH oxidase aus *Arabidopsis thaliana* (RbohF)
12. SEQ ID NO: 12 amino acid sequence encoding a NADPH oxidase aus NADPH oxidase *Arabidopsis thaliana* (RbohF)
13. SEQ ID NO: 13 nucleic acid sequence encoding an *Arabidopsis thaliana* (RbohD) NADPH oxidase
14. SEQ ID NO: 14 amino acid sequence encoding an *Arabidopsis thaliana* (RbohD) NADPH oxidase
15. SEQ ID NO: 15 nucleic acid sequence encoding a *Nicotiana tabacum* (rboh) NADPH oxidase
16. SEQ ID NO: 16 amino acid sequence encoding a *Nicotiana tabacum* (rboh) NADPH oxidase
17. SEQ ID NO: 17 nucleic acid sequence encoding a rice (*Oryza sativa* var. *japonica*) NADPH oxidase
18. SEQ ID NO: 18 amino acid sequence encoding a rice (*Oryza sativa* var. *japonica*) NADPH oxidase
19. SEQ ID NO: 19 nucleic acid sequence encoding an *Arabidopsis thaliana* (RbohC) NADPH oxidase
20. SEQ ID NO: 20 amino acid sequence encoding an *Arabidopsis thaliana* (RbohC) NADPH oxidase
21. SEQ ID NO: 21 nucleic acid sequence encoding an *Arabidopsis thaliana* (RbohA) NADPH oxidase
22. SEQ ID NO: 22 amino acid sequence encoding an *Arabidopsis thaliana* (RbohA) NADPH oxidase

```
23. SEQ ID NO: 23    oligonucleotide primer 5' NAOX
                     5'-GARCAAGGCTCTTTTGATTG-3'

24. SEQ ID NO: 24    oligonucleotide primer 3' Naox
                     5'-GAAATGCTCCTTATGGAATTC-3'
```

Figure

FIG. 1: RNA interference with pNAox-dsRNA reduces the penetration efficiency of powdery mildew of barley BghA6 in barley.

The relative penetration efficiency (RPE) was determined in five individual experiments with inoculation with Bgh from barley cv Pallas. The RPE is calculated as the difference between the penetration efficiency of pNAox-dsRNA-transformed cells and the penetration efficiency of control-dsRNA-transformed cells (here: average penetration efficiency 38.74%). The percent RPE (% RPE) is calculated from the RPE minus 1, multiplied by 100.

$$RPE = \frac{[PE \text{ in } pNAox\text{-}dsRNA\text{-transformed cells}]}{[PE \text{ in control-}dsRNA \text{ transformed cells}]}$$

$$\%\ RPE = 100 * (RPE - 1)$$

The columns (1) to (5) represent the % RPE (i.e. the deviation of the penetration efficiency from the average of the penetration efficiency of the control) when evaluating at least 100 interaction sites for in each case one independent experiment. The column (m) represents the average % RPE of the experiments. The error bar indicates the standard error.

"Control dsRNA" represents the parallel experiments with a control dsRNA. "pNAox" dsRNA represents the experiments with the dsRNA of the barley NADPH oxidase.

In cells which have been bombarded with pNAox-dsRNA, the % RPE was markedly (significance p=0.0054) reduced in comparison with cells bombarded with a control dsRNA (TR: human thyroid receptor dsRNA).

General Methods:

The chemical synthesis of oligonucleotides can be effected for example in the known manner by the phosphoamidite method (Voet, Voet, 2nd edition, Wiley Press New York, pages 896-897). The cloning steps carried out within the scope of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. (1989) Cold Spring Harbor Laboratory Press; ISBN 0-87969-309-6. Recombinant DNA molecules are sequenced with a laser fluorescence DNA sequencer from MWG Licor following the method of Sanger (Sanger et al. (1977) Proc Natl Acad Sci USA 74:5463-5467).

EXAMPLE 1

Plants, Pathogens and Inoculation

The variety Pallas was provided by Lisa Munk, Department of Plant Pathology, Royal Veterinary and Agricultural University, Copenhagen, Denmark. Its production is described (Kolster P et al. (1986) Crop Sci 26: 903-907).

Unless otherwise described, the seed, which had been pregerminated for 12 to 36 hours in the dark on damp filter paper, was placed at a rate of 5 kernels along the edge of a square pot (8×8 cm) in Fruhstorfer soil, type P, covered with soil and watered regularly with tap water. All plants were grown in controlled-environment cabinets or chambers at 16 to 18° C., 50 to 60% relative atmospheric humidity and a 16-hour-light/8-hour-dark photoperiod at 3000 or 5000 lux (photon flux density 50 or 60 $\mu$mols-$^1$m-$^2$) for 5 to 8 days and used in the experiments during the seedling stage. In experiments in which primary leaves were treated, the latter were fully developed.

Prior to carrying out the transient transfection experiments, the plants were grown in controlled environment cabinets or chambers at 24° C. daytime temperature, 20° C. nighttime temperature, 50 to 60% relative atmospheric humidity and a 16-hour-light/8-hour-dark photoperiod at 30 000 lux.

Powdery mildew of barley *Blumeria graminis* (DC) Speer f.sp. *hordei* Em. Marchal race A6 (Wiberg A (1974) Hereditas 77: 89-148) (BghA6) was used for the inoculation of barley plants. The fungus was provided from the Department of Biometry, JLU GieBen. The inoculum was propagated in controlled-environment chambers under identical conditions as described above for the plants by transferring the conidia of infected material to regularly grown 7-day-old barley plants cv. Golden Promise at a density of 100 conidia/mm$^2$.

The inoculation with BghA6 was carried out using 7-day-old seedlings by shaking off the conidia from infected plants in an inoculation tower at approximately 100 conidia/mm$^2$ (unless otherwise specified).

EXAMPLE 2

Cloning of the Barley pNAox cDNA Sequence

The cDNA fragments required for the isolation of the Hvp-NAox cDNA, its cloning, sequencing and generation of probes were obtained by RT-PCR using the "One Step RT-PCR Kit" (Life Technologies, Karlsruhe, Germany, or Qiagen, Hilden, Germany). To this end, a total RNA from barley seedlings was used as template. The RNA was isolated from Pallas 3, 5 and 7 days after germination. In addition, RNA was isolated from Pallas and from the backcrossed lines with mlo5, Mlg or Mla12 1, 2 and 5 days after inoculation with BghA6 on day 7 after germination. The RT-PCR was carried out using primers which are derived from conserved regions of the gp91phox homologs from rice and *Arabidopsis thaliana* (GenBank Acc. No.: X93301 and AB008111):

```
5' NAOX:
5'-GARCAAGGCTCTTTTGATTG-3'     (SEQ ID NO: 23)
and

3' Naox:
5' GAAATGCTCCTTATGGAATTC 3'    (SEQ ID NO: 24)
```

In each case 1000 ng of total DNA, 0.4 mM dNTPs, in each case 0.6 mM OPN-1 and OPN-2 primer, 10 μl of RNase inhibitor and 1 μl of enzyme mix in 1×RT buffer (one step RT-PCR Kit, Qiagen, Hilden) were employed for the reaction.

The following temperature program is used (PTC-100TM model 96V; MJ Research, Inc., Watertown, Mass.):

| | |
|---|---|
| 1 | cycle of 30 minutes at 50° C. |
| 1 | cycle of 150 seconds at 94° C. |
| 30 | cycles of 94° C. for 45 seconds, 55° C. for 1 minute and 72° C. for 2 minutes |
| 1 | cycle of 72° C. for 7 minutes |

The PCR products were separated by means of 2% w/v agarose gel electrophoresis. This gave a 378 bp RT-PCR product (SEQ ID NO: 1) which encodes a part of the open reading frame of the barley NADPH oxidase. The corresponding cDNA was isolated from an agarose gel and cloned in the pGEM-T vector (Promega, Mannheim, Germany) by means of T-overhang ligation. The cDNAs were sequenced starting from the plasmid DNA using the "Thermo Sequenase Fluorescent Labeled Primer Cycle Sequencing Kit" (Amersham, Freiburg, Germany). The construct was named pGEM-T-pNAox.

EXAMPLE 3

In-vitro Synthesis of the pNAox dsRNA

The plasmid, which had been employed for the in-vitro RNA transcription, comprises the T7 and SP6 promoters at the respective ends of the inserted nucleic acid sequence, which makes possible the synthesis of sense RNA and antisense RNA. The plasmid can be linearized with suitable restriction enzymes (ApaI for SP6 polymerase and PstI for T7 polymerase) in order to ensure correct transcription of the inserted nucleic acid sequence and to prevent read-through into vectorial sequences. To this end, in each case 10 μg of pGEM-T-pNAox plasmid DNA were cut with ApaI for SP6 polymerase and with and PstI for T7 polymerase. The cut plasmids are extracted in 200 μl of water with the same volume phenol/chloroform/isoamyl alcohol, transferred into a fresh Eppendorf vessel (RNAse-free) and centrifuged for 5 minutes at 20 000 g. 180 ρl of the plasmid solution were treated with 420 μl of ethanol, placed on ice and subsequently precipitated by centrifugation for 30 minutes at 20 000 g and −4° C. The precipitate was taken up in 10 μl of TE buffer. The preparations in question were employed directly in an in-vitro transcription with T7-RNA polymerase and with SP6-RNA polymerase, respectively. RNA polymerases were obtaied from Roche Molecular Biology, Mannheim, Germany.

Each transcription mixture contained the following in a volume of 40 μ:

2 μl linearized plasmid DNA (1 ∝g)
2 μl NTPs (25 mm) (1.25 mM of each NTP)
4 μl 10× reaction buffer (Roche Molecular Biology),
1 μl RNAsin RNAsin (27 units; Roche Molecular Biology),
2 μl RNA polymerase (40 units)
29 μl DEPC water After 2 hours of incubation at 37° C., in each case some of the reaction mixtures from the transcription of the sense and antisense strands were mixed, denatured for 5 minutes at 95° C. and thereafter hybridized with one another (annealed) by cooling over 30 minutes to a final temperature of 37° C. As an alternative, the mixture of sense and antisense strand can also be cooled for 30 minutes at −20° C. after the denaturation. The protein precipitate which formed during denaturation and hybridization was removed by briefly centrifuging at 20 800 g, and the supernatant was used directly for coating tungsten particles (see hereinbelow). For the analysis, in each case 1 μl of each RNA strand and of the dsRNA were separated on a non-denaturing agarose gel. Successful hybridization is evident by a band shift towards higher molecular weight in comparison with the individual strands.

4 μl of the dsRNA were precipitated with ethanol (by addition of 6 μl of water, 1 μl of 3M sodium acetate solution and 25 μl of ethanol, and centrifugation for at least 5 minutes at 20 000 g and 4° C.) and resuspended in 500 μl of water. The absorption spectrum between 230 and 300 nm was measured or the absorption at 280 and 260 nm was determined to determine the purity and the concentration of the dsRNA. As a rule, 80 to 100 μg of dsRNA with an $OD_{260}/OD_{280}$ ratio of 1.80 to 1.95 were obtained. If desired, a digestion with DNase I may be carried out, but this has no substantial effect on subsequent results.

The dsRNA of the human thyroid receptor (starting vector pT7beta-Sal (Norman C et al. (1988) Cell 55(6):989-1003), provided by Dr. Baniahmad, Department of Genetics, Giegen, Germany; the sequence of the insert is described under the GenBank Acc. No.: NM_000461) acted as control dsRNA. The plasmid was digested with PvuII to generate the sense RNA and with HindIII to generate the antisense RNA, and the RNA was then transcribed using T7 or SP6 RNA polymerase. The individual process steps for the generation of the control dsRNA are carried out analogously to those described above for the pNAox-dsRNA.

EXAMPLE 4

Transient Transformation, RNAi and Evaluation of the Development of the Fungal Pathogen Barley cv Pallas leaf segments were transformed with a pNAox dsRNA together with a GFP expression vector. Thereafer the leaves were inoculated with Bgh and the result was analyzed after 48 h by means of light and fluorescence microscopy. The penetration into GFP-expressing cells was assessed by detecting haustoria in live cells and by assessing the fungal development in precisely those cells. In all five experiments, the bombardment of barley cv Pallas with pNAox dsRNA resulted in a reduced number of cells which were successfully penetrated by Bgh in comparison with cells which had been bombarded with foreign control dsRNA (human thyroid hormone receptor dsRNA, TR). The resistance-inducing effect of the pNAox dsRNA resulted in an average reduction of the Bgh penetration efficiency by 35% (FIG. 1).

A method which had already been described for the biolistic introduction of dsRNA into epidermal cells of barley leaves was employed for the transient transformation (Schweizer P et al. (1999) Mol Plant Microbe Interact 12:647-54; Schweizer P et al. 2000) Plant J 2000 24: 895-903). Tungsten particles 1.1 μm in diameter (particle density 25 mg/ml) were coated with dsRNA (preparation see above) together with plasmid DNA of the vector pGFP (GFP under the control of the CaMV 35S promoters) as transformation marker. To this end, the following amounts of dsRNA and reporter plasmid were used for the coating per shot: 1 μg pGFP and 2 μg dsRNA. Double-stranded RNA was synthesized by annealing sense and antisense RNA in vitro (see above).

To prepare microcarriers, 55 mg of tungsten particles (M 17, diameter 1.1 μm; Bio-Rad, Munich) were washed twice with 1 ml of autoclave-distilled water and once with 1 ml of absolute ethanol, dried and taken up in 1 ml of 50% strength glycerol (approximately 50 mg/ml stock solution). The solution was diluted with 50% glycerol to 25 mg/ml, mixed thoroughly prior to use and suspended in an ultrasonic bath. To coat microcarriers, 1 μg of plasmid, 2 μg of dsRNA (1 μl), 12.5 μl of tungsten particle suspension (25 mg/ml), 12.5 μl of 1 M $Ca(NO_3)_2$ solution (pH 10) per shot were combined dropwise with constant mixing, left to stand for 10 minutes at RT, centrifuged briefly, and 20 μl of the supernatant were removed. The remainder with the tungsten particles is resuspended (ultrasonic bath) and employed in the experiment.

Barley primary leaf segments approximately 4 cm in length were used. The tissues were placed on 0.5% Phytagar (GibcoBRL™ Life Technologies™, Karlsruhe) supplemented with 20 μg/ml benzimidazole in Petri dishes (diameter 6.5 cm) and, immediately before the particle bombardment, the edges were covered with a stencil with a rectangular opening of dimensions 2.2 cm×2.3 cm. One after the other, the dishes were placed on the bottom of the vacuum chamber (Schweizer P et al. (1999) Mol Plant Microbe Interact 12:647-54) over which a nylon mesh (mesh size 0.2 mm, Millipore, Eschborn) had been inserted on a perforated sheet to act as diffusor (5 cm above the bottom, 11 cm underneath the macrocarriers, see hereinbelow) in order to diffuse particle clumps and to slow down the particle stream. The macrocarrier attached at the top of the chamber (plastic sterile filter holder, 13 mm, Gelman Sciences, Swinney, UK) was loaded with 5.8 μl of DNA-coated tungsten particles per shot (microcarriers, see hereinbelow). Using a diaphragm vacuum pump (Vacuubrand, Wertheim), the pressure in the chamber was reduced by 0.9 bar, and the tungsten particles were fired at the surface of the plant tissue at a helium-gas pressure of 9 bar. Immediately thereafter, the chamber was aerated. To label transformed cells, the leaves were bombarded with the plasmid (pGFP; vector on pUC18-basis, CaMV 35S promoter/terminator cassette with inserted GFP gene; Schweizer P et al. (1999) Mol Plant Microbe Interact 12:647-54; provided by Dr. P. Schweizer, Department of Plant Genetics IPK, Gatersleben, Germany). Each time a different plasmid was used for the bombardments, the macrocarrier was cleaned thoroughly with water beforehand. After incubation for four hours after the bombardment with slightly open Petri dishes at RT and with daylight, the leaves were incubated with 100 conidia/mm$^2$ of powdery mildew of barley (race A6) and incubated under identical conditions for a further 40 to 48 hours.

Leaf segments were bombarded with the coated particles using a article inflow gun. For each shot, 312 μg of tungsten particles ere applied. 4 hours after the bombardment, the leaves were inoculated with *Blumeria graminis* f.sp. *hordei* mildew (race A6) and, after a further 40 hours, evaluated for symptoms of infection. The result (for example the penetration efficiency, defined as percentage of attacked cells with a mature haustorium and a secondary elongating hypha were analyzed by means of fluorescence and light microscopy. An inoculation with 100 conidia/mm$^2$ results in an infection frequency of approximately 50% of the transformed cells. A minimum of 100 interaction sites was evaluated for each individual experiment. Transformed (GFP-expressing) cells were identified under excitation with blue light. Three different categories of transformed cells were distinguished:

1. Penetrated cells containing a readily recognizable haustorium. A cell with more than one haustorium was considered as one cell.
2. Cells which, while attacked by a fungal appressorium, contain no haustorium. A cell which has been attacked more than once by Bgh, but which contains no haustorium, was considered as one cell.
3. Cells which are not infected by Bgh.

Stomatal cells and guard cells were excluded from the assessment. Surface structures of Bgh were analyzed by means of light microscopy or fluorescence staining of the fungus with 0.1% Calcofluor (w/v in water) for 30 seconds. The fungal development can be evaluated readily by fluorescence microscopy following staining with Calcofluor. In pNAox-dsRNA-transformed cells, the fungus develops a primary and apressorial germ tube, but no haustorium. The development of a haustorium is a condition for the development of a secondary hypha.

The relative penetration efficiency (RPE) is calculated as the difference between the penetration efficiency of transformed cells (transformation with pNAox or control dsRNA) and the penetration efficiency of untransformed cells (here: average penetration efficiency 38.74%). The percent RPE (% RPE) is calculated from the RPE minus 1, multiplied by 100.

$$RPE = \frac{[PE \text{ in } pNAox\text{-}dsRNA\text{-transformed cells}]}{[PE \text{ in control-}dsRNA \text{ transformed cells}]}$$

$$\%\ RPE = 100 * (RPE - 1)$$

The % RPE value (deviation of the average penetration efficiency of the control) is used to determine the susceptibility of cells transfected with pNAox-dsRNA (FIG. 1).

In the case of the control dsRNA, five different experiments reveal no difference between the transfection with the control dsRNA and water with regard to the penetration efficiency of Bgh.

To rule out an effect of the dsRNA and the transformation rate or survival rate of the attacked cells, the number of GFP-expressing cells in control experiments and pNAox-dsRNA experiments was compared. The pNAox-dsRNA had no effect on the total number or the number of the attacked GFP-expressing cells.

EXAMPLE 5

NADPH Oxidase Inhibition with Diphenyleneiodonium Chloride

The results were supported by further experiments with the NADPH oxidase inhibitor diphenyleneiodonium chloride (DPI; table 1). In general, the experiments were carried out as described by Hückelhoven and Kogel, 1998.

TABLE 1

Effect of DPI on the defense against pathogens in Pallas[a]

| Type of interaction | Interactions (% ± standard error) | |
|---|---|---|
| | Control[b] | 200 μM DPI[c] |
| Penetration | 68.25 ± 9.9 | 16.25 ± 0.5 |
| Nonpenetration | 24.25 ± 6.3 | 67.5 ± 9.5 |
| HR (Hypersensitive response) | 7.5 ± 3.7 | 16.25 ± 9.3 |

[a]The DPI treatment was carried out 12 hours after inoculation with the pathogen and the evaluation 36 hours after inoculation.
[b]Controll with 10 mM potassium phosphate buffer, pH 7.8, with DMSO content as in the DPI treatment.
[c]DPI dissolved in 10 mM potassium phosphate buffer, pH 7.8, starting from a 10 mg/ml DPI stock solution in DMSO.

We claim:

1. A method of generating or increasing a resistance to at least one pathogen in plants, which comprises:

a) reducing an amount, activity or function of an NADPH oxidase in a plant or a tissue, organ, part or cell thereof, and b) selecting plants in which, in comparison with corresponding wild type plants the resistance to at least one pathogen exists or is increased, wherein the reducing of step (a) comprises introducing into the plant, tissue, organ, part or cell thereof a nucleic acid encoding a double-stranded RNA of NADPH oxidase, and wherein the NADPH oxidase comprises:

i) the polypeptide sequence as shown in SEQ ID NO: 2, 4, 6, 8, 10, 12, 14, 16, 18, 20 or 22, ii) a polypeptide sequence having at least 90% homology with the polypeptide sequence as shown in SEQ ID NO: 2, 4, 6, 8, 10, 12, 14, 16, 18, 20 or 22 and having the same function as the polypeptide sequence as shown in SEQ ID NO: 2, 4, 6, 8, 10, 12, 14, 16, 18, 20 or 22, iii) a polypeptide sequence encoded by the nucleic acid sequence as shown in SEQ ID NO: 1, 3, 5, 7, 9, 11, 13, 15, 17, 19 or 21, or iv) a polypeptide sequence encoded by a nucleic acid sequence having at least 90% homology with the nucleic acid sequence as shown in SEQ ID NO: 1, 3, 5, 7, 9, 11, 13, 15, 17, 19 or 21 and having the same function as the polypeptide sequence as shown in SEQ ID NO: 2, 4, 6, 8, 10, 12, 14, 16, 18, 20 or 22.

2. The method according to claim 1, wherein the NADPH oxidase further comprises at least one sequence motif selected from the group consisting of:

i) AL(K/R)GL(K/R) (SEQ ID NO: 25), ii) DK(N/D)XDG(R/K)(I/L/V)(T/N)E (SEQ ID NO: 26), iii) LSASAN (SEQ ID NO: 27), iv) IMEELDP (SEQ ID NO: 28), v) K(F/L)NMA(I/L)(I/V)LXPVCRN (SEQ ID NO: 29), vi) (E/Q)WHPFSIT (SEQ ID NO: 30), vii) S(A/S)PXDD(Q/Y)(L/I)S(IN)H(V/1/L)R (SEQ ID NO: 31), viii) DGPYG(S/A)PAGDY (SEQ ID NO: 32), ix) L(I/V)GLGIGATP (SEQ ID NO: 33), x) FYWVTREQGSF (SEQ ID NO: 34), and xi) GVFYCG (SEQ ID NO: 35).

3. The method according to claim 1, wherein the NADPH oxidase comprises a polypeptide sequence having at least 95% homology with the polypeptide as shown in SEQ ID NO: 2, 4, 6, 8, 10, 12, 14, 16, 18, 20 or 22 and having the same function as the polypeptide sequence as shown in SEQ ID NO: 2, 4, 6, 8, 10, 12, 14, 16, 18, 20 or 22.

4. The method according to claim 1, 2 or 3, wherein the reduction of the protein quantity, activity or function of an NADPH oxidase comprises introducing a double-stranded NADPH oxidase RNA nucleic acid sequence or an expression cassette comprising a nucleic acid sequence encoding said double-stranded NADPH oxidase RNA.

5. The method according to claim 1, 2 or 3, comprising (i) stably transforming a plant cell with a recombinant expression cassette comprising, in functional linkage with a promoter which is active in plants, a nucleic acid sequence encoding a double-stranded NADPH oxidase RNA ribonucleic acid sequence, (ii) regenerating a plant from the plant cell, and (iii) expressing said nucleic acid sequence in such a quantity and for such a time as suffices for generating or increasing a pathogen resistance in said plant.

6. The method according to claim 1, 2 or 3, wherein the pathogen is selected from the group consisting of bacteria, fungi, insects, viruses and nematodes.

7. The method according to claim 1, 2 or 3, wherein the pathogen is selected from the group consisting of Plasmodiophoramycota, Oomycota, Ascomycota, Chytridiomycetes, Zygomycetes, Basidiomycota and Deuteromyceten.

8. The method according to claim 1, 2 or 3, wherein the plant is selected from the group consisting of monocotyledonous and dicotyledonous plants.

9. The method according to claim 1, 2 or 3, wherein the plant is selected from the group consisting of wheat, oats, millet, barley, rye, maize, rice, buckwheat, sorghum, triticale, spelt, linseed and sugar cane.

10. A double-stranded RNA molecule for reducing the expression of an NADPH oxidase protein comprising:

a) a sense RNA strand comprising at least one ribonucleotide sequence which is essentially identical to at least part of the sense RNA transcript of a nucleic acid sequence encoding an NADPH oxidase, and b) an antisense RNA strand which is essentially complementary to the sense RNA strand of a), wherein the NADPH oxidase comprises:

i) the polypeptide sequence as shown in SEQ ID NO: 2, 4, 6, 8, 10, 12, 14, 16, 18, 20 or 22, ii) a polypeptide sequence having at least 90% homology with the polypeptide sequence as shown in SEQ ID NO: 2, 4, 6, 8, 10, 12, 14, 16, 18, 20 or 22 and having the same function as the polypeptide sequence as shown in SEQ ID NO: 2, 4, 6, 8, 10, 12, 14, 16, 18, 20 or 22, iii) a polypeptide sequence encoded by the nucleic acid sequence as shown in SEQ ID NO: 1, 3, 5, 7, 9, 11, 13, 15, 17, 19 or 21, or iv) a polypeptide sequence encoded by a nucleic acid sequence having at least 90% homology with the nucleic acid sequence as shown in SEQ ID NO: 1, 3, 5, 7, 9, 11, 13, 15, 17, 19 or 21 and having the same function as the polypeptide sequence as shown in SEQ ID NO: 2, 4, 6, 8, 10, 12, 14, 16, 18, 20 or 22.

11. The double-stranded RNA molecule according to claim 10, wherein the two RNA strands of the double-stranded RNA are bonded covalently with one another.

12. The double-stranded RNA molecule according to claim 10, wherein one of the two RNA strands is encoded by a nucleic acid sequence encoding an NADPH oxidase, wherein the nucleic acid sequence comprises SEQ ID NO: 1, 3, 5, 7, 9, 11, 13, 15, 17, 19 or 21.

13. An expression cassette comprising, in functional linkage with a promoter which is functional in a plant, a nucleic acid sequence encoding the double-stranded RNA molecule according to claim 10, 11 or 12.

14. The expression cassette according to claim 13, wherein the promoter which is functional in plants is a pathogen-inducible promoter.

15. A vector comprising the expression cassette according to claim 13.

16. A transgenic plant cell, plant or parts thereof, comprising the double-stranded RNA molecule according to claim 10 or 11, an expression cassette comprising, in functional linkage with a promoter which is functional in plant organisms, a nucleic acid encoding said double-stranded RNA molecule or a vector comprising said expression cassette.

17. The transgenic plant cell, plant or parts thereof according to claim 16, wherein the plant is selected from the group consisting of wheat, oats, millet, barley, rye, maize, rice, buckwheat, sorghum, triticale, spelt, linseed, sugar cane, oilseed rape, canola, cress, Arabidopsis, cabbages, soybeans, alfalfa, pea, beans, peanut, potato, tobacco, tomato, egg plant, capsicum, sunflower, Tagetes, lettuce, Calendula, melon, pumpkin/squash and zucchini.

18. A transgenic tissue, organ, part, cell, cell culture or propagation material derived from the transgenic plant cell, plant or parts thereof according to claim 17.

19. The method according to claim 4, comprising:

(i) stably transforming a plant cell with a recombinant expression cassette comprising, in functional linkage with a promoter which is active in plants, a nucleic acid sequence encoding a double-stranded NADPH oxidase RNA ribonucleic acid sequence, (ii) regenerating a plant from the plant cell, and (iii) expressing said nucleic acid sequence in such a quantity and for such a time as suffices for generating or increasing a pathogen resistance in said plant.

20. The method of claim 1, wherein the NADPH oxidase comprises the polypeptide sequence as shown in SEQ ID NO: 2, 4, 6, 8, 10, 12, 14, 16, 18, 20 or 22.

21. The method of claim 1, wherein the NADPH oxidase comprises a polypeptide sequence encoded by the nucleic acid sequence as shown in SEQ ID NO: 1, 3, 5, 7, 9, 11, 13, 15, 17, 19 or 21.

22. The double-stranded RNA molecule of claim 10, wherein the NADPH oxidase comprises the polypeptide sequence as shown in SEQ ID NO: 2, 4, 6, 8, 10, 12, 14, 16, 18, 20 or 22.

23. The double-stranded RNA molecule of claim 10, wherein the NADPH oxidase comprises a polypeptide sequence encoded by the nucleic acid sequence as shown in SEQ ID NO: 1, 3, 5, 7, 9, 11, 13, 15, 17, 19 or 21.

* * * * *

SEQUENCE LISTING

```
<160> NUMBER OF SEQ ID NOS: 36

<210> SEQ ID NO 1
<211> LENGTH: 337
<212> TYPE: DNA
<213> ORGANISM: Hordeum vulgare
<220> FEATURE:
<221> NAME/KEY: CDS
<222> LOCATION: (2)..(337)
<223> OTHER INFORMATION: coding for NADPH oxidase (fragment)

<400> SEQUENCE: 1

g ttt aaa gga atc atg aat gag att gct gaa cta gat caa agg aat atc      49
  Phe Lys Gly Ile Met Asn Glu Ile Ala Glu Leu Asp Gln Arg Asn Ile
    1               5                  10                  15

att gag atg cac aac tat ctc aca agt gtt tat gag gaa ggg gat gct        97
Ile Glu Met His Asn Tyr Leu Thr Ser Val Tyr Glu Glu Gly Asp Ala
            20                  25                  30

cgg tca gca ctc atc aca atg ctg caa gct ctc aac cat gcc aag aat       145
Arg Ser Ala Leu Ile Thr Met Leu Gln Ala Leu Asn His Ala Lys Asn
        35                  40                  45

ggt gtc gat gta gtg tct ggm act cga gtc cgg aca cat ttt gca aga       193
Gly Val Asp Val Val Ser Xaa Thr Arg Val Arg Thr His Phe Ala Arg
    50                  55                  60

cca aat ttt aag agg gtg ctg tct aag gta gcc gcc aaa cat cct tat       241
Pro Asn Phe Lys Arg Val Leu Ser Lys Val Ala Ala Lys His Pro Tyr
65                  70                  75                  80

gcc aag ata gga gtg ttc tat tgc gga gct cca gtt ctg gcg cag gaa       289
Ala Lys Ile Gly Val Phe Tyr Cys Gly Ala Pro Val Leu Ala Gln Glu
                85                  90                  95

cta agc aac ctt tgc cat gag ttc aat ggc aaa tgc acg aca aaa ttc       337
Leu Ser Asn Leu Cys His Glu Phe Asn Gly Lys Cys Thr Thr Lys Phe
            100                 105                 110


<210> SEQ ID NO 2
<211> LENGTH: 112
<212> TYPE: PRT
<213> ORGANISM: Hordeum vulgare
<220> FEATURE:
<221> NAME/KEY: misc_feature
<222> LOCATION: (55)..(55)
<223> OTHER INFORMATION: The 'Xaa' at location 55 stands for Gly.

<400> SEQUENCE: 2

Phe Lys Gly Ile Met Asn Glu Ile Ala Glu Leu Asp Gln Arg Asn Ile
1               5                   10                  15

Ile Glu Met His Asn Tyr Leu Thr Ser Val Tyr Glu Glu Gly Asp Ala
            20                  25                  30
```

```
Arg Ser Ala Leu Ile Thr Met Leu Gln Ala Leu Asn His Ala Lys Asn
        35                  40                  45

Gly Val Asp Val Val Ser Xaa Thr Arg Val Arg Thr His Phe Ala Arg
    50                  55                  60

Pro Asn Phe Lys Arg Val Leu Ser Lys Val Ala Ala Lys His Pro Tyr
65                  70                  75                  80

Ala Lys Ile Gly Val Phe Tyr Cys Gly Ala Pro Val Leu Ala Gln Glu
                85                  90                  95

Leu Ser Asn Leu Cys His Glu Phe Asn Gly Lys Cys Thr Thr Lys Phe
            100                 105                 110


<210> SEQ ID NO 3
<211> LENGTH: 2832
<212> TYPE: DNA
<213> ORGANISM: Oryza sativa
<220> FEATURE:
<221> NAME/KEY: CDS
<222> LOCATION: (1)..(2829)
<223> OTHER INFORMATION: coding for NADPH oxidase

<400> SEQUENCE: 3

atg agg ggc ggc gcc tcc tcg gga ccc cag cga tgg ggc tcg gcg ggg       48
Met Arg Gly Gly Ala Ser Ser Gly Pro Gln Arg Trp Gly Ser Ala Gly
  1               5                  10                  15

acg aca ccg cgg tcg ctg agc acg ggc tcg tcg ccg cgc ggg tcc gac       96
Thr Thr Pro Arg Ser Leu Ser Thr Gly Ser Ser Pro Arg Gly Ser Asp
            20                  25                  30

gac cgg agc tcc gac gac ggg gag gag ctg gtc gag gtc acg ctc gac      144
Asp Arg Ser Ser Asp Asp Gly Glu Glu Leu Val Glu Val Thr Leu Asp
        35                  40                  45

ctg cag gac gac gac acc att gtg ctt cgg agc gtc gag ccc gcg gcg      192
Leu Gln Asp Asp Asp Thr Ile Val Leu Arg Ser Val Glu Pro Ala Ala
    50                  55                  60

gcg gcg gcg gcg ggg gtg ggg gcg ggg gcg ggg gcg gcg tcg gcg cgg      240
Ala Ala Ala Ala Gly Val Gly Ala Gly Ala Gly Ala Ala Ser Ala Arg
65                  70                  75                  80

ggg gag ctc acg ggt ggc ccg tcg tcg tcg tcg tcg cgg tcg agg tcg      288
Gly Glu Leu Thr Gly Gly Pro Ser Ser Ser Ser Ser Arg Ser Arg Ser
                85                  90                  95

ccg tcg atc cgg agg agc tcg tcg cac cgg ctg ctg cag ttc tcg cag      336
Pro Ser Ile Arg Arg Ser Ser Ser His Arg Leu Leu Gln Phe Ser Gln
            100                 105                 110

gag ctc aag gcg gag gcc atg gcc cgg gcg cgg cag ttc tcg cag gac      384
Glu Leu Lys Ala Glu Ala Met Ala Arg Ala Arg Gln Phe Ser Gln Asp
        115                 120                 125

ctg acc aag cgg ttc ggc cgc agc cac agc cgc agc gaa gcg cag gcg      432
Leu Thr Lys Arg Phe Gly Arg Ser His Ser Arg Ser Glu Ala Gln Ala
    130                 135                 140

ccg tcg ggc ctc gag tcc gcg ctc gcc gcc cgc gcc gcg cgg cgg cag      480
Pro Ser Gly Leu Glu Ser Ala Leu Ala Ala Arg Ala Ala Arg Arg Gln
145                 150                 155                 160

cgc gcg cag ctc gac cgc aca cgc tcc ggc gcc cac aag gcg ctc cgc      528
Arg Ala Gln Leu Asp Arg Thr Arg Ser Gly Ala His Lys Ala Leu Arg
                165                 170                 175

ggc ctc cgc ttc atc agc agc aac aag gcc aac aac gcc tgg atg gag      576
Gly Leu Arg Phe Ile Ser Ser Asn Lys Ala Asn Asn Ala Trp Met Glu
            180                 185                 190

gtg cag gcc aac ttc gac cgc ctc gcc cgc gac ggc tac ctc tcc cgc      624
Val Gln Ala Asn Phe Asp Arg Leu Ala Arg Asp Gly Tyr Leu Ser Arg
        195                 200                 205
```

```
tcc gac ttc gcc gaa tgc atc ggg atg acg gaa tcg aag gag ttc gcg      672
Ser Asp Phe Ala Glu Cys Ile Gly Met Thr Glu Ser Lys Glu Phe Ala
    210                 215                 220

ctc gag ctg ttc gac acg ctg agc cgg cga cga cag atg aag gtg gac      720
Leu Glu Leu Phe Asp Thr Leu Ser Arg Arg Arg Gln Met Lys Val Asp
225                 230                 235                 240

acg att aac aag gat gaa ctc cgc gag atc tgg cag cag atc acc gat      768
Thr Ile Asn Lys Asp Glu Leu Arg Glu Ile Trp Gln Gln Ile Thr Asp
                245                 250                 255

aac agc ttc gac tcc cgt ctc caa atc ttc ttc gaa atg gtg gat aag      816
Asn Ser Phe Asp Ser Arg Leu Gln Ile Phe Phe Glu Met Val Asp Lys
            260                 265                 270

aac gcg gac ggc cgg att acg gag gcg gag gtg aaa gag att att atg      864
Asn Ala Asp Gly Arg Ile Thr Glu Ala Glu Val Lys Glu Ile Ile Met
        275                 280                 285

ttg agc gcg tct gcc aat aaa ctg tcg agg ctt aag gag caa gca gaa      912
Leu Ser Ala Ser Ala Asn Lys Leu Ser Arg Leu Lys Glu Gln Ala Glu
    290                 295                 300

gag tac gcc gct ttg atc atg gag gag ctt gat cct gaa ggg ctc ggc      960
Glu Tyr Ala Ala Leu Ile Met Glu Glu Leu Asp Pro Glu Gly Leu Gly
305                 310                 315                 320

tac att gag cta tgg caa ttg gag aca ctt ctg ttg cag aaa gat acc     1008
Tyr Ile Glu Leu Trp Gln Leu Glu Thr Leu Leu Leu Gln Lys Asp Thr
                325                 330                 335

tat atg aac tat agt cag gcc ctt agt tac aca agc caa gca ctg agc     1056
Tyr Met Asn Tyr Ser Gln Ala Leu Ser Tyr Thr Ser Gln Ala Leu Ser
            340                 345                 350

cag aat ctt gca ggg cta agg aag aag agt tca atc cgc aaa ata agc     1104
Gln Asn Leu Ala Gly Leu Arg Lys Lys Ser Ser Ile Arg Lys Ile Ser
        355                 360                 365

acc tct tta agc tac tat ttc gag gac aac tgg aaa cgt tta tgg gtg     1152
Thr Ser Leu Ser Tyr Tyr Phe Glu Asp Asn Trp Lys Arg Leu Trp Val
    370                 375                 380

ctt gca ttg tgg att ggg ata atg gct gga ctg ttc acc tgg aaa ttc     1200
Leu Ala Leu Trp Ile Gly Ile Met Ala Gly Leu Phe Thr Trp Lys Phe
385                 390                 395                 400

atg cag tat cgt aac cga tat gtc ttt gat gtg atg ggc tac tgt gtc     1248
Met Gln Tyr Arg Asn Arg Tyr Val Phe Asp Val Met Gly Tyr Cys Val
                405                 410                 415

aca aca gca aaa gga gct gct gaa acc cta aag ctg aat atg gca att     1296
Thr Thr Ala Lys Gly Ala Ala Glu Thr Leu Lys Leu Asn Met Ala Ile
            420                 425                 430

atc ctc ctg cca gta tgc cgt aac acc att act tgg ttg cga agt aca     1344
Ile Leu Leu Pro Val Cys Arg Asn Thr Ile Thr Trp Leu Arg Ser Thr
        435                 440                 445

agg gct gca cgg gca cta cct ttt gat gac aac atc aac ttc cac aag     1392
Arg Ala Ala Arg Ala Leu Pro Phe Asp Asp Asn Ile Asn Phe His Lys
    450                 455                 460

act att gca gca gca att gtg gtt ggt ata atc ctc cat gca ggg aac     1440
Thr Ile Ala Ala Ala Ile Val Val Gly Ile Ile Leu His Ala Gly Asn
465                 470                 475                 480

cac ctt gta tgc gat ttt cca cgg tta ata aaa tca tca gat gag aag     1488
His Leu Val Cys Asp Phe Pro Arg Leu Ile Lys Ser Ser Asp Glu Lys
                485                 490                 495

tat gct cct ttg ggc cag tat ttt ggg gaa ata aag cca aca tat ttt     1536
Tyr Ala Pro Leu Gly Gln Tyr Phe Gly Glu Ile Lys Pro Thr Tyr Phe
            500                 505                 510

aca ttg gtc aaa gga gtg gag ggc atc act ggg gta atc atg gtt gta     1584
Thr Leu Val Lys Gly Val Glu Gly Ile Thr Gly Val Ile Met Val Val
        515                 520                 525
```

-continued

```
tgc atg ata att gct ttt act cta gca acc cgg tgg ttc cgc cgt agc      1632
Cys Met Ile Ile Ala Phe Thr Leu Ala Thr Arg Trp Phe Arg Arg Ser
    530                 535                 540

ttg gtt aag ctt cca agg cca ttt gac aaa ctg act ggc ttc aat gcc      1680
Leu Val Lys Leu Pro Arg Pro Phe Asp Lys Leu Thr Gly Phe Asn Ala
545                 550                 555                 560

ttt tgg tat tct cat cat ctg ttc atc att gtg tat atc gcg ctc att      1728
Phe Trp Tyr Ser His His Leu Phe Ile Ile Val Tyr Ile Ala Leu Ile
                565                 570                 575

gtt cat gga gag tgt cta tac ctt att cat gtc tgg tac aga aga acg      1776
Val His Gly Glu Cys Leu Tyr Leu Ile His Val Trp Tyr Arg Arg Thr
            580                 585                 590

aca tgg atg tat ctt tca gtg cct gtt tgc ttg tat gta ggg gag agg      1824
Thr Trp Met Tyr Leu Ser Val Pro Val Cys Leu Tyr Val Gly Glu Arg
        595                 600                 605

att cta agg ttc ttc agg tct ggc agt tat tct gtc cgg cta ttg aag      1872
Ile Leu Arg Phe Phe Arg Ser Gly Ser Tyr Ser Val Arg Leu Leu Lys
    610                 615                 620

gtg gcc ata tat cca ggt aat gtt ttg aca ctg caa atg tcc aag cct      1920
Val Ala Ile Tyr Pro Gly Asn Val Leu Thr Leu Gln Met Ser Lys Pro
625                 630                 635                 640

ccc acg ttc cgt tac aag agt gga caa tat atg ttt gtt caa tgt cca      1968
Pro Thr Phe Arg Tyr Lys Ser Gly Gln Tyr Met Phe Val Gln Cys Pro
                645                 650                 655

gca gtg tct ccc ttt gaa tgg cat ccc ttc tca att act tca gca cct      2016
Ala Val Ser Pro Phe Glu Trp His Pro Phe Ser Ile Thr Ser Ala Pro
            660                 665                 670

ggg gat gac tac ctc agc att cat gtt cga caa ctt ggt gat tgg aca      2064
Gly Asp Asp Tyr Leu Ser Ile His Val Arg Gln Leu Gly Asp Trp Thr
        675                 680                 685

cga gaa ctc aag aga gta ttt gct gca gct tgt gag ccc cca gcg ggt      2112
Arg Glu Leu Lys Arg Val Phe Ala Ala Ala Cys Glu Pro Pro Ala Gly
    690                 695                 700

ggt aaa agc ggc ctt ctt agg gca gat gag aca act aag aaa atc tta      2160
Gly Lys Ser Gly Leu Leu Arg Ala Asp Glu Thr Thr Lys Lys Ile Leu
705                 710                 715                 720

ccc aag ctt ctg att gat gga ccg tat ggt tct cct gct cag gat tac      2208
Pro Lys Leu Leu Ile Asp Gly Pro Tyr Gly Ser Pro Ala Gln Asp Tyr
                725                 730                 735

agc aag tat gat gtt tta tta ctt gtt gga tta gga att ggt gcg aca      2256
Ser Lys Tyr Asp Val Leu Leu Leu Val Gly Leu Gly Ile Gly Ala Thr
            740                 745                 750

ccc ttt att agc ata tta aaa gat ctt ctg aat aac atc atc aaa atg      2304
Pro Phe Ile Ser Ile Leu Lys Asp Leu Leu Asn Asn Ile Ile Lys Met
        755                 760                 765

gag gaa gag gag gat gct tct act gat ctt tat cca cca atg ggt cgg      2352
Glu Glu Glu Glu Asp Ala Ser Thr Asp Leu Tyr Pro Pro Met Gly Arg
    770                 775                 780

aat aag cca cat gtt gat ctg ggc aca ctt atg acg att acc tca aga      2400
Asn Lys Pro His Val Asp Leu Gly Thr Leu Met Thr Ile Thr Ser Arg
785                 790                 795                 800

cca aag aag atc ttg aag acc aca aat gct tac ttt tac tgg gtg aca      2448
Pro Lys Lys Ile Leu Lys Thr Thr Asn Ala Tyr Phe Tyr Trp Val Thr
                805                 810                 815

cgt gag caa ggc tct ttt gat tgg ttc aaa gga gtc atg aat gaa att      2496
Arg Glu Gln Gly Ser Phe Asp Trp Phe Lys Gly Val Met Asn Glu Ile
            820                 825                 830

gct gac ttg gat caa agg aat atc att gag atg cac aac tac cta aca      2544
Ala Asp Leu Asp Gln Arg Asn Ile Ile Glu Met His Asn Tyr Leu Thr
        835                 840                 845
```

```
agc gtc tat gag gag ggg gat gcc agg tca gca ctc atc acc atg ctc      2592
Ser Val Tyr Glu Glu Gly Asp Ala Arg Ser Ala Leu Ile Thr Met Leu
    850                 855                 860

caa gct ctg aac cat gcc aag aat gga gtt gat att gtc tct ggg aca      2640
Gln Ala Leu Asn His Ala Lys Asn Gly Val Asp Ile Val Ser Gly Thr
865                 870                 875                 880

aaa gtc cgg aca cat ttt gca cga cca aat tgg aga aag gtc ctt tct      2688
Lys Val Arg Thr His Phe Ala Arg Pro Asn Trp Arg Lys Val Leu Ser
                885                 890                 895

aaa att tcc tcc aag cat cca tat gcc aaa ata ggt gta ttc tac tgt      2736
Lys Ile Ser Ser Lys His Pro Tyr Ala Lys Ile Gly Val Phe Tyr Cys
            900                 905                 910

gga gct cca gtc ctg gca caa gaa cta agc aaa ctt tgc cat gaa ttc      2784
Gly Ala Pro Val Leu Ala Gln Glu Leu Ser Lys Leu Cys His Glu Phe
        915                 920                 925

aac ggg aaa tgc aca acg aag ttc gaa ttc cat aag gag cat ttc tga      2832
Asn Gly Lys Cys Thr Thr Lys Phe Glu Phe His Lys Glu His Phe
    930                 935                 940


<210> SEQ ID NO 4
<211> LENGTH: 943
<212> TYPE: PRT
<213> ORGANISM: Oryza sativa

<400> SEQUENCE: 4

Met Arg Gly Gly Ala Ser Ser Gly Pro Gln Arg Trp Gly Ser Ala Gly
  1               5                  10                  15

Thr Thr Pro Arg Ser Leu Ser Thr Gly Ser Ser Pro Arg Gly Ser Asp
            20                  25                  30

Asp Arg Ser Ser Asp Asp Gly Glu Glu Leu Val Glu Val Thr Leu Asp
        35                  40                  45

Leu Gln Asp Asp Asp Thr Ile Val Leu Arg Ser Val Glu Pro Ala Ala
    50                  55                  60

Ala Ala Ala Ala Gly Val Gly Ala Gly Ala Gly Ala Ala Ser Ala Arg
 65                  70                  75                  80

Gly Glu Leu Thr Gly Gly Pro Ser Ser Ser Ser Ser Arg Ser Arg Ser
                85                  90                  95

Pro Ser Ile Arg Arg Ser Ser Ser His Arg Leu Leu Gln Phe Ser Gln
            100                 105                 110

Glu Leu Lys Ala Glu Ala Met Ala Arg Ala Arg Gln Phe Ser Gln Asp
        115                 120                 125

Leu Thr Lys Arg Phe Gly Arg Ser His Ser Arg Ser Glu Ala Gln Ala
    130                 135                 140

Pro Ser Gly Leu Glu Ser Ala Leu Ala Ala Arg Ala Ala Arg Arg Gln
145                 150                 155                 160

Arg Ala Gln Leu Asp Arg Thr Arg Ser Gly Ala His Lys Ala Leu Arg
                165                 170                 175

Gly Leu Arg Phe Ile Ser Ser Asn Lys Ala Asn Asn Ala Trp Met Glu
            180                 185                 190

Val Gln Ala Asn Phe Asp Arg Leu Ala Arg Asp Gly Tyr Leu Ser Arg
        195                 200                 205

Ser Asp Phe Ala Glu Cys Ile Gly Met Thr Glu Ser Lys Glu Phe Ala
    210                 215                 220

Leu Glu Leu Phe Asp Thr Leu Ser Arg Arg Arg Gln Met Lys Val Asp
225                 230                 235                 240

Thr Ile Asn Lys Asp Glu Leu Arg Glu Ile Trp Gln Gln Ile Thr Asp
                245                 250                 255
```

```
Asn Ser Phe Asp Ser Arg Leu Gln Ile Phe Phe Glu Met Val Asp Lys
            260                 265                 270

Asn Ala Asp Gly Arg Ile Thr Glu Ala Glu Val Lys Glu Ile Ile Met
        275                 280                 285

Leu Ser Ala Ser Ala Asn Lys Leu Ser Arg Leu Lys Glu Gln Ala Glu
    290                 295                 300

Glu Tyr Ala Ala Leu Ile Met Glu Glu Leu Asp Pro Glu Gly Leu Gly
305                 310                 315                 320

Tyr Ile Glu Leu Trp Gln Leu Glu Thr Leu Leu Leu Gln Lys Asp Thr
                325                 330                 335

Tyr Met Asn Tyr Ser Gln Ala Leu Ser Tyr Thr Ser Gln Ala Leu Ser
            340                 345                 350

Gln Asn Leu Ala Gly Leu Arg Lys Lys Ser Ser Ile Arg Lys Ile Ser
        355                 360                 365

Thr Ser Leu Ser Tyr Tyr Phe Glu Asp Asn Trp Lys Arg Leu Trp Val
    370                 375                 380

Leu Ala Leu Trp Ile Gly Ile Met Ala Gly Leu Phe Thr Trp Lys Phe
385                 390                 395                 400

Met Gln Tyr Arg Asn Arg Tyr Val Phe Asp Val Met Gly Tyr Cys Val
                405                 410                 415

Thr Thr Ala Lys Gly Ala Ala Glu Thr Leu Lys Leu Asn Met Ala Ile
            420                 425                 430

Ile Leu Leu Pro Val Cys Arg Asn Thr Ile Thr Trp Leu Arg Ser Thr
        435                 440                 445

Arg Ala Ala Arg Ala Leu Pro Phe Asp Asp Asn Ile Asn Phe His Lys
    450                 455                 460

Thr Ile Ala Ala Ala Ile Val Val Gly Ile Ile Leu His Ala Gly Asn
465                 470                 475                 480

His Leu Val Cys Asp Phe Pro Arg Leu Ile Lys Ser Ser Asp Glu Lys
                485                 490                 495

Tyr Ala Pro Leu Gly Gln Tyr Phe Gly Glu Ile Lys Pro Thr Tyr Phe
            500                 505                 510

Thr Leu Val Lys Gly Val Glu Gly Ile Thr Gly Val Ile Met Val Val
        515                 520                 525

Cys Met Ile Ile Ala Phe Thr Leu Ala Thr Arg Trp Phe Arg Arg Ser
    530                 535                 540

Leu Val Lys Leu Pro Arg Pro Phe Asp Lys Leu Thr Gly Phe Asn Ala
545                 550                 555                 560

Phe Trp Tyr Ser His His Leu Phe Ile Ile Val Tyr Ile Ala Leu Ile
                565                 570                 575

Val His Gly Glu Cys Leu Tyr Leu Ile His Val Trp Tyr Arg Arg Thr
            580                 585                 590

Thr Trp Met Tyr Leu Ser Val Pro Val Cys Leu Tyr Val Gly Glu Arg
        595                 600                 605

Ile Leu Arg Phe Phe Arg Ser Gly Ser Tyr Ser Val Arg Leu Leu Lys
    610                 615                 620

Val Ala Ile Tyr Pro Gly Asn Val Leu Thr Leu Gln Met Ser Lys Pro
625                 630                 635                 640

Pro Thr Phe Arg Tyr Lys Ser Gly Gln Tyr Met Phe Val Gln Cys Pro
                645                 650                 655

Ala Val Ser Pro Phe Glu Trp His Pro Phe Ser Ile Thr Ser Ala Pro
            660                 665                 670

Gly Asp Asp Tyr Leu Ser Ile His Val Arg Gln Leu Gly Asp Trp Thr
        675                 680                 685
```

```
Arg Glu Leu Lys Arg Val Phe Ala Ala Ala Cys Glu Pro Pro Ala Gly
    690                 695                 700

Gly Lys Ser Gly Leu Leu Arg Ala Asp Glu Thr Thr Lys Lys Ile Leu
705                 710                 715                 720

Pro Lys Leu Leu Ile Asp Gly Pro Tyr Gly Ser Pro Ala Gln Asp Tyr
                725                 730                 735

Ser Lys Tyr Asp Val Leu Leu Leu Val Gly Leu Gly Ile Gly Ala Thr
            740                 745                 750

Pro Phe Ile Ser Ile Leu Lys Asp Leu Leu Asn Asn Ile Ile Lys Met
        755                 760                 765

Glu Glu Glu Glu Asp Ala Ser Thr Asp Leu Tyr Pro Pro Met Gly Arg
    770                 775                 780

Asn Lys Pro His Val Asp Leu Gly Thr Leu Met Thr Ile Thr Ser Arg
785                 790                 795                 800

Pro Lys Lys Ile Leu Lys Thr Thr Asn Ala Tyr Phe Tyr Trp Val Thr
                805                 810                 815

Arg Glu Gln Gly Ser Phe Asp Trp Phe Lys Gly Val Met Asn Glu Ile
            820                 825                 830

Ala Asp Leu Asp Gln Arg Asn Ile Ile Glu Met His Asn Tyr Leu Thr
        835                 840                 845

Ser Val Tyr Glu Glu Gly Asp Ala Arg Ser Ala Leu Ile Thr Met Leu
    850                 855                 860

Gln Ala Leu Asn His Ala Lys Asn Gly Val Asp Ile Val Ser Gly Thr
865                 870                 875                 880

Lys Val Arg Thr His Phe Ala Arg Pro Asn Trp Arg Lys Val Leu Ser
                885                 890                 895

Lys Ile Ser Ser Lys His Pro Tyr Ala Lys Ile Gly Val Phe Tyr Cys
            900                 905                 910

Gly Ala Pro Val Leu Ala Gln Glu Leu Ser Lys Leu Cys His Glu Phe
        915                 920                 925

Asn Gly Lys Cys Thr Thr Lys Phe Glu Phe His Lys Glu His Phe
    930                 935                 940


<210> SEQ ID NO 5
<211> LENGTH: 2889
<212> TYPE: DNA
<213> ORGANISM: Nicotiana tabacum
<220> FEATURE:
<221> NAME/KEY: CDS
<222> LOCATION: (1)..(2886)
<223> OTHER INFORMATION: coding for NADPH oxidase

<400> SEQUENCE: 5

atg agg ggt tta cct ggg cat gaa cgc cgg tgg aca tcc gat acg gta       48
Met Arg Gly Leu Pro Gly His Glu Arg Arg Trp Thr Ser Asp Thr Val
  1               5                  10                  15

tct tcc gac aag gat ttt agt ggt gaa tta tcg ccg gga gct gat tcc       96
Ser Ser Asp Lys Asp Phe Ser Gly Glu Leu Ser Pro Gly Ala Asp Ser
             20                  25                  30

ggc tat aat tcc ggt ttt gct tcc gag gag ttt gtt gaa gtc acg ctt      144
Gly Tyr Asn Ser Gly Phe Ala Ser Glu Glu Phe Val Glu Val Thr Leu
         35                  40                  45

gat ctt cag gat gat gat acc att att cta cgg agc gtt gaa ccg gct      192
Asp Leu Gln Asp Asp Asp Thr Ile Ile Leu Arg Ser Val Glu Pro Ala
     50                  55                  60

act gtg att aac att gac gct cct gat ctt ccc gcc gga gtc ggt att      240
Thr Val Ile Asn Ile Asp Ala Pro Asp Leu Pro Ala Gly Val Gly Ile
 65                  70                  75                  80
```

```
tcc gga gtt tca att gaa act ccg acg tca gca tcg gtg tcg gaa tct      288
Ser Gly Val Ser Ile Glu Thr Pro Thr Ser Ala Ser Val Ser Glu Ser
                 85                  90                  95

cga tcg ccg acg atc cgc cgg agt tca tct agt aaa ctt cgt cag ttt      336
Arg Ser Pro Thr Ile Arg Arg Ser Ser Ser Ser Lys Leu Arg Gln Phe
            100                 105                 110

tca cag gag ttg aaa gct gag gcg gtt gcg aaa gcg agg cag ttt tca      384
Ser Gln Glu Leu Lys Ala Glu Ala Val Ala Lys Ala Arg Gln Phe Ser
        115                 120                 125

caa gag ctg aag gcg gag tta agg aga ttc tca tgg agc cat ggg cat      432
Gln Glu Leu Lys Ala Glu Leu Arg Arg Phe Ser Trp Ser His Gly His
    130                 135                 140

gcg tct cgc gcg ttt tcg ccc tcg tcg ttt ttt caa aac gcc gtc gtt      480
Ala Ser Arg Ala Phe Ser Pro Ser Ser Phe Phe Gln Asn Ala Val Val
145                 150                 155                 160

gga aca ggt aac ggc gtg gac tcg gct tta gcg gca cgt gca tta cgt      528
Gly Thr Gly Asn Gly Val Asp Ser Ala Leu Ala Ala Arg Ala Leu Arg
                165                 170                 175

cgg caa cgc gcg cag ctt gat cgg act cgt tcc agc gcc cat aga gct      576
Arg Gln Arg Ala Gln Leu Asp Arg Thr Arg Ser Ser Ala His Arg Ala
            180                 185                 190

ctt cgt aga ctc aaa ttc att agc aat aac aaa acc aat gga tgg aat      624
Leu Arg Arg Leu Lys Phe Ile Ser Asn Asn Lys Thr Asn Gly Trp Asn
        195                 200                 205

gaa gtt gaa aac aat ttc tca aag ctc gct aaa gac ggt tat ctt tac      672
Glu Val Glu Asn Asn Phe Ser Lys Leu Ala Lys Asp Gly Tyr Leu Tyr
    210                 215                 220

cgt tcc gat ttc gca caa tgc ata ggt atg aag gat tcg aag gaa ttt      720
Arg Ser Asp Phe Ala Gln Cys Ile Gly Met Lys Asp Ser Lys Glu Phe
225                 230                 235                 240

gca ttg gaa tta ttt gat gct ttg agt aga aga aga aga tta aag gtt      768
Ala Leu Glu Leu Phe Asp Ala Leu Ser Arg Arg Arg Arg Leu Lys Val
                245                 250                 255

gat aaa att agc aag gag gaa ttg tat gag tac tgg tct caa atc acc      816
Asp Lys Ile Ser Lys Glu Glu Leu Tyr Glu Tyr Trp Ser Gln Ile Thr
            260                 265                 270

gat cag agt ttc gat tct cgg ctt cag atc tcc ttc gac atg gtg gac      864
Asp Gln Ser Phe Asp Ser Arg Leu Gln Ile Ser Phe Asp Met Val Asp
        275                 280                 285

aag aat gaa gat ggt cga att gct gaa gag gaa gta aaa gag atc atc      912
Lys Asn Glu Asp Gly Arg Ile Ala Glu Glu Glu Val Lys Glu Ile Ile
    290                 295                 300

atg cta agt gca tct gca aac aag tta tca aga tta aaa gaa caa gca      960
Met Leu Ser Ala Ser Ala Asn Lys Leu Ser Arg Leu Lys Glu Gln Ala
305                 310                 315                 320

gag gag tat gca gct tta atc atg gaa gaa tta gat cct gaa aga ctc     1008
Glu Glu Tyr Ala Ala Leu Ile Met Glu Glu Leu Asp Pro Glu Arg Leu
                325                 330                 335

ggc tac att gag cta tgg cag ctg gaa aca ctt ctc ctc caa aag gac     1056
Gly Tyr Ile Glu Leu Trp Gln Leu Glu Thr Leu Leu Leu Gln Lys Asp
            340                 345                 350

act tac ctc aac tac agt caa gca cta agt tac acg agc caa gcc ttg     1104
Thr Tyr Leu Asn Tyr Ser Gln Ala Leu Ser Tyr Thr Ser Gln Ala Leu
        355                 360                 365

agc caa aac ctt cac gga tta agg aag aaa agc cca ata aaa aga atg     1152
Ser Gln Asn Leu His Gly Leu Arg Lys Lys Ser Pro Ile Lys Arg Met
    370                 375                 380

agc aca aaa ctt gtc tat tca ttg caa gaa aac tgg aag aga att tgg     1200
Ser Thr Lys Leu Val Tyr Ser Leu Gln Glu Asn Trp Lys Arg Ile Trp
385                 390                 395                 400
```

```
gtt ctc act tta tgg att ttg ata atg att ggg ctt ttt ctt tgg aag     1248
Val Leu Thr Leu Trp Ile Leu Ile Met Ile Gly Leu Phe Leu Trp Lys
                405                 410                 415

ttc tat cag tac aaa aac aag agt gca ttc cgt gtc atg ggt tat tgc     1296
Phe Tyr Gln Tyr Lys Asn Lys Ser Ala Phe Arg Val Met Gly Tyr Cys
            420                 425                 430

ctt gtc acg gct aag ggc gct gct gag act ctc aag ttc aac atg gct     1344
Leu Val Thr Ala Lys Gly Ala Ala Glu Thr Leu Lys Phe Asn Met Ala
        435                 440                 445

ctt ata tta ttg cca gta tgc aga aac act att aca tgg ctc agg tcc     1392
Leu Ile Leu Leu Pro Val Cys Arg Asn Thr Ile Thr Trp Leu Arg Ser
    450                 455                 460

acc aag ttg agc cat ttt gta ccc ttt gac gac aac atc aac ttt cac     1440
Thr Lys Leu Ser His Phe Val Pro Phe Asp Asp Asn Ile Asn Phe His
465                 470                 475                 480

aag act gtc gct gca gcc att gtc act ggt atc ata ctc cat gct ggt     1488
Lys Thr Val Ala Ala Ala Ile Val Thr Gly Ile Ile Leu His Ala Gly
                485                 490                 495

aac cat ctt gta tgt gat ttc cca agg ctt ata cat gca gat gat caa     1536
Asn His Leu Val Cys Asp Phe Pro Arg Leu Ile His Ala Asp Asp Gln
            500                 505                 510

gat tat caa agt ttt ttg tcg aat gat ttt ggc caa agt aag cct gga     1584
Asp Tyr Gln Ser Phe Leu Ser Asn Asp Phe Gly Gln Ser Lys Pro Gly
        515                 520                 525

tac ata gac ctt gtt aaa gga gtt gag ggt gtg acg gga ata ata atg     1632
Tyr Ile Asp Leu Val Lys Gly Val Glu Gly Val Thr Gly Ile Ile Met
    530                 535                 540

gta atc ctt atg gcc att gct ttc act ctt gct aca cga tgg ttt aga     1680
Val Ile Leu Met Ala Ile Ala Phe Thr Leu Ala Thr Arg Trp Phe Arg
545                 550                 555                 560

cgg agc ctc att aag ttg ccc aaa cct ttt gat aga ctc act ggc ttc     1728
Arg Ser Leu Ile Lys Leu Pro Lys Pro Phe Asp Arg Leu Thr Gly Phe
                565                 570                 575

aat gca ttc tgg tat tca cac cac ctt ctt gtc att gtc tac atc cta     1776
Asn Ala Phe Trp Tyr Ser His His Leu Leu Val Ile Val Tyr Ile Leu
            580                 585                 590

ctg atc atc cat ggc acg ttc ctc ttc ctt gtg cat aaa tgg tac tcc     1824
Leu Ile Ile His Gly Thr Phe Leu Phe Leu Val His Lys Trp Tyr Ser
        595                 600                 605

aag acg acg tgg atg tat cta gca gtt cct gtg ctt ctc tac gca ggg     1872
Lys Thr Thr Trp Met Tyr Leu Ala Val Pro Val Leu Leu Tyr Ala Gly
    610                 615                 620

gaa aga act ctt aga ttc ttc cgg tca ggc ttg tac act gtc cgg ctt     1920
Glu Arg Thr Leu Arg Phe Phe Arg Ser Gly Leu Tyr Thr Val Arg Leu
625                 630                 635                 640

ctg aaa gta gca ata tat cct gga aat gtc ctc act cta caa atg tct     1968
Leu Lys Val Ala Ile Tyr Pro Gly Asn Val Leu Thr Leu Gln Met Ser
                645                 650                 655

aag cct cct caa ttt cga tac aaa agt gga caa tat atg ttt gtc cag     2016
Lys Pro Pro Gln Phe Arg Tyr Lys Ser Gly Gln Tyr Met Phe Val Gln
            660                 665                 670

tgt cca gct gtt tct cca ttc gag tgg cat cca ttt tcc att act tca     2064
Cys Pro Ala Val Ser Pro Phe Glu Trp His Pro Phe Ser Ile Thr Ser
        675                 680                 685

gct cct ggg gat gac tac ttg agc att cac atc cgg caa ctt ggt gac     2112
Ala Pro Gly Asp Asp Tyr Leu Ser Ile His Ile Arg Gln Leu Gly Asp
    690                 695                 700

tgg act caa gaa ctc aag cgg gtc ttt tct gag gct tgc gag cgg cca     2160
Trp Thr Gln Glu Leu Lys Arg Val Phe Ser Glu Ala Cys Glu Arg Pro
705                 710                 715                 720
```

```
gag gct gga aag agt ggc ctg ctc aga gct gac gaa aac act aag aaa      2208
Glu Ala Gly Lys Ser Gly Leu Leu Arg Ala Asp Glu Asn Thr Lys Lys
                725                 730                 735

agt ttg cca aag cta tta ata gat gga cct tac gga gct cca gca caa      2256
Ser Leu Pro Lys Leu Leu Ile Asp Gly Pro Tyr Gly Ala Pro Ala Gln
            740                 745                 750

gat tac cga aaa tat gat gtc ttg ctg ctt gtt ggt ctt ggc att gga      2304
Asp Tyr Arg Lys Tyr Asp Val Leu Leu Leu Val Gly Leu Gly Ile Gly
        755                 760                 765

gca acg ccg ttc ata agt atc ctg aaa gac ttg ctc gtt aac atc gtg      2352
Ala Thr Pro Phe Ile Ser Ile Leu Lys Asp Leu Leu Val Asn Ile Val
    770                 775                 780

aaa atg gag gag caa gca gat tta gcc tca gat ttc agt ggg aac tca      2400
Lys Met Glu Glu Gln Ala Asp Leu Ala Ser Asp Phe Ser Gly Asn Ser
785                 790                 795                 800

gac atg agc gtt gcg aca agt gaa caa cca gct ctc aac aag att tct      2448
Asp Met Ser Val Ala Thr Ser Glu Gln Pro Ala Leu Asn Lys Ile Ser
                805                 810                 815

ctg aaa agg aga aag agc act cta aga acc aca aat gca tat ttt tat      2496
Leu Lys Arg Arg Lys Ser Thr Leu Arg Thr Thr Asn Ala Tyr Phe Tyr
            820                 825                 830

tgg gtg acc cgg gag caa gga tca ttt gat tgg ttc aaa ggc gtt atg      2544
Trp Val Thr Arg Glu Gln Gly Ser Phe Asp Trp Phe Lys Gly Val Met
        835                 840                 845

aac gaa gtg gct gaa ctt gat caa agg ggg gtc atc gag atg cat aac      2592
Asn Glu Val Ala Glu Leu Asp Gln Arg Gly Val Ile Glu Met His Asn
    850                 855                 860

tac ttg acg agt gtt tat gag gaa ggg gat gct cgt tca gct ctc att      2640
Tyr Leu Thr Ser Val Tyr Glu Glu Gly Asp Ala Arg Ser Ala Leu Ile
865                 870                 875                 880

acc atg gtc cag gca ctt aac cat gct aag aat ggg gtt gat att gta      2688
Thr Met Val Gln Ala Leu Asn His Ala Lys Asn Gly Val Asp Ile Val
                885                 890                 895

tca ggc acc agg gtg agg aca cat ttt gct agg cca aat tgg aag aaa      2736
Ser Gly Thr Arg Val Arg Thr His Phe Ala Arg Pro Asn Trp Lys Lys
            900                 905                 910

gta ttt tcc aag acc tta acc aag cat gca aat gca aga ata ggg gtt      2784
Val Phe Ser Lys Thr Leu Thr Lys His Ala Asn Ala Arg Ile Gly Val
        915                 920                 925

ttc tac tgt ggt gca ccc gta tta gca aaa gaa ctc agc aaa ctc tgc      2832
Phe Tyr Cys Gly Ala Pro Val Leu Ala Lys Glu Leu Ser Lys Leu Cys
    930                 935                 940

aaa gag tat aat caa aag ggt gca aca aag ttc gag ttt cac aaa gaa      2880
Lys Glu Tyr Asn Gln Lys Gly Ala Thr Lys Phe Glu Phe His Lys Glu
945                 950                 955                 960

cat ttt tag                                                          2889
His Phe


<210> SEQ ID NO 6
<211> LENGTH: 962
<212> TYPE: PRT
<213> ORGANISM: Nicotiana tabacum

<400> SEQUENCE: 6

Met Arg Gly Leu Pro Gly His Glu Arg Arg Trp Thr Ser Asp Thr Val
  1               5                  10                  15

Ser Ser Asp Lys Asp Phe Ser Gly Glu Leu Ser Pro Gly Ala Asp Ser
             20                  25                  30

Gly Tyr Asn Ser Gly Phe Ala Ser Glu Glu Phe Val Glu Val Thr Leu
         35                  40                  45
```

```
Asp Leu Gln Asp Asp Asp Thr Ile Ile Leu Arg Ser Val Glu Pro Ala
     50                  55                  60

Thr Val Ile Asn Ile Asp Ala Pro Asp Leu Pro Ala Gly Val Gly Ile
 65                  70                  75                  80

Ser Gly Val Ser Ile Glu Thr Pro Thr Ser Ala Ser Val Ser Glu Ser
                 85                  90                  95

Arg Ser Pro Thr Ile Arg Arg Ser Ser Ser Ser Lys Leu Arg Gln Phe
            100                 105                 110

Ser Gln Glu Leu Lys Ala Glu Ala Val Ala Lys Ala Arg Gln Phe Ser
        115                 120                 125

Gln Glu Leu Lys Ala Glu Leu Arg Arg Phe Ser Trp Ser His Gly His
    130                 135                 140

Ala Ser Arg Ala Phe Ser Pro Ser Ser Phe Phe Gln Asn Ala Val Val
145                 150                 155                 160

Gly Thr Gly Asn Gly Val Asp Ser Ala Leu Ala Ala Arg Ala Leu Arg
                165                 170                 175

Arg Gln Arg Ala Gln Leu Asp Arg Thr Arg Ser Ser Ala His Arg Ala
            180                 185                 190

Leu Arg Arg Leu Lys Phe Ile Ser Asn Asn Lys Thr Asn Gly Trp Asn
        195                 200                 205

Glu Val Glu Asn Asn Phe Ser Lys Leu Ala Lys Asp Gly Tyr Leu Tyr
    210                 215                 220

Arg Ser Asp Phe Ala Gln Cys Ile Gly Met Lys Asp Ser Lys Glu Phe
225                 230                 235                 240

Ala Leu Glu Leu Phe Asp Ala Leu Ser Arg Arg Arg Arg Leu Lys Val
                245                 250                 255

Asp Lys Ile Ser Lys Glu Glu Leu Tyr Glu Tyr Trp Ser Gln Ile Thr
            260                 265                 270

Asp Gln Ser Phe Asp Ser Arg Leu Gln Ile Ser Phe Asp Met Val Asp
        275                 280                 285

Lys Asn Glu Asp Gly Arg Ile Ala Glu Glu Glu Val Lys Glu Ile Ile
    290                 295                 300

Met Leu Ser Ala Ser Ala Asn Lys Leu Ser Arg Leu Lys Glu Gln Ala
305                 310                 315                 320

Glu Glu Tyr Ala Ala Leu Ile Met Glu Glu Leu Asp Pro Glu Arg Leu
                325                 330                 335

Gly Tyr Ile Glu Leu Trp Gln Leu Glu Thr Leu Leu Leu Gln Lys Asp
            340                 345                 350

Thr Tyr Leu Asn Tyr Ser Gln Ala Leu Ser Tyr Thr Ser Gln Ala Leu
        355                 360                 365

Ser Gln Asn Leu His Gly Leu Arg Lys Lys Ser Pro Ile Lys Arg Met
    370                 375                 380

Ser Thr Lys Leu Val Tyr Ser Leu Gln Glu Asn Trp Lys Arg Ile Trp
385                 390                 395                 400

Val Leu Thr Leu Trp Ile Leu Ile Met Ile Gly Leu Phe Leu Trp Lys
                405                 410                 415

Phe Tyr Gln Tyr Lys Asn Lys Ser Ala Phe Arg Val Met Gly Tyr Cys
            420                 425                 430

Leu Val Thr Ala Lys Gly Ala Ala Glu Thr Leu Lys Phe Asn Met Ala
        435                 440                 445

Leu Ile Leu Leu Pro Val Cys Arg Asn Thr Ile Thr Trp Leu Arg Ser
    450                 455                 460

Thr Lys Leu Ser His Phe Val Pro Phe Asp Asp Asn Ile Asn Phe His
```

```
465                 470                 475                 480

Lys Thr Val Ala Ala Ala Ile Val Thr Gly Ile Ile Leu His Ala Gly
                485                 490                 495

Asn His Leu Val Cys Asp Phe Pro Arg Leu Ile His Ala Asp Asp Gln
            500                 505                 510

Asp Tyr Gln Ser Phe Leu Ser Asn Asp Phe Gly Gln Ser Lys Pro Gly
        515                 520                 525

Tyr Ile Asp Leu Val Lys Gly Val Glu Gly Val Thr Gly Ile Ile Met
    530                 535                 540

Val Ile Leu Met Ala Ile Ala Phe Thr Leu Ala Thr Arg Trp Phe Arg
545                 550                 555                 560

Arg Ser Leu Ile Lys Leu Pro Lys Pro Phe Asp Arg Leu Thr Gly Phe
                565                 570                 575

Asn Ala Phe Trp Tyr Ser His His Leu Leu Val Ile Val Tyr Ile Leu
            580                 585                 590

Leu Ile Ile His Gly Thr Phe Leu Phe Leu Val His Lys Trp Tyr Ser
        595                 600                 605

Lys Thr Thr Trp Met Tyr Leu Ala Val Pro Val Leu Leu Tyr Ala Gly
    610                 615                 620

Glu Arg Thr Leu Arg Phe Phe Arg Ser Gly Leu Tyr Thr Val Arg Leu
625                 630                 635                 640

Leu Lys Val Ala Ile Tyr Pro Gly Asn Val Leu Thr Leu Gln Met Ser
                645                 650                 655

Lys Pro Pro Gln Phe Arg Tyr Lys Ser Gly Gln Tyr Met Phe Val Gln
            660                 665                 670

Cys Pro Ala Val Ser Pro Phe Glu Trp His Pro Phe Ser Ile Thr Ser
        675                 680                 685

Ala Pro Gly Asp Asp Tyr Leu Ser Ile His Ile Arg Gln Leu Gly Asp
    690                 695                 700

Trp Thr Gln Glu Leu Lys Arg Val Phe Ser Glu Ala Cys Glu Arg Pro
705                 710                 715                 720

Glu Ala Gly Lys Ser Gly Leu Leu Arg Ala Asp Glu Asn Thr Lys Lys
                725                 730                 735

Ser Leu Pro Lys Leu Leu Ile Asp Gly Pro Tyr Gly Ala Pro Ala Gln
            740                 745                 750

Asp Tyr Arg Lys Tyr Asp Val Leu Leu Leu Val Gly Leu Gly Ile Gly
        755                 760                 765

Ala Thr Pro Phe Ile Ser Ile Leu Lys Asp Leu Leu Val Asn Ile Val
    770                 775                 780

Lys Met Glu Glu Gln Ala Asp Leu Ala Ser Asp Phe Ser Gly Asn Ser
785                 790                 795                 800

Asp Met Ser Val Ala Thr Ser Glu Gln Pro Ala Leu Asn Lys Ile Ser
                805                 810                 815

Leu Lys Arg Arg Lys Ser Thr Leu Arg Thr Thr Asn Ala Tyr Phe Tyr
            820                 825                 830

Trp Val Thr Arg Glu Gln Gly Ser Phe Asp Trp Phe Lys Gly Val Met
        835                 840                 845

Asn Glu Val Ala Glu Leu Asp Gln Arg Gly Val Ile Glu Met His Asn
    850                 855                 860

Tyr Leu Thr Ser Val Tyr Glu Glu Gly Asp Ala Arg Ser Ala Leu Ile
865                 870                 875                 880

Thr Met Val Gln Ala Leu Asn His Ala Lys Asn Gly Val Asp Ile Val
                885                 890                 895
```

```
Ser Gly Thr Arg Val Arg Thr His Phe Ala Arg Pro Asn Trp Lys Lys
            900                 905                 910

Val Phe Ser Lys Thr Leu Thr Lys His Ala Asn Ala Arg Ile Gly Val
        915                 920                 925

Phe Tyr Cys Gly Ala Pro Val Leu Ala Lys Glu Leu Ser Lys Leu Cys
    930                 935                 940

Lys Glu Tyr Asn Gln Lys Gly Ala Thr Lys Phe Glu Phe His Lys Glu
945                 950                 955                 960

His Phe


<210> SEQ ID NO 7
<211> LENGTH: 3733
<212> TYPE: DNA
<213> ORGANISM: Solanum tuberosum
<220> FEATURE:
<221> NAME/KEY: CDS
<222> LOCATION: (92)..(2980)
<223> OTHER INFORMATION: coding for NADPH oxidase

<400> SEQUENCE: 7

ggcacgagaa taaccaaaac ttttggtcag gcttctgcag aaaactctgt tttcaacata      60

tatttattta ttgtgctttg atttgggaca a atg agg ggt tta cct ggg cat        112
                                   Met Arg Gly Leu Pro Gly His
                                     1               5

gaa cgc cgg tgg acg tcg gat acg gta tct tcc ggc aag gat tta agt       160
Glu Arg Arg Trp Thr Ser Asp Thr Val Ser Ser Gly Lys Asp Leu Ser
         10                  15                  20

ggt gag tca tcg ccg gga act gat tcc ggg aat att tcc ggt ttt gct       208
Gly Glu Ser Ser Pro Gly Thr Asp Ser Gly Asn Ile Ser Gly Phe Ala
     25                  30                  35

tcc gag gag ttt gtt gaa gtt ata ctt gat ctt cag gat gat gat acg       256
Ser Glu Glu Phe Val Glu Val Ile Leu Asp Leu Gln Asp Asp Asp Thr
 40                  45                  50                  55

att att cta cgg agc gtt gaa ccg gct act gta atc aac att gat gct       304
Ile Ile Leu Arg Ser Val Glu Pro Ala Thr Val Ile Asn Ile Asp Ala
                 60                  65                  70

tct gat cct gct acc gga gtc ggt att ggt gga gta tcg att gaa act       352
Ser Asp Pro Ala Thr Gly Val Gly Ile Gly Gly Val Ser Ile Glu Thr
             75                  80                  85

ccg gcg tcg ctg act tcg acg tcg gga act cga tcg ccg acg atg cgt       400
Pro Ala Ser Leu Thr Ser Thr Ser Gly Thr Arg Ser Pro Thr Met Arg
         90                  95                 100

cgg agt aca tcg aat aaa tta cgt cag ttt tca cag gag ttg aaa gct       448
Arg Ser Thr Ser Asn Lys Leu Arg Gln Phe Ser Gln Glu Leu Lys Ala
    105                 110                 115

gag gct gtc gcg aaa gcg aag cat ttc tcg caa gag ctt aaa gcg gag       496
Glu Ala Val Ala Lys Ala Lys His Phe Ser Gln Glu Leu Lys Ala Glu
120                 125                 130                 135

cta agg aga ttc tca tgg agc cat gga cat gcg tct cgc act ttt tcg       544
Leu Arg Arg Phe Ser Trp Ser His Gly His Ala Ser Arg Thr Phe Ser
                140                 145                 150

ccg gcg tcg ttt ttc caa aac gcc gtc gtc ggt aca ggc aac ggt gta       592
Pro Ala Ser Phe Phe Gln Asn Ala Val Val Gly Thr Gly Asn Gly Val
            155                 160                 165

gat tcg gct tta gca gct cga gca tta cga cgg cag cgc gct cag ctc       640
Asp Ser Ala Leu Ala Ala Arg Ala Leu Arg Arg Gln Arg Ala Gln Leu
        170                 175                 180

gat cgg act cgt tcc agc gct cac aag gct ctt cgt gga ctc aaa ttc       688
Asp Arg Thr Arg Ser Ser Ala His Lys Ala Leu Arg Gly Leu Lys Phe
    185                 190                 195
```

```
atc agc aat aac aaa act aac gga tgg aat gaa gtt gaa aac aat ttt      736
Ile Ser Asn Asn Lys Thr Asn Gly Trp Asn Glu Val Glu Asn Asn Phe
200                 205                 210                 215

gct aag ctc gct aaa gac ggt tac ctt tat cgc tcc gat ttc gca caa      784
Ala Lys Leu Ala Lys Asp Gly Tyr Leu Tyr Arg Ser Asp Phe Ala Gln
                220                 225                 230

tgc atc ggt atg aag gat tca aag gaa ttt gca ttg gaa ttg ttt gat      832
Cys Ile Gly Met Lys Asp Ser Lys Glu Phe Ala Leu Glu Leu Phe Asp
            235                 240                 245

gct ttg agt aga aga aga aga ttg aag gtt gat aag att agc aaa gag      880
Ala Leu Ser Arg Arg Arg Arg Leu Lys Val Asp Lys Ile Ser Lys Glu
        250                 255                 260

gaa ttg tat gag tat tgg tct caa atc acc gat cag agt ttc gat tct      928
Glu Leu Tyr Glu Tyr Trp Ser Gln Ile Thr Asp Gln Ser Phe Asp Ser
    265                 270                 275

cgg ctt cag atc ttc ttc gac atg gtg gac aag aat gaa gat ggt cga      976
Arg Leu Gln Ile Phe Phe Asp Met Val Asp Lys Asn Glu Asp Gly Arg
280                 285                 290                 295

att ggt gaa gaa gaa gta aaa gag atc atc atg cta agt gcc tct gca     1024
Ile Gly Glu Glu Glu Val Lys Glu Ile Ile Met Leu Ser Ala Ser Ala
                300                 305                 310

aac aaa tta tca aga tta aaa gaa caa gca gag gag tat gca gct ctg     1072
Asn Lys Leu Ser Arg Leu Lys Glu Gln Ala Glu Glu Tyr Ala Ala Leu
            315                 320                 325

atc atg gaa gaa tta gat cct gaa aga ctt ggc tac att gag cta tgg     1120
Ile Met Glu Glu Leu Asp Pro Glu Arg Leu Gly Tyr Ile Glu Leu Trp
        330                 335                 340

cag ctg gaa acg ctt ctc ctc caa aag gac act tac ctc aac tac agt     1168
Gln Leu Glu Thr Leu Leu Leu Gln Lys Asp Thr Tyr Leu Asn Tyr Ser
    345                 350                 355

caa gca cta agc tac aca agc caa gct ttg agc caa aac ctg caa ggg     1216
Gln Ala Leu Ser Tyr Thr Ser Gln Ala Leu Ser Gln Asn Leu Gln Gly
360                 365                 370                 375

ttg agg aag aga agc cca ata aga aga atg agc aca aaa ctt gtc tat     1264
Leu Arg Lys Arg Ser Pro Ile Arg Arg Met Ser Thr Lys Leu Val Tyr
                380                 385                 390

tca ctg caa gag aat tgg aag aga att tgg gtt ctg gtc ttg tgg att     1312
Ser Leu Gln Glu Asn Trp Lys Arg Ile Trp Val Leu Val Leu Trp Ile
            395                 400                 405

ttg ata atg att gga ctt ttt ctt tgg aag ttc tat ctg tac aaa cag     1360
Leu Ile Met Ile Gly Leu Phe Leu Trp Lys Phe Tyr Leu Tyr Lys Gln
        410                 415                 420

aaa agt gca ttt caa gtt atg ggt tat tgc ctt cta aca gct aag ggt     1408
Lys Ser Ala Phe Gln Val Met Gly Tyr Cys Leu Leu Thr Ala Lys Gly
    425                 430                 435

gct gct gag act cta aag ttc aac atg gct ttg ata ttg ttg cca gtt     1456
Ala Ala Glu Thr Leu Lys Phe Asn Met Ala Leu Ile Leu Leu Pro Val
440                 445                 450                 455

tgc agg aac acc att aca ttc ctc agg tct act aaa ttg agt tgt ttt     1504
Cys Arg Asn Thr Ile Thr Phe Leu Arg Ser Thr Lys Leu Ser Cys Phe
                460                 465                 470

gta ccc ttt gat gac aac atc aac ttc cac aag act gtt gct gca gcc     1552
Val Pro Phe Asp Asp Asn Ile Asn Phe His Lys Thr Val Ala Ala Ala
            475                 480                 485

att gtt act ggt atc ata ctc cat gcc ggt aat cat ctt gta tgt gat     1600
Ile Val Thr Gly Ile Ile Leu His Ala Gly Asn His Leu Val Cys Asp
        490                 495                 500

ttc cca aag ctt ata cat gca aat aat acg aat tat cag aaa tat ttg     1648
Phe Pro Lys Leu Ile His Ala Asn Asn Thr Asn Tyr Gln Lys Tyr Leu
    505                 510                 515
```

```
gtg aat gat ttt ggc cca agc cag cct cag tac ata gat ctt gtt aaa      1696
Val Asn Asp Phe Gly Pro Ser Gln Pro Gln Tyr Ile Asp Leu Val Lys
520                 525                 530                 535

gga gtg gag ggt gtg aca gga ata ata atg gta atc ctc atg gcc att      1744
Gly Val Glu Gly Val Thr Gly Ile Ile Met Val Ile Leu Met Ala Ile
                540                 545                 550

gct ttc act ctt gca acg cga tgg ttt agg cgg agc ctc att aag ttt      1792
Ala Phe Thr Leu Ala Thr Arg Trp Phe Arg Arg Ser Leu Ile Lys Phe
            555                 560                 565

ccc aaa cct ttt gat aga ctc act ggt ttc aat gcg ttc tgg tac tcg      1840
Pro Lys Pro Phe Asp Arg Leu Thr Gly Phe Asn Ala Phe Trp Tyr Ser
        570                 575                 580

cac cac ctt ctc atc att gtc tac atc gta ctg atc atc cat ggc aca      1888
His His Leu Leu Ile Ile Val Tyr Ile Val Leu Ile Ile His Gly Thr
    585                 590                 595

ttc ctc tac ctt gtg cat aac tgg tac tcc aaa acg aca tgg atg tat      1936
Phe Leu Tyr Leu Val His Asn Trp Tyr Ser Lys Thr Thr Trp Met Tyr
600                 605                 610                 615

cta gca gtt cct gta ctt ctc tac gca ggg gaa aga act ctt aga ttc      1984
Leu Ala Val Pro Val Leu Leu Tyr Ala Gly Glu Arg Thr Leu Arg Phe
                620                 625                 630

ttc cga tca ggc tta tat aca gtc cgg ctt cta aaa gta gca ata tat      2032
Phe Arg Ser Gly Leu Tyr Thr Val Arg Leu Leu Lys Val Ala Ile Tyr
            635                 640                 645

cct gga aat gtc ctt act ctg caa atg tct aag cct ccg caa ttt cga      2080
Pro Gly Asn Val Leu Thr Leu Gln Met Ser Lys Pro Pro Gln Phe Arg
        650                 655                 660

tac aag agt gga caa tat atg ttt gtc cag tgt cca gct gtt tct cca      2128
Tyr Lys Ser Gly Gln Tyr Met Phe Val Gln Cys Pro Ala Val Ser Pro
    665                 670                 675

ttc gag tgg cat cca ttt tcc att act tca gct cct ggg gat gac tac      2176
Phe Glu Trp His Pro Phe Ser Ile Thr Ser Ala Pro Gly Asp Asp Tyr
680                 685                 690                 695

ttg agc att cat atc cga caa ctt ggt gac tgg act caa gaa ctc aag      2224
Leu Ser Ile His Ile Arg Gln Leu Gly Asp Trp Thr Gln Glu Leu Lys
                700                 705                 710

cgg gtg ttt tcc gag gct tgc gag cag cca gag gct gga aag agt ggc      2272
Arg Val Phe Ser Glu Ala Cys Glu Gln Pro Glu Ala Gly Lys Ser Gly
            715                 720                 725

ctg ctc aga gct gac gaa aac acc aaa aca agt ttg cca aag cta ttg      2320
Leu Leu Arg Ala Asp Glu Asn Thr Lys Thr Ser Leu Pro Lys Leu Leu
        730                 735                 740

ata gat gga cct tat gga gct cca gca caa gat tac cga aag tat gat      2368
Ile Asp Gly Pro Tyr Gly Ala Pro Ala Gln Asp Tyr Arg Lys Tyr Asp
    745                 750                 755

gtc tta ctg ctt gtt ggt ctt ggc att gga gca act ccc ttt ata agt      2416
Val Leu Leu Leu Val Gly Leu Gly Ile Gly Ala Thr Pro Phe Ile Ser
760                 765                 770                 775

atc ctg aaa gac ttg ctc aaa aac atc gtc aca atg gag gag caa gca      2464
Ile Leu Lys Asp Leu Leu Lys Asn Ile Val Thr Met Glu Glu Gln Ala
                780                 785                 790

gat tta gtc tcg gat ttt tca ggg aac tca gac atg agc gct gca aca      2512
Asp Leu Val Ser Asp Phe Ser Gly Asn Ser Asp Met Ser Ala Ala Thr
            795                 800                 805

agt gaa caa cca gct ctc aac aag att tct cca aaa aag aga aag agt      2560
Ser Glu Gln Pro Ala Leu Asn Lys Ile Ser Pro Lys Lys Arg Lys Ser
        810                 815                 820

act cta aaa acc aca aat gca tat ttt tat tgg gtg acc cgg gag caa      2608
Thr Leu Lys Thr Thr Asn Ala Tyr Phe Tyr Trp Val Thr Arg Glu Gln
    825                 830                 835
```

gga tca ttt gat tgg ttc aaa ggt gtt atg aac gaa gtg gct gaa ctt 2656
Gly Ser Phe Asp Trp Phe Lys Gly Val Met Asn Glu Val Ala Glu Leu
840 845 850 855 gat caa agg ggg gtc atc gag atg cat aac tac tta acg agt gtt tat 2704
Asp Gln Arg Gly Val Ile Glu Met His Asn Tyr Leu Thr Ser Val Tyr
860 865 870 gag gaa ggg gat gca cgt tca gct ctc att acc atg gtc cag gcg ctt 2752
Glu Glu Gly Asp Ala Arg Ser Ala Leu Ile Thr Met Val Gln Ala Leu
875 880 885 aac cat gct aag aat ggg gtt gat att gta tca ggc acc agt gtg agg 2800
Asn His Ala Lys Asn Gly Val Asp Ile Val Ser Gly Thr Ser Val Arg
890 895 900 aca cat ttt gcc aga ccg aat tgg agg aaa gta ttt tcc aag acc tta 2848
Thr His Phe Ala Arg Pro Asn Trp Arg Lys Val Phe Ser Lys Thr Leu
905 910 915 acc aag cat gca aat gca aga ata gga gtt ttc tac tgc ggt gca ccc 2896
Thr Lys His Ala Asn Ala Arg Ile Gly Val Phe Tyr Cys Gly Ala Pro
920 925 930 935 ata tta gct aaa gaa ctc agc aaa ctc tgc aaa gag ttt aac caa aag 2944
Ile Leu Ala Lys Glu Leu Ser Lys Leu Cys Lys Glu Phe Asn Gln Lys
940 945 950 ggc aca acg aag ttc gag ttt cac aaa gaa cat ttt tagaaggccc 2990
Gly Thr Thr Lys Phe Glu Phe His Lys Glu His Phe
955 960 tggagtacaa ttaatcttgc atcaacggta cacacatcgg taaaccagta tttaccacat 3050
ctatctttgg tacctgattt gatgattcta ctgaagacat aacattagta aggaataagt 3110
cagagacaaa ttgtacataa taggaggaag cacatttaca gagaaaatac ataccaatat 3170
gatatgtgta taggttttgt atattcagtc atctgttatc acataccaaa cttcagaact 3230
ccaaaaggga gactctgctt tggtctgatg gcttagaata tgggagggaa aaaaagacga 3290
caattgaatg gtcacgatac acatgaagaa tgagaatatt gggaaacagc taataagaag 3350
ttgaccttct tgataaagaa acactatgaa aatggcaagc atgaaaggac agacaatcat 3410
ggcttggatg gggaaaacaa aatacaattt tgaaagaaga agataatatt agtaggagta 3470
gtgggggact gatagctttg ttggtggaac ttataatggg gctaagggaa tccttccaaa 3530
aaatgtctat gtagtaacta ctttttcttt tgctttgtga gtatttttttg gggtatttta 3590 atatactact tattagataa gaggatagaa aatacgtgta tatgcaattc ttattagtaa 3650
agtttatctg tagtagttct ttaatctgga gaaaggtact atcaaaggaa atatctcatc 3710
gaaaaaaaaa aaaaaaaaaa aaa 3733

<210> SEQ ID NO 8
<211> LENGTH: 963
<212> TYPE: PRT
<213> ORGANISM: Solanum tuberosum

<400> SEQUENCE: 8

Met Arg Gly Leu Pro Gly His Glu Arg Arg Trp Thr Ser Asp Thr Val
1 5 10 15

Ser Ser Gly Lys Asp Leu Ser Gly Glu Ser Ser Pro Gly Thr Asp Ser
20 25 30

Gly Asn Ile Ser Gly Phe Ala Ser Glu Glu Phe Val Glu Val Ile Leu
35 40 45

Asp Leu Gln Asp Asp Asp Thr Ile Ile Leu Arg Ser Val Glu Pro Ala
50 55 60

Thr Val Ile Asn Ile Asp Ala Ser Asp Pro Ala Thr Gly Val Gly Ile
65 70 75 80

-continued

```
Gly Gly Val Ser Ile Glu Thr Pro Ala Ser Leu Thr Ser Thr Ser Gly
                85                  90                  95

Thr Arg Ser Pro Thr Met Arg Arg Ser Thr Ser Asn Lys Leu Arg Gln
            100                 105                 110

Phe Ser Gln Glu Leu Lys Ala Glu Ala Val Ala Lys Ala Lys His Phe
        115                 120                 125

Ser Gln Glu Leu Lys Ala Glu Leu Arg Arg Phe Ser Trp Ser His Gly
    130                 135                 140

His Ala Ser Arg Thr Phe Ser Pro Ala Ser Phe Phe Gln Asn Ala Val
145                 150                 155                 160

Val Gly Thr Gly Asn Gly Val Asp Ser Ala Leu Ala Ala Arg Ala Leu
                165                 170                 175

Arg Arg Gln Arg Ala Gln Leu Asp Arg Thr Arg Ser Ser Ala His Lys
            180                 185                 190

Ala Leu Arg Gly Leu Lys Phe Ile Ser Asn Asn Lys Thr Asn Gly Trp
        195                 200                 205

Asn Glu Val Glu Asn Asn Phe Ala Lys Leu Ala Lys Asp Gly Tyr Leu
    210                 215                 220

Tyr Arg Ser Asp Phe Ala Gln Cys Ile Gly Met Lys Asp Ser Lys Glu
225                 230                 235                 240

Phe Ala Leu Glu Leu Phe Asp Ala Leu Ser Arg Arg Arg Arg Leu Lys
                245                 250                 255

Val Asp Lys Ile Ser Lys Glu Glu Leu Tyr Glu Tyr Trp Ser Gln Ile
            260                 265                 270

Thr Asp Gln Ser Phe Asp Ser Arg Leu Gln Ile Phe Phe Asp Met Val
        275                 280                 285

Asp Lys Asn Glu Asp Gly Arg Ile Gly Glu Glu Glu Val Lys Glu Ile
    290                 295                 300

Ile Met Leu Ser Ala Ser Ala Asn Lys Leu Ser Arg Leu Lys Glu Gln
305                 310                 315                 320

Ala Glu Glu Tyr Ala Ala Leu Ile Met Glu Glu Leu Asp Pro Glu Arg
                325                 330                 335

Leu Gly Tyr Ile Glu Leu Trp Gln Leu Glu Thr Leu Leu Leu Gln Lys
            340                 345                 350

Asp Thr Tyr Leu Asn Tyr Ser Gln Ala Leu Ser Tyr Thr Ser Gln Ala
        355                 360                 365

Leu Ser Gln Asn Leu Gln Gly Leu Arg Lys Arg Ser Pro Ile Arg Arg
    370                 375                 380

Met Ser Thr Lys Leu Val Tyr Ser Leu Gln Glu Asn Trp Lys Arg Ile
385                 390                 395                 400

Trp Val Leu Val Leu Trp Ile Leu Ile Met Ile Gly Leu Phe Leu Trp
                405                 410                 415

Lys Phe Tyr Leu Tyr Lys Gln Lys Ser Ala Phe Gln Val Met Gly Tyr
            420                 425                 430

Cys Leu Leu Thr Ala Lys Gly Ala Ala Glu Thr Leu Lys Phe Asn Met
        435                 440                 445

Ala Leu Ile Leu Leu Pro Val Cys Arg Asn Thr Ile Thr Phe Leu Arg
    450                 455                 460

Ser Thr Lys Leu Ser Cys Phe Val Pro Phe Asp Asp Asn Ile Asn Phe
465                 470                 475                 480

His Lys Thr Val Ala Ala Ala Ile Val Thr Gly Ile Ile Leu His Ala
                485                 490                 495

Gly Asn His Leu Val Cys Asp Phe Pro Lys Leu Ile His Ala Asn Asn
```

```
            500                 505                 510

Thr Asn Tyr Gln Lys Tyr Leu Val Asn Asp Phe Gly Pro Ser Gln Pro
        515                 520                 525

Gln Tyr Ile Asp Leu Val Lys Gly Val Glu Gly Val Thr Gly Ile Ile
    530                 535                 540

Met Val Ile Leu Met Ala Ile Ala Phe Thr Leu Ala Thr Arg Trp Phe
545                 550                 555                 560

Arg Arg Ser Leu Ile Lys Phe Pro Lys Pro Phe Asp Arg Leu Thr Gly
                565                 570                 575

Phe Asn Ala Phe Trp Tyr Ser His His Leu Leu Ile Ile Val Tyr Ile
            580                 585                 590

Val Leu Ile Ile His Gly Thr Phe Leu Tyr Leu Val His Asn Trp Tyr
        595                 600                 605

Ser Lys Thr Thr Trp Met Tyr Leu Ala Val Pro Val Leu Leu Tyr Ala
    610                 615                 620

Gly Glu Arg Thr Leu Arg Phe Phe Arg Ser Gly Leu Tyr Thr Val Arg
625                 630                 635                 640

Leu Leu Lys Val Ala Ile Tyr Pro Gly Asn Val Leu Thr Leu Gln Met
                645                 650                 655

Ser Lys Pro Pro Gln Phe Arg Tyr Lys Ser Gly Gln Tyr Met Phe Val
            660                 665                 670

Gln Cys Pro Ala Val Ser Pro Phe Glu Trp His Pro Phe Ser Ile Thr
        675                 680                 685

Ser Ala Pro Gly Asp Asp Tyr Leu Ser Ile His Ile Arg Gln Leu Gly
    690                 695                 700

Asp Trp Thr Gln Glu Leu Lys Arg Val Phe Ser Glu Ala Cys Glu Gln
705                 710                 715                 720

Pro Glu Ala Gly Lys Ser Gly Leu Leu Arg Ala Asp Glu Asn Thr Lys
                725                 730                 735

Thr Ser Leu Pro Lys Leu Leu Ile Asp Gly Pro Tyr Gly Ala Pro Ala
            740                 745                 750

Gln Asp Tyr Arg Lys Tyr Asp Val Leu Leu Leu Val Gly Leu Gly Ile
        755                 760                 765

Gly Ala Thr Pro Phe Ile Ser Ile Leu Lys Asp Leu Leu Lys Asn Ile
    770                 775                 780

Val Thr Met Glu Glu Gln Ala Asp Leu Val Ser Asp Phe Ser Gly Asn
785                 790                 795                 800

Ser Asp Met Ser Ala Ala Thr Ser Glu Gln Pro Ala Leu Asn Lys Ile
                805                 810                 815

Ser Pro Lys Lys Arg Lys Ser Thr Leu Lys Thr Thr Asn Ala Tyr Phe
            820                 825                 830

Tyr Trp Val Thr Arg Glu Gln Gly Ser Phe Asp Trp Phe Lys Gly Val
        835                 840                 845

Met Asn Glu Val Ala Glu Leu Asp Gln Arg Gly Val Ile Glu Met His
    850                 855                 860

Asn Tyr Leu Thr Ser Val Tyr Glu Glu Gly Asp Ala Arg Ser Ala Leu
865                 870                 875                 880

Ile Thr Met Val Gln Ala Leu Asn His Ala Lys Asn Gly Val Asp Ile
                885                 890                 895

Val Ser Gly Thr Ser Val Arg Thr His Phe Ala Arg Pro Asn Trp Arg
            900                 905                 910

Lys Val Phe Ser Lys Thr Leu Thr Lys His Ala Asn Ala Arg Ile Gly
        915                 920                 925
```

-continued

```
Val Phe Tyr Cys Gly Ala Pro Ile Leu Ala Lys Glu Leu Ser Lys Leu
    930                 935                 940

Cys Lys Glu Phe Asn Gln Lys Gly Thr Thr Lys Phe Glu Phe His Lys
945                 950                 955                 960

Glu His Phe


<210> SEQ ID NO 9
<211> LENGTH: 3316
<212> TYPE: DNA
<213> ORGANISM: Lycopersicon esculentum
<220> FEATURE:
<221> NAME/KEY: CDS
<222> LOCATION: (146)..(3112)
<223> OTHER INFORMATION: coding for NADPH oxidase

<400> SEQUENCE: 9

cgccactcgt gccgaattcg gcacgaggct ctgaaaaact tttcatacaa agccaatcta      60

tttctctctc tttcttttgg tcaggcttct acagaaaact ctgttttcaa cgtatattta     120

tttattgtca tttgatttgg gacag atg agg ggt tta cct ggg cat gaa cgc       172
                            Met Arg Gly Leu Pro Gly His Glu Arg
                              1               5

cgg tgg acg tcg gat acg gtg tct tcc ggg aag gat tta agt ggt gag       220
Arg Trp Thr Ser Asp Thr Val Ser Ser Gly Lys Asp Leu Ser Gly Glu
 10                  15                  20                  25

tca tcg ccg gga act gat tcc ggg aat att tcc ggt ttt gct tcg gag       268
Ser Ser Pro Gly Thr Asp Ser Gly Asn Ile Ser Gly Phe Ala Ser Glu
                 30                  35                  40

gag ttt gtt gaa gtt ata ctt gat ctt cag gat gat gat acg att att       316
Glu Phe Val Glu Val Ile Leu Asp Leu Gln Asp Asp Asp Thr Ile Ile
             45                  50                  55

tta cgg agc gtt gaa ccg gct act gta atc aac att gat ggt tct gat       364
Leu Arg Ser Val Glu Pro Ala Thr Val Ile Asn Ile Asp Gly Ser Asp
         60                  65                  70

cct gct tcc gga gtc ggt att ggt gga gca tcg att gaa act ccg gcg       412
Pro Ala Ser Gly Val Gly Ile Gly Gly Ala Ser Ile Glu Thr Pro Ala
     75                  80                  85

tcg gtg acg tcg acg tcg gaa act cga tcg ccg atg atg cgt cgg agt       460
Ser Val Thr Ser Thr Ser Glu Thr Arg Ser Pro Met Met Arg Arg Ser
 90                  95                 100                 105

aca tct aat aag ttt cgt cag ttt tca cag gag ttg aaa gct gag gct       508
Thr Ser Asn Lys Phe Arg Gln Phe Ser Gln Glu Leu Lys Ala Glu Ala
                110                 115                 120

gtt gcg aaa gcg aag cat ttc tcg caa gag ctt aaa gcg gag cta agg       556
Val Ala Lys Ala Lys His Phe Ser Gln Glu Leu Lys Ala Glu Leu Arg
            125                 130                 135

aga ttc tca tgg agc cat gga cat gcg tct cgt gct ttt tcg ccg gcg       604
Arg Phe Ser Trp Ser His Gly His Ala Ser Arg Ala Phe Ser Pro Ala
        140                 145                 150

tcg ttt ttc caa aac gct gtc gtc gga aca ggc aac ggt gta gac tcg       652
Ser Phe Phe Gln Asn Ala Val Val Gly Thr Gly Asn Gly Val Asp Ser
    155                 160                 165

gct tta gcg gct cga gca tta cgt cgg cag cgt gct cag ctc gac cgg       700
Ala Leu Ala Ala Arg Ala Leu Arg Arg Gln Arg Ala Gln Leu Asp Arg
170                 175                 180                 185

act cgt tcc agc gca cac aag gct ctt cgt gga ctc aaa ttc atc agc       748
Thr Arg Ser Ser Ala His Lys Ala Leu Arg Gly Leu Lys Phe Ile Ser
                190                 195                 200

aat aac aaa act aac gga tgg aat gaa gtt gaa aac aat ttc gct aag       796
Asn Asn Lys Thr Asn Gly Trp Asn Glu Val Glu Asn Asn Phe Ala Lys
            205                 210                 215
```

```
ctc gct aaa gac ggt tac ctt tat cgt tcc gat ttc gca caa tgc atc      844
Leu Ala Lys Asp Gly Tyr Leu Tyr Arg Ser Asp Phe Ala Gln Cys Ile
        220                 225                 230

ggt cag tac tca cgc cgg cga tca cta cag ttt aat tat aga tta att      892
Gly Gln Tyr Ser Arg Arg Arg Ser Leu Gln Phe Asn Tyr Arg Leu Ile
    235                 240                 245

aca tta att ttg att aat tat ttg gtt aaa ggt atg aag gat tca aag      940
Thr Leu Ile Leu Ile Asn Tyr Leu Val Lys Gly Met Lys Asp Ser Lys
250                 255                 260                 265

gaa ttt gcg ttg gaa ttg ttt gat gct tta agt aga aga aga aga ttg      988
Glu Phe Ala Leu Glu Leu Phe Asp Ala Leu Ser Arg Arg Arg Arg Leu
                270                 275                 280

aag gtt gat aag att agc caa gag gaa ttg tat gag tat tgg tct caa     1036
Lys Val Asp Lys Ile Ser Gln Glu Glu Leu Tyr Glu Tyr Trp Ser Gln
            285                 290                 295

atc acc gat cag agt ttc gat tct cgg ctt cag atc ttc ttc gac atg     1084
Ile Thr Asp Gln Ser Phe Asp Ser Arg Leu Gln Ile Phe Phe Asp Met
        300                 305                 310

gtg gac aag aat gaa gat ggt cga att ggt gaa gaa gaa gta aaa gag     1132
Val Asp Lys Asn Glu Asp Gly Arg Ile Gly Glu Glu Glu Val Lys Glu
    315                 320                 325

atc atc atg cta agt gcc tct gca aac aaa tta tca aga tta aaa gaa     1180
Ile Ile Met Leu Ser Ala Ser Ala Asn Lys Leu Ser Arg Leu Lys Glu
330                 335                 340                 345

caa gca gag gag tat gca gct ctg atc atg gaa gaa tta gat cct gaa     1228
Gln Ala Glu Glu Tyr Ala Ala Leu Ile Met Glu Glu Leu Asp Pro Glu
                350                 355                 360

aga ctt ggc tac att gag cta tgg cag ctg gaa aca ctt ctc ctc caa     1276
Arg Leu Gly Tyr Ile Glu Leu Trp Gln Leu Glu Thr Leu Leu Leu Gln
            365                 370                 375

aag gac act tac ctc aac tac agt caa gca cta agc tac aca agc caa     1324
Lys Asp Thr Tyr Leu Asn Tyr Ser Gln Ala Leu Ser Tyr Thr Ser Gln
        380                 385                 390

gct ttg agc caa aat ctg caa ggg ttg agg aag aga agc cca ata aga     1372
Ala Leu Ser Gln Asn Leu Gln Gly Leu Arg Lys Arg Ser Pro Ile Arg
    395                 400                 405

aga atg agc aca aaa ctt gtc tat tca ctg caa gag aat tgg aag aga     1420
Arg Met Ser Thr Lys Leu Val Tyr Ser Leu Gln Glu Asn Trp Lys Arg
410                 415                 420                 425

att tgg gtt ctg gtc ttg tgg att ttg ata atg att gga ctt ttt ctt     1468
Ile Trp Val Leu Val Leu Trp Ile Leu Ile Met Ile Gly Leu Phe Leu
                430                 435                 440

tgg aag ttc tat cag tac aaa cag aaa agt gca ttt caa gtc atg ggt     1516
Trp Lys Phe Tyr Gln Tyr Lys Gln Lys Ser Ala Phe Gln Val Met Gly
            445                 450                 455

tat tgc ctt cta aca gct aag ggt gct gct gag act ctc aag ttc aac     1564
Tyr Cys Leu Leu Thr Ala Lys Gly Ala Ala Glu Thr Leu Lys Phe Asn
        460                 465                 470

atg gct tta ata ttg ttg cca gta tgc agg aac acc att aca ttc ctc     1612
Met Ala Leu Ile Leu Leu Pro Val Cys Arg Asn Thr Ile Thr Phe Leu
    475                 480                 485

agg tct act aaa ttg agc tgt ttt gta ccc ttt gat gac aac ata aac     1660
Arg Ser Thr Lys Leu Ser Cys Phe Val Pro Phe Asp Asp Asn Ile Asn
490                 495                 500                 505

ttt cac aag act gtt gct gca gcc att gtc act ggt atc ata ctc cat     1708
Phe His Lys Thr Val Ala Ala Ala Ile Val Thr Gly Ile Ile Leu His
                510                 515                 520

gcc ggt aat cac ctt gta tgt gat ttc cca aag ctt ata cat gca aat     1756
Ala Gly Asn His Leu Val Cys Asp Phe Pro Lys Leu Ile His Ala Asn
            525                 530                 535
```

-continued

```
agt acg aat tat cag aaa tat ttg gtg aat gat ttt ggc cca agc cag      1804
Ser Thr Asn Tyr Gln Lys Tyr Leu Val Asn Asp Phe Gly Pro Ser Gln
        540                 545                 550

cct cag tac ata gat ctt gtt aaa gga gtg gag ggt gtg act gga ata      1852
Pro Gln Tyr Ile Asp Leu Val Lys Gly Val Glu Gly Val Thr Gly Ile
    555                 560                 565

gtt atg gta atc ctc atg gcc att gct ttc act ctt gca acg cga tgg      1900
Val Met Val Ile Leu Met Ala Ile Ala Phe Thr Leu Ala Thr Arg Trp
570                 575                 580                 585

ttt agg cgg agc ctc att aag tta ccc aaa cct ttt gat aga ctc act      1948
Phe Arg Arg Ser Leu Ile Lys Leu Pro Lys Pro Phe Asp Arg Leu Thr
                590                 595                 600

ggt ttc aat gcg ttc tgg tac tcg cac cac ctt ctc atc att gtc tac      1996
Gly Phe Asn Ala Phe Trp Tyr Ser His His Leu Leu Ile Ile Val Tyr
            605                 610                 615

atc gta ctg atc atc cat ggc aca ttc ctc tac ctt gtg cat aac tgg      2044
Ile Val Leu Ile Ile His Gly Thr Phe Leu Tyr Leu Val His Asn Trp
        620                 625                 630

tac tcc aaa acg aca tgg atg tat ata gca gtt cct gta ctt ctt tac      2092
Tyr Ser Lys Thr Thr Trp Met Tyr Ile Ala Val Pro Val Leu Leu Tyr
    635                 640                 645

gca ggg gaa aga act ctt aga ttc ttc cga tca ggc tta tac agt gtc      2140
Ala Gly Glu Arg Thr Leu Arg Phe Phe Arg Ser Gly Leu Tyr Ser Val
650                 655                 660                 665

cgg ctt cta aaa gta gca ata tat cct gga aat gtc ctt act ctg caa      2188
Arg Leu Leu Lys Val Ala Ile Tyr Pro Gly Asn Val Leu Thr Leu Gln
                670                 675                 680

atg tct aag cct ccg caa ttt cga tac aag agt gga cag tat atg ttt      2236
Met Ser Lys Pro Pro Gln Phe Arg Tyr Lys Ser Gly Gln Tyr Met Phe
            685                 690                 695

gtc cag tgt cca gct gtt tct cca ttc gag tgg cat cca ttt tcc att      2284
Val Gln Cys Pro Ala Val Ser Pro Phe Glu Trp His Pro Phe Ser Ile
        700                 705                 710

act tca gct cct ggg gat gac tac ttg agc att cat atc cga caa ctt      2332
Thr Ser Ala Pro Gly Asp Asp Tyr Leu Ser Ile His Ile Arg Gln Leu
    715                 720                 725

ggt gac tgg act caa gaa ctc aag cga gtg ttt tcc gag gct tgc gag      2380
Gly Asp Trp Thr Gln Glu Leu Lys Arg Val Phe Ser Glu Ala Cys Glu
730                 735                 740                 745

cag cca gag gct gga aag agt ggc ctg ctc aga gct gac gaa aac acc      2428
Gln Pro Glu Ala Gly Lys Ser Gly Leu Leu Arg Ala Asp Glu Asn Thr
                750                 755                 760

aaa aca agt ttg cca aag cta tta ata gat gga cct tat gga gct cca      2476
Lys Thr Ser Leu Pro Lys Leu Leu Ile Asp Gly Pro Tyr Gly Ala Pro
            765                 770                 775

gca caa gat tac cgg aag tat gat gtc tta ctg ctt gtt ggt ctt ggc      2524
Ala Gln Asp Tyr Arg Lys Tyr Asp Val Leu Leu Leu Val Gly Leu Gly
        780                 785                 790

att gga gca act ccc ttt ata agt atc ctg aaa gac ttg ctc aaa aac      2572
Ile Gly Ala Thr Pro Phe Ile Ser Ile Leu Lys Asp Leu Leu Lys Asn
    795                 800                 805

atc gtc gca atg gag gag caa gca gat tta gtc tcg gat ttc agt gga      2620
Ile Val Ala Met Glu Glu Gln Ala Asp Leu Val Ser Asp Phe Ser Gly
810                 815                 820                 825

aac tcg gac atg agt gct gca aca agt gaa caa cca gct ctc aac aag      2668
Asn Ser Asp Met Ser Ala Ala Thr Ser Glu Gln Pro Ala Leu Asn Lys
                830                 835                 840

att tct cca aaa aag aga aag agt act cta aaa acc aca aat gca tat      2716
Ile Ser Pro Lys Lys Arg Lys Ser Thr Leu Lys Thr Thr Asn Ala Tyr
            845                 850                 855
```

```
ttt tat tgg gtg acc cgg gag caa gga tca ttt gat tgg ttc aaa ggt     2764
Phe Tyr Trp Val Thr Arg Glu Gln Gly Ser Phe Asp Trp Phe Lys Gly
        860                 865                 870

gtt atg aat gaa gtg gct gaa ctt gat caa agg ggt gtc atc gag atg     2812
Val Met Asn Glu Val Ala Glu Leu Asp Gln Arg Gly Val Ile Glu Met
    875                 880                 885

cat aac tac ttg acg agt gtt tat gag gaa ggg gat gca cgt tca gct     2860
His Asn Tyr Leu Thr Ser Val Tyr Glu Glu Gly Asp Ala Arg Ser Ala
890                 895                 900                 905

ctc att acc atg gtc cag gca ctt aac cat gct aag aat ggg gtt gat     2908
Leu Ile Thr Met Val Gln Ala Leu Asn His Ala Lys Asn Gly Val Asp
                910                 915                 920

att gta tca ggc acc agt gtg agg aca cat ttc gcc agg ccg aat tgg     2956
Ile Val Ser Gly Thr Ser Val Arg Thr His Phe Ala Arg Pro Asn Trp
            925                 930                 935

agg aaa gta ttt tcc aag acc tta acc aag cat gca aat gca aga ata     3004
Arg Lys Val Phe Ser Lys Thr Leu Thr Lys His Ala Asn Ala Arg Ile
        940                 945                 950

gga gtt ttc tac tgt ggt gca ccc ata tta gct aaa gaa ctc agc caa     3052
Gly Val Phe Tyr Cys Gly Ala Pro Ile Leu Ala Lys Glu Leu Ser Gln
    955                 960                 965

ctc tgc aaa gag ttt aac caa aag ggc aca aca aag ttc gag ttt cac     3100
Leu Cys Lys Glu Phe Asn Gln Lys Gly Thr Thr Lys Phe Glu Phe His
970                 975                 980                 985

aaa gaa cat ttt tagaagggcc tggagtatga ttaatcttgc atcaacggta        3152
Lys Glu His Phe

cacacatcta tcttcggtac cttatttgat tattctactg aagagataac attagtaagg   3212

aataagtcag agataaattg tacataatag ggaagaagac tatttcaaga gaaaatacat   3272

accaataaga tgtgaaaaaa aaaaaaaaaa aaaaactcgt gccg                    3316


<210> SEQ ID NO 10
<211> LENGTH: 989
<212> TYPE: PRT
<213> ORGANISM: Lycopersicon esculentum

<400> SEQUENCE: 10

Met Arg Gly Leu Pro Gly His Glu Arg Arg Trp Thr Ser Asp Thr Val
  1               5                  10                  15

Ser Ser Gly Lys Asp Leu Ser Gly Glu Ser Ser Pro Gly Thr Asp Ser
             20                  25                  30

Gly Asn Ile Ser Gly Phe Ala Ser Glu Glu Phe Val Glu Val Ile Leu
         35                  40                  45

Asp Leu Gln Asp Asp Asp Thr Ile Ile Leu Arg Ser Val Glu Pro Ala
     50                  55                  60

Thr Val Ile Asn Ile Asp Gly Ser Asp Pro Ala Ser Gly Val Gly Ile
 65                  70                  75                  80

Gly Gly Ala Ser Ile Glu Thr Pro Ala Ser Val Thr Ser Thr Ser Glu
                 85                  90                  95

Thr Arg Ser Pro Met Met Arg Arg Ser Thr Ser Asn Lys Phe Arg Gln
            100                 105                 110

Phe Ser Gln Glu Leu Lys Ala Glu Ala Val Ala Lys Ala Lys His Phe
        115                 120                 125

Ser Gln Glu Leu Lys Ala Glu Leu Arg Arg Phe Ser Trp Ser His Gly
    130                 135                 140

His Ala Ser Arg Ala Phe Ser Pro Ala Ser Phe Phe Gln Asn Ala Val
145                 150                 155                 160

Val Gly Thr Gly Asn Gly Val Asp Ser Ala Leu Ala Ala Arg Ala Leu
```

-continued

```
                165                 170                 175

Arg Arg Gln Arg Ala Gln Leu Asp Arg Thr Arg Ser Ser Ala His Lys
            180                 185                 190

Ala Leu Arg Gly Leu Lys Phe Ile Ser Asn Asn Lys Thr Asn Gly Trp
        195                 200                 205

Asn Glu Val Glu Asn Asn Phe Ala Lys Leu Ala Lys Asp Gly Tyr Leu
    210                 215                 220

Tyr Arg Ser Asp Phe Ala Gln Cys Ile Gly Gln Tyr Ser Arg Arg Arg
225                 230                 235                 240

Ser Leu Gln Phe Asn Tyr Arg Leu Ile Thr Leu Ile Leu Ile Asn Tyr
                245                 250                 255

Leu Val Lys Gly Met Lys Asp Ser Lys Glu Phe Ala Leu Glu Leu Phe
            260                 265                 270

Asp Ala Leu Ser Arg Arg Arg Arg Leu Lys Val Asp Lys Ile Ser Gln
        275                 280                 285

Glu Glu Leu Tyr Glu Tyr Trp Ser Gln Ile Thr Asp Gln Ser Phe Asp
    290                 295                 300

Ser Arg Leu Gln Ile Phe Phe Asp Met Val Asp Lys Asn Glu Asp Gly
305                 310                 315                 320

Arg Ile Gly Glu Glu Glu Val Lys Glu Ile Ile Met Leu Ser Ala Ser
                325                 330                 335

Ala Asn Lys Leu Ser Arg Leu Lys Glu Gln Ala Glu Glu Tyr Ala Ala
            340                 345                 350

Leu Ile Met Glu Glu Leu Asp Pro Glu Arg Leu Gly Tyr Ile Glu Leu
        355                 360                 365

Trp Gln Leu Glu Thr Leu Leu Leu Gln Lys Asp Thr Tyr Leu Asn Tyr
    370                 375                 380

Ser Gln Ala Leu Ser Tyr Thr Ser Gln Ala Leu Ser Gln Asn Leu Gln
385                 390                 395                 400

Gly Leu Arg Lys Arg Ser Pro Ile Arg Arg Met Ser Thr Lys Leu Val
                405                 410                 415

Tyr Ser Leu Gln Glu Asn Trp Lys Arg Ile Trp Val Leu Val Leu Trp
            420                 425                 430

Ile Leu Ile Met Ile Gly Leu Phe Leu Trp Lys Phe Tyr Gln Tyr Lys
        435                 440                 445

Gln Lys Ser Ala Phe Gln Val Met Gly Tyr Cys Leu Leu Thr Ala Lys
    450                 455                 460

Gly Ala Ala Glu Thr Leu Lys Phe Asn Met Ala Leu Ile Leu Leu Pro
465                 470                 475                 480

Val Cys Arg Asn Thr Ile Thr Phe Leu Arg Ser Thr Lys Leu Ser Cys
                485                 490                 495

Phe Val Pro Phe Asp Asp Asn Ile Asn Phe His Lys Thr Val Ala Ala
            500                 505                 510

Ala Ile Val Thr Gly Ile Ile Leu His Ala Gly Asn His Leu Val Cys
        515                 520                 525

Asp Phe Pro Lys Leu Ile His Ala Asn Ser Thr Asn Tyr Gln Lys Tyr
    530                 535                 540

Leu Val Asn Asp Phe Gly Pro Ser Gln Pro Gln Tyr Ile Asp Leu Val
545                 550                 555                 560

Lys Gly Val Glu Gly Val Thr Gly Ile Val Met Val Ile Leu Met Ala
                565                 570                 575

Ile Ala Phe Thr Leu Ala Thr Arg Trp Phe Arg Arg Ser Leu Ile Lys
            580                 585                 590
```

```
Leu Pro Lys Pro Phe Asp Arg Leu Thr Gly Phe Asn Ala Phe Trp Tyr
        595                 600                 605

Ser His His Leu Leu Ile Ile Val Tyr Ile Val Leu Ile Ile His Gly
    610                 615                 620

Thr Phe Leu Tyr Leu Val His Asn Trp Tyr Ser Lys Thr Thr Trp Met
625                 630                 635                 640

Tyr Ile Ala Val Pro Val Leu Leu Tyr Ala Gly Glu Arg Thr Leu Arg
                645                 650                 655

Phe Phe Arg Ser Gly Leu Tyr Ser Val Arg Leu Leu Lys Val Ala Ile
            660                 665                 670

Tyr Pro Gly Asn Val Leu Thr Leu Gln Met Ser Lys Pro Pro Gln Phe
        675                 680                 685

Arg Tyr Lys Ser Gly Gln Tyr Met Phe Val Gln Cys Pro Ala Val Ser
    690                 695                 700

Pro Phe Glu Trp His Pro Phe Ser Ile Thr Ser Ala Pro Gly Asp Asp
705                 710                 715                 720

Tyr Leu Ser Ile His Ile Arg Gln Leu Gly Asp Trp Thr Gln Glu Leu
                725                 730                 735

Lys Arg Val Phe Ser Glu Ala Cys Glu Gln Pro Glu Ala Gly Lys Ser
            740                 745                 750

Gly Leu Leu Arg Ala Asp Glu Asn Thr Lys Thr Ser Leu Pro Lys Leu
        755                 760                 765

Leu Ile Asp Gly Pro Tyr Gly Ala Pro Ala Gln Asp Tyr Arg Lys Tyr
    770                 775                 780

Asp Val Leu Leu Leu Val Gly Leu Gly Ile Gly Ala Thr Pro Phe Ile
785                 790                 795                 800

Ser Ile Leu Lys Asp Leu Leu Lys Asn Ile Val Ala Met Glu Glu Gln
                805                 810                 815

Ala Asp Leu Val Ser Asp Phe Ser Gly Asn Ser Asp Met Ser Ala Ala
            820                 825                 830

Thr Ser Glu Gln Pro Ala Leu Asn Lys Ile Ser Pro Lys Lys Arg Lys
        835                 840                 845

Ser Thr Leu Lys Thr Thr Asn Ala Tyr Phe Tyr Trp Val Thr Arg Glu
    850                 855                 860

Gln Gly Ser Phe Asp Trp Phe Lys Gly Val Met Asn Glu Val Ala Glu
865                 870                 875                 880

Leu Asp Gln Arg Gly Val Ile Glu Met His Asn Tyr Leu Thr Ser Val
                885                 890                 895

Tyr Glu Glu Gly Asp Ala Arg Ser Ala Leu Ile Thr Met Val Gln Ala
            900                 905                 910

Leu Asn His Ala Lys Asn Gly Val Asp Ile Val Ser Gly Thr Ser Val
        915                 920                 925

Arg Thr His Phe Ala Arg Pro Asn Trp Arg Lys Val Phe Ser Lys Thr
    930                 935                 940

Leu Thr Lys His Ala Asn Ala Arg Ile Gly Val Phe Tyr Cys Gly Ala
945                 950                 955                 960

Pro Ile Leu Ala Lys Glu Leu Ser Gln Leu Cys Lys Glu Phe Asn Gln
                965                 970                 975

Lys Gly Thr Thr Lys Phe Glu Phe His Lys Glu His Phe
            980                 985
```

<210> SEQ ID NO 11
<211> LENGTH: 3080
<212> TYPE: DNA
<213> ORGANISM: Arabidopsis thaliana

```
<220> FEATURE:
<221> NAME/KEY: CDS
<222> LOCATION: (15)..(2846)
<223> OTHER INFORMATION: coding for NADPH oxidase

<400> SEQUENCE: 11

ccgactttgg atct atg aaa ccg ttc tca aag aac gat cgg cga cgg tgg      50
                Met Lys Pro Phe Ser Lys Asn Asp Arg Arg Arg Trp
                1               5                   10

tca ttt gat tca gtt tcc gcc gga aaa acc gcc gtc gga agt gca tca      98
Ser Phe Asp Ser Val Ser Ala Gly Lys Thr Ala Val Gly Ser Ala Ser
        15                  20                  25

act tca ccg gga act gaa tac tcc att aac ggt gat caa gag ttc gtt     146
Thr Ser Pro Gly Thr Glu Tyr Ser Ile Asn Gly Asp Gln Glu Phe Val
    30                  35                  40

gaa gtc aca atc gat ctt caa gac gat gac aca atc gtt ctt cgt agc     194
Glu Val Thr Ile Asp Leu Gln Asp Asp Asp Thr Ile Val Leu Arg Ser
45                  50                  55                  60

gtc gag cca gca acc gcc att aat gtc atc gga gat atc tcc gac gac     242
Val Glu Pro Ala Thr Ala Ile Asn Val Ile Gly Asp Ile Ser Asp Asp
                65                  70                  75

aac acc gga ata atg act ccg gtt tcg att tcg aga tct ccg acg atg     290
Asn Thr Gly Ile Met Thr Pro Val Ser Ile Ser Arg Ser Pro Thr Met
            80                  85                  90

aaa cga act tca tct aat cgg ttc cga caa ttc tca caa gag ctt aaa     338
Lys Arg Thr Ser Ser Asn Arg Phe Arg Gln Phe Ser Gln Glu Leu Lys
        95                  100                 105

gcc gaa gct gtg gcg aaa gcg aaa cag tta tct cag gag ttg aaa cga     386
Ala Glu Ala Val Ala Lys Ala Lys Gln Leu Ser Gln Glu Leu Lys Arg
    110                 115                 120

ttc tca tgg tct cgt tct ttc tca ggt aac tta acc act act agt acc     434
Phe Ser Trp Ser Arg Ser Phe Ser Gly Asn Leu Thr Thr Thr Ser Thr
125                 130                 135                 140

gcc gct aat caa agc ggc ggt gct ggt ggt ggt ttg gtg aac tcg gct     482
Ala Ala Asn Gln Ser Gly Gly Ala Gly Gly Gly Leu Val Asn Ser Ala
                145                 150                 155

tta gaa gcg cga gcg ttg cga aag caa cgt gct cag tta gat cgg act     530
Leu Glu Ala Arg Ala Leu Arg Lys Gln Arg Ala Gln Leu Asp Arg Thr
            160                 165                 170

cgg tct agt gct caa aga gct ctt cgt ggt ttg aga ttc att agc aat     578
Arg Ser Ser Ala Gln Arg Ala Leu Arg Gly Leu Arg Phe Ile Ser Asn
        175                 180                 185

aag caa aag aac gtt gat ggt tgg aac gat gtt caa tca aat ttc gaa     626
Lys Gln Lys Asn Val Asp Gly Trp Asn Asp Val Gln Ser Asn Phe Glu
    190                 195                 200

aaa ttc gaa aaa aat ggt tac atc tat cgc tcc gat ttc gct caa tgc     674
Lys Phe Glu Lys Asn Gly Tyr Ile Tyr Arg Ser Asp Phe Ala Gln Cys
205                 210                 215                 220

ata gga atg aaa gat tcg aaa gaa ttt gca ttg gaa ctg ttc gat gca     722
Ile Gly Met Lys Asp Ser Lys Glu Phe Ala Leu Glu Leu Phe Asp Ala
                225                 230                 235

ttg agt aga aga aga aga tta aaa gta gag aaa atc aat cac gat gag     770
Leu Ser Arg Arg Arg Arg Leu Lys Val Glu Lys Ile Asn His Asp Glu
            240                 245                 250

ctt tat gag tat tgg tca caa atc aac gac gag agt ttt gat tct cgt     818
Leu Tyr Glu Tyr Trp Ser Gln Ile Asn Asp Glu Ser Phe Asp Ser Arg
        255                 260                 265

ctc cag atc ttc ttc gac ata gtg gac aag aat gaa gat ggg aga att     866
Leu Gln Ile Phe Phe Asp Ile Val Asp Lys Asn Glu Asp Gly Arg Ile
    270                 275                 280

aca gaa gag gaa gta aaa gag ata ata atg ttg agt gca tct gca aat     914
```

```
Thr Glu Glu Glu Val Lys Glu Ile Ile Met Leu Ser Ala Ser Ala Asn
285                 290                 295                 300

aag cta tca aga tta aag gaa caa gca gag gaa tat gca gct ttg att      962
Lys Leu Ser Arg Leu Lys Glu Gln Ala Glu Glu Tyr Ala Ala Leu Ile
                305                 310                 315

atg gaa gag tta gat cct gaa aga ctt ggc tac ata gag cta tgg caa     1010
Met Glu Glu Leu Asp Pro Glu Arg Leu Gly Tyr Ile Glu Leu Trp Gln
            320                 325                 330

cta gag act ttg ctt cta caa aaa gac aca tac ctc aat tac agt caa     1058
Leu Glu Thr Leu Leu Leu Gln Lys Asp Thr Tyr Leu Asn Tyr Ser Gln
        335                 340                 345

gca ttg agc tat acg agc caa gca ttg agc caa aac ctt caa ggg tta     1106
Ala Leu Ser Tyr Thr Ser Gln Ala Leu Ser Gln Asn Leu Gln Gly Leu
    350                 355                 360

agg gga aag agt cga ata cat aga atg agt tcg gat ttc gtc tac att     1154
Arg Gly Lys Ser Arg Ile His Arg Met Ser Ser Asp Phe Val Tyr Ile
365                 370                 375                 380

atg caa gag aat tgg aaa agg ata tgg gtt tta tcc tta tgg atc atg     1202
Met Gln Glu Asn Trp Lys Arg Ile Trp Val Leu Ser Leu Trp Ile Met
                385                 390                 395

atc atg atc gga tta ttc ttg tgg aaa ttc ttc caa tac aag caa aaa     1250
Ile Met Ile Gly Leu Phe Leu Trp Lys Phe Phe Gln Tyr Lys Gln Lys
            400                 405                 410

gat gca ttt cat gtg atg gga tat tgt tta ctc aca gcc aaa gga gca     1298
Asp Ala Phe His Val Met Gly Tyr Cys Leu Leu Thr Ala Lys Gly Ala
        415                 420                 425

gct gaa aca ctt aaa ttc aac atg gct cta ata ctt ttc cca gtt tgc     1346
Ala Glu Thr Leu Lys Phe Asn Met Ala Leu Ile Leu Phe Pro Val Cys
    430                 435                 440

aga aac acc att act tgg ctt aga tcc aca aga ctc tct tac ttc gtt     1394
Arg Asn Thr Ile Thr Trp Leu Arg Ser Thr Arg Leu Ser Tyr Phe Val
445                 450                 455                 460

cct ttt gat gat aat atc aac ttc cac aag aca att gct gga gcc att     1442
Pro Phe Asp Asp Asn Ile Asn Phe His Lys Thr Ile Ala Gly Ala Ile
                465                 470                 475

gta gta gct gtg atc ctt cat att gga gac cat ctt gct tgt gat ttc     1490
Val Val Ala Val Ile Leu His Ile Gly Asp His Leu Ala Cys Asp Phe
            480                 485                 490

cct aga att gtt aga gcc acc gaa tac gat tac aat cgg tat ctg ttt     1538
Pro Arg Ile Val Arg Ala Thr Glu Tyr Asp Tyr Asn Arg Tyr Leu Phe
        495                 500                 505

cat tac ttt caa aca aaa cag cca aca tac ttc gac ctc gtt aag gga     1586
His Tyr Phe Gln Thr Lys Gln Pro Thr Tyr Phe Asp Leu Val Lys Gly
    510                 515                 520

cct gaa gga atc act ggg att tta atg gtc att ttg atg att att tca     1634
Pro Glu Gly Ile Thr Gly Ile Leu Met Val Ile Leu Met Ile Ile Ser
525                 530                 535                 540

ttc aca tta gca aca aga tgg ttt agg cgt aac cta gtc aag ctt cct     1682
Phe Thr Leu Ala Thr Arg Trp Phe Arg Arg Asn Leu Val Lys Leu Pro
                545                 550                 555

aag cca ttt gat cga cta acc ggt ttt aac gcc ttt tgg tat tcg cat     1730
Lys Pro Phe Asp Arg Leu Thr Gly Phe Asn Ala Phe Trp Tyr Ser His
            560                 565                 570

cat ttg ttc gtc att gtt tat atc ttg ctt att ctt cat ggt atc ttc     1778
His Leu Phe Val Ile Val Tyr Ile Leu Leu Ile Leu His Gly Ile Phe
        575                 580                 585

ctc tat ttc gcc aag cct tgg tat gtt cgt acg aca tgg atg tat ctt     1826
Leu Tyr Phe Ala Lys Pro Trp Tyr Val Arg Thr Thr Trp Met Tyr Leu
    590                 595                 600

gca gta cca gtt tta ctc tat ggt gga gaa aga aca ctt agg tac ttc     1874
```

```
Ala Val Pro Val Leu Leu Tyr Gly Gly Glu Arg Thr Leu Arg Tyr Phe
605                 610                 615                 620

cgt tct ggt tct tat tcg gtt cga ctg ctt aag gtt gct ata tat cct      1922
Arg Ser Gly Ser Tyr Ser Val Arg Leu Leu Lys Val Ala Ile Tyr Pro
                625                 630                 635

ggt aat gtt cta acg cta caa atg tcg aaa cca act caa ttt cgt tac      1970
Gly Asn Val Leu Thr Leu Gln Met Ser Lys Pro Thr Gln Phe Arg Tyr
            640                 645                 650

aaa agc gga caa tac atg ttt gtc caa tgt cct gcg gtt tcg cca ttc      2018
Lys Ser Gly Gln Tyr Met Phe Val Gln Cys Pro Ala Val Ser Pro Phe
        655                 660                 665

gag tgg cat cca ttc tca att act tcc gca cct gaa gat gat tat atc      2066
Glu Trp His Pro Phe Ser Ile Thr Ser Ala Pro Glu Asp Asp Tyr Ile
    670                 675                 680

agc att cac att aga caa ctt ggt gat tgg act caa gaa ctc aaa aga      2114
Ser Ile His Ile Arg Gln Leu Gly Asp Trp Thr Gln Glu Leu Lys Arg
685                 690                 695                 700

gta ttc tct gaa gtt tgt gag cca ccg gtt ggc ggt aaa agc gga ctt      2162
Val Phe Ser Glu Val Cys Glu Pro Pro Val Gly Gly Lys Ser Gly Leu
                705                 710                 715

ctc aga gcc gac gaa aca aca aag aaa agt ttg cca aag cta ttg ata      2210
Leu Arg Ala Asp Glu Thr Thr Lys Lys Ser Leu Pro Lys Leu Leu Ile
            720                 725                 730

gat gga ccg tac ggt gca cca gca caa gat tat agg aaa tat gat gtt      2258
Asp Gly Pro Tyr Gly Ala Pro Ala Gln Asp Tyr Arg Lys Tyr Asp Val
        735                 740                 745

ctc tta tta gtt ggt ctt ggc att ggt gca act cca ttt atc agt atc      2306
Leu Leu Leu Val Gly Leu Gly Ile Gly Ala Thr Pro Phe Ile Ser Ile
    750                 755                 760

ttg aaa gat ttg ctt aac aac att gtt aaa atg gaa gag cat gcg gat      2354
Leu Lys Asp Leu Leu Asn Asn Ile Val Lys Met Glu Glu His Ala Asp
765                 770                 775                 780

tcg atc tcg gat ttc agt aga tca tca gaa tac agc aca gga agc aac      2402
Ser Ile Ser Asp Phe Ser Arg Ser Ser Glu Tyr Ser Thr Gly Ser Asn
                785                 790                 795

ggt gac acg cca aga cga aag aga ata cta aaa acc aca aat gct tat      2450
Gly Asp Thr Pro Arg Arg Lys Arg Ile Leu Lys Thr Thr Asn Ala Tyr
            800                 805                 810

ttc tac tgg gtc aca aga gaa caa ggc tct ttt gat tgg ttc aaa ggt      2498
Phe Tyr Trp Val Thr Arg Glu Gln Gly Ser Phe Asp Trp Phe Lys Gly
        815                 820                 825

gtc atg aac gaa gtt gca gaa ctt gac caa cgg ggt gtg ata gag atg      2546
Val Met Asn Glu Val Ala Glu Leu Asp Gln Arg Gly Val Ile Glu Met
    830                 835                 840

cat aac tat tta aca agt gtg tat gaa gaa ggt gat gct cgt tct gct      2594
His Asn Tyr Leu Thr Ser Val Tyr Glu Glu Gly Asp Ala Arg Ser Ala
845                 850                 855                 860

ctc att aca atg gtt caa gct ctt aat cat gcc aaa aat ggt gtc gac      2642
Leu Ile Thr Met Val Gln Ala Leu Asn His Ala Lys Asn Gly Val Asp
                865                 870                 875

att gtc tct ggc act agg gtc aga aca cac ttt gca aga cct aat tgg      2690
Ile Val Ser Gly Thr Arg Val Arg Thr His Phe Ala Arg Pro Asn Trp
            880                 885                 890

aag aag gtt ctc aca aag cta agt tcc aag cat tgc aat gca aga aca      2738
Lys Lys Val Leu Thr Lys Leu Ser Ser Lys His Cys Asn Ala Arg Thr
        895                 900                 905

gga gtg ttt tat tgc gga gta ccg gtt tta ggg aag gag ctt agc aaa      2786
Gly Val Phe Tyr Cys Gly Val Pro Val Leu Gly Lys Glu Leu Ser Lys
    910                 915                 920

cta tgc aac aca ttc aat caa aaa ggt tca acc aag ttt gaa ttt cac      2834
```

```
Leu Cys Asn Thr Phe Asn Gln Lys Gly Ser Thr Lys Phe Glu Phe His
925                 930                 935                 940

aag gag cat ttc taaaagacaa gaaggaagaa gccaaaagcc ctctagattc        2886
Lys Glu His Phe

tttaatatct caaatttagc cacttatagt ataaaggcaa tctcttcact atttaattca   2946

aagtgattaa acgttaacac actgtcaaaa gtgagtgtgt taacgtttag ctccacacgt   3006

tctaggttta tatacaccga ggcatacgtg taaatatacg agacagaaga aattcaaggg   3066

ggtttgatag aagc                                                     3080


<210> SEQ ID NO 12
<211> LENGTH: 944
<212> TYPE: PRT
<213> ORGANISM: Arabidopsis thaliana

<400> SEQUENCE: 12

Met Lys Pro Phe Ser Lys Asn Asp Arg Arg Arg Trp Ser Phe Asp Ser
  1               5                  10                  15

Val Ser Ala Gly Lys Thr Ala Val Gly Ser Ala Ser Thr Ser Pro Gly
             20                  25                  30

Thr Glu Tyr Ser Ile Asn Gly Asp Gln Glu Phe Val Glu Val Thr Ile
         35                  40                  45

Asp Leu Gln Asp Asp Asp Thr Ile Val Leu Arg Ser Val Glu Pro Ala
     50                  55                  60

Thr Ala Ile Asn Val Ile Gly Asp Ile Ser Asp Asp Asn Thr Gly Ile
 65                  70                  75                  80

Met Thr Pro Val Ser Ile Ser Arg Ser Pro Thr Met Lys Arg Thr Ser
                 85                  90                  95

Ser Asn Arg Phe Arg Gln Phe Ser Gln Glu Leu Lys Ala Glu Ala Val
            100                 105                 110

Ala Lys Ala Lys Gln Leu Ser Gln Glu Leu Lys Arg Phe Ser Trp Ser
        115                 120                 125

Arg Ser Phe Ser Gly Asn Leu Thr Thr Thr Ser Thr Ala Ala Asn Gln
    130                 135                 140

Ser Gly Gly Ala Gly Gly Gly Leu Val Asn Ser Ala Leu Glu Ala Arg
145                 150                 155                 160

Ala Leu Arg Lys Gln Arg Ala Gln Leu Asp Arg Thr Arg Ser Ser Ala
                165                 170                 175

Gln Arg Ala Leu Arg Gly Leu Arg Phe Ile Ser Asn Lys Gln Lys Asn
            180                 185                 190

Val Asp Gly Trp Asn Asp Val Gln Ser Asn Phe Glu Lys Phe Glu Lys
        195                 200                 205

Asn Gly Tyr Ile Tyr Arg Ser Asp Phe Ala Gln Cys Ile Gly Met Lys
    210                 215                 220

Asp Ser Lys Glu Phe Ala Leu Glu Leu Phe Asp Ala Leu Ser Arg Arg
225                 230                 235                 240

Arg Arg Leu Lys Val Glu Lys Ile Asn His Asp Glu Leu Tyr Glu Tyr
                245                 250                 255

Trp Ser Gln Ile Asn Asp Glu Ser Phe Asp Ser Arg Leu Gln Ile Phe
            260                 265                 270

Phe Asp Ile Val Asp Lys Asn Glu Asp Gly Arg Ile Thr Glu Glu Glu
        275                 280                 285

Val Lys Glu Ile Ile Met Leu Ser Ala Ser Ala Asn Lys Leu Ser Arg
    290                 295                 300

Leu Lys Glu Gln Ala Glu Glu Tyr Ala Ala Leu Ile Met Glu Glu Leu
```

```
305                 310                 315                 320

Asp Pro Glu Arg Leu Gly Tyr Ile Glu Leu Trp Gln Leu Glu Thr Leu
                325                 330                 335

Leu Leu Gln Lys Asp Thr Tyr Leu Asn Tyr Ser Gln Ala Leu Ser Tyr
            340                 345                 350

Thr Ser Gln Ala Leu Ser Gln Asn Leu Gln Gly Leu Arg Gly Lys Ser
        355                 360                 365

Arg Ile His Arg Met Ser Ser Asp Phe Val Tyr Ile Met Gln Glu Asn
    370                 375                 380

Trp Lys Arg Ile Trp Val Leu Ser Leu Trp Ile Met Ile Met Ile Gly
385                 390                 395                 400

Leu Phe Leu Trp Lys Phe Phe Gln Tyr Lys Gln Lys Asp Ala Phe His
                405                 410                 415

Val Met Gly Tyr Cys Leu Leu Thr Ala Lys Gly Ala Ala Glu Thr Leu
            420                 425                 430

Lys Phe Asn Met Ala Leu Ile Leu Phe Pro Val Cys Arg Asn Thr Ile
        435                 440                 445

Thr Trp Leu Arg Ser Thr Arg Leu Ser Tyr Phe Val Pro Phe Asp Asp
    450                 455                 460

Asn Ile Asn Phe His Lys Thr Ile Ala Gly Ala Ile Val Val Ala Val
465                 470                 475                 480

Ile Leu His Ile Gly Asp His Leu Ala Cys Asp Phe Pro Arg Ile Val
                485                 490                 495

Arg Ala Thr Glu Tyr Asp Tyr Asn Arg Tyr Leu Phe His Tyr Phe Gln
            500                 505                 510

Thr Lys Gln Pro Thr Tyr Phe Asp Leu Val Lys Gly Pro Glu Gly Ile
        515                 520                 525

Thr Gly Ile Leu Met Val Ile Leu Met Ile Ile Ser Phe Thr Leu Ala
    530                 535                 540

Thr Arg Trp Phe Arg Arg Asn Leu Val Lys Leu Pro Lys Pro Phe Asp
545                 550                 555                 560

Arg Leu Thr Gly Phe Asn Ala Phe Trp Tyr Ser His His Leu Phe Val
                565                 570                 575

Ile Val Tyr Ile Leu Leu Ile Leu His Gly Ile Phe Leu Tyr Phe Ala
            580                 585                 590

Lys Pro Trp Tyr Val Arg Thr Thr Trp Met Tyr Leu Ala Val Pro Val
        595                 600                 605

Leu Leu Tyr Gly Gly Glu Arg Thr Leu Arg Tyr Phe Arg Ser Gly Ser
    610                 615                 620

Tyr Ser Val Arg Leu Leu Lys Val Ala Ile Tyr Pro Gly Asn Val Leu
625                 630                 635                 640

Thr Leu Gln Met Ser Lys Pro Thr Gln Phe Arg Tyr Lys Ser Gly Gln
                645                 650                 655

Tyr Met Phe Val Gln Cys Pro Ala Val Ser Pro Phe Glu Trp His Pro
            660                 665                 670

Phe Ser Ile Thr Ser Ala Pro Glu Asp Asp Tyr Ile Ser Ile His Ile
        675                 680                 685

Arg Gln Leu Gly Asp Trp Thr Gln Glu Leu Lys Arg Val Phe Ser Glu
    690                 695                 700

Val Cys Glu Pro Pro Val Gly Gly Lys Ser Gly Leu Leu Arg Ala Asp
705                 710                 715                 720

Glu Thr Thr Lys Lys Ser Leu Pro Lys Leu Leu Ile Asp Gly Pro Tyr
                725                 730                 735
```

```
Gly Ala Pro Ala Gln Asp Tyr Arg Lys Tyr Asp Val Leu Leu Leu Val
            740                 745                 750

Gly Leu Gly Ile Gly Ala Thr Pro Phe Ile Ser Ile Leu Lys Asp Leu
        755                 760                 765

Leu Asn Asn Ile Val Lys Met Glu Glu His Ala Asp Ser Ile Ser Asp
    770                 775                 780

Phe Ser Arg Ser Ser Glu Tyr Ser Thr Gly Ser Asn Gly Asp Thr Pro
785                 790                 795                 800

Arg Arg Lys Arg Ile Leu Lys Thr Thr Asn Ala Tyr Phe Tyr Trp Val
                805                 810                 815

Thr Arg Glu Gln Gly Ser Phe Asp Trp Phe Lys Gly Val Met Asn Glu
            820                 825                 830

Val Ala Glu Leu Asp Gln Arg Gly Val Ile Glu Met His Asn Tyr Leu
        835                 840                 845

Thr Ser Val Tyr Glu Glu Gly Asp Ala Arg Ser Ala Leu Ile Thr Met
    850                 855                 860

Val Gln Ala Leu Asn His Ala Lys Asn Gly Val Asp Ile Val Ser Gly
865                 870                 875                 880

Thr Arg Val Arg Thr His Phe Ala Arg Pro Asn Trp Lys Lys Val Leu
                885                 890                 895

Thr Lys Leu Ser Ser Lys His Cys Asn Ala Arg Thr Gly Val Phe Tyr
            900                 905                 910

Cys Gly Val Pro Val Leu Gly Lys Glu Leu Ser Lys Leu Cys Asn Thr
        915                 920                 925

Phe Asn Gln Lys Gly Ser Thr Lys Phe Glu Phe His Lys Glu His Phe
    930                 935                 940


<210> SEQ ID NO 13
<211> LENGTH: 3035
<212> TYPE: DNA
<213> ORGANISM: Arabidopsis thaliana
<220> FEATURE:
<221> NAME/KEY: CDS
<222> LOCATION: (132)..(2894)
<223> OTHER INFORMATION: coding for NADPH oxidase

<400> SEQUENCE: 13

tcaaacacct tttgagagcg gttatttttt ctctatcaac taatacagta accttacggg      60

tgtttatttg tatagatctc tgtggttttc ttggccaact ctagtgagat ctttttcgtt     120

tctcgaattc g atg aaa atg aga cga ggc aat tca agt aac gac cat gaa      170
             Met Lys Met Arg Arg Gly Asn Ser Ser Asn Asp His Glu
               1               5                  10

ctt ggg att cta cga gga gct aac tcg gac acc aac tcg gac acg gag      218
Leu Gly Ile Leu Arg Gly Ala Asn Ser Asp Thr Asn Ser Asp Thr Glu
     15                  20                  25

agc atc gct agc gac cgt ggt gcc ttt agc ggt ccg ctt ggc cgg cct      266
Ser Ile Ala Ser Asp Arg Gly Ala Phe Ser Gly Pro Leu Gly Arg Pro
 30                  35                  40                  45

aaa cgt gcg tcc aag aaa aac gca aga ttc gcc gac gat ctt ccc aag      314
Lys Arg Ala Ser Lys Lys Asn Ala Arg Phe Ala Asp Asp Leu Pro Lys
                 50                  55                  60

aga agc aat agt gtt gct ggc ggc cgt ggt gat gac gat gag tac gtg      362
Arg Ser Asn Ser Val Ala Gly Gly Arg Gly Asp Asp Asp Glu Tyr Val
             65                  70                  75

gag atc acg cta gac atc agg gac gac tcg gtg gcc gtc cat agt gtc      410
Glu Ile Thr Leu Asp Ile Arg Asp Asp Ser Val Ala Val His Ser Val
         80                  85                  90

caa caa gca gct gga ggt gga ggc cac ctg gag gac ccg gag cta gcc      458
```

```
Gln Gln Ala Ala Gly Gly Gly Gly His Leu Glu Asp Pro Glu Leu Ala
     95                 100                 105

ctt ctt acg aag aag act ctc gag agc agc ctc aac aac acc acc tcc      506
Leu Leu Thr Lys Lys Thr Leu Glu Ser Ser Leu Asn Asn Thr Thr Ser
110                 115                 120                 125

tta tct ttc ttc cga agc acc tcc tca cgc atc aag aac gcc tcc cgc      554
Leu Ser Phe Phe Arg Ser Thr Ser Ser Arg Ile Lys Asn Ala Ser Arg
                130                 135                 140

gag ctc cgc cgc gtg ttc tct aga cgt ccc tcc ccg gcc gtg cgg cgg      602
Glu Leu Arg Arg Val Phe Ser Arg Arg Pro Ser Pro Ala Val Arg Arg
            145                 150                 155

ttt gac cgc acg agc tcc gcg gcc atc cac gca ctc aaa ggt ctc aag      650
Phe Asp Arg Thr Ser Ser Ala Ala Ile His Ala Leu Lys Gly Leu Lys
        160                 165                 170

ttc att gcc acc aag acg gcc gca tgg ccg gcc gtc gac caa cgt ttc      698
Phe Ile Ala Thr Lys Thr Ala Ala Trp Pro Ala Val Asp Gln Arg Phe
    175                 180                 185

gat aaa ctc tcc gct gat tcc aac ggc ctc tta ctc tct gcc aag ttt      746
Asp Lys Leu Ser Ala Asp Ser Asn Gly Leu Leu Leu Ser Ala Lys Phe
190                 195                 200                 205

tgg gaa tgc tta gga atg aat aag gaa tct aaa gac ttc gct gac cag      794
Trp Glu Cys Leu Gly Met Asn Lys Glu Ser Lys Asp Phe Ala Asp Gln
                210                 215                 220

ctc ttt aga gca tta gct cgc cgg aat aac gtc tcc ggc gat gca atc      842
Leu Phe Arg Ala Leu Ala Arg Arg Asn Asn Val Ser Gly Asp Ala Ile
            225                 230                 235

aca aag gaa cag ctt agg ata ttc tgg gaa cag atc tca gac gaa agc      890
Thr Lys Glu Gln Leu Arg Ile Phe Trp Glu Gln Ile Ser Asp Glu Ser
        240                 245                 250

ttt gat gcc aaa ctc caa gtc ttt ttt gac atg gtg gac aaa gat gaa      938
Phe Asp Ala Lys Leu Gln Val Phe Phe Asp Met Val Asp Lys Asp Glu
    255                 260                 265

gat ggg cga gta aca gaa gaa gag gtg gct gag att att agt ctt agt      986
Asp Gly Arg Val Thr Glu Glu Glu Val Ala Glu Ile Ile Ser Leu Ser
270                 275                 280                 285

gct tct gca aac aag ctc tca aat att caa aag caa gcc aaa gaa tat     1034
Ala Ser Ala Asn Lys Leu Ser Asn Ile Gln Lys Gln Ala Lys Glu Tyr
                290                 295                 300

gcg gca ctg ata atg gaa gag ttg gac cca gac aat gct ggg ttt att     1082
Ala Ala Leu Ile Met Glu Glu Leu Asp Pro Asp Asn Ala Gly Phe Ile
            305                 310                 315

atg atc gaa aac ttg gaa atg ttg cta tta caa gca ccg aac cag tcg     1130
Met Ile Glu Asn Leu Glu Met Leu Leu Leu Gln Ala Pro Asn Gln Ser
        320                 325                 330

gtg cgg atg gga gac agc agg ata ctt agt cag atg tta agt cag aag     1178
Val Arg Met Gly Asp Ser Arg Ile Leu Ser Gln Met Leu Ser Gln Lys
    335                 340                 345

ctt aga ccg gca aaa gag agc aac cct tta ttg aga tgg tcg gag aaa     1226
Leu Arg Pro Ala Lys Glu Ser Asn Pro Leu Leu Arg Trp Ser Glu Lys
350                 355                 360                 365

atc aaa tat ttc ata ctt gat aat tgg cag aga tta tgg atc atg atg     1274
Ile Lys Tyr Phe Ile Leu Asp Asn Trp Gln Arg Leu Trp Ile Met Met
                370                 375                 380

tta tgg ctt ggc atc tgt ggt ggc ctc ttt act tat aaa ttc att cag     1322
Leu Trp Leu Gly Ile Cys Gly Gly Leu Phe Thr Tyr Lys Phe Ile Gln
            385                 390                 395

tac aag aac aaa gct gcc tat ggt gtg atg ggt tat tgt gtt tgt gtc     1370
Tyr Lys Asn Lys Ala Ala Tyr Gly Val Met Gly Tyr Cys Val Cys Val
        400                 405                 410

gcc aaa gga ggc gcc gag act ctc aaa ttc aac atg gct ctc ata ttg     1418
```

```
Ala Lys Gly Gly Ala Glu Thr Leu Lys Phe Asn Met Ala Leu Ile Leu
    415                 420                 425

ttg cct gtt tgt cga aac acc atc act tgg ctt agg aac aag acc aag     1466
Leu Pro Val Cys Arg Asn Thr Ile Thr Trp Leu Arg Asn Lys Thr Lys
430                 435                 440                 445

ctt ggt act gtc gtt cct ttt gat gat agt ctt aac ttc cac aag gtt     1514
Leu Gly Thr Val Val Pro Phe Asp Asp Ser Leu Asn Phe His Lys Val
                450                 455                 460

att gca agc ggg ata gtc gtc ggt gtt ttg ctc cat gcg ggt gcc cat     1562
Ile Ala Ser Gly Ile Val Val Gly Val Leu Leu His Ala Gly Ala His
            465                 470                 475

tta acg tgt gat ttt cca cgt tta att gcc gcg gat gag gac acc tat     1610
Leu Thr Cys Asp Phe Pro Arg Leu Ile Ala Ala Asp Glu Asp Thr Tyr
        480                 485                 490

gag ccg atg gaa aaa tac ttt ggg gat caa ccg act agc tac tgg tgg     1658
Glu Pro Met Glu Lys Tyr Phe Gly Asp Gln Pro Thr Ser Tyr Trp Trp
    495                 500                 505

ttt gtg aaa gga gtg gaa gga tgg act ggc att gtg atg gtt gtg cta     1706
Phe Val Lys Gly Val Glu Gly Trp Thr Gly Ile Val Met Val Val Leu
510                 515                 520                 525

atg gct ata gcc ttt aca ctc gct acg cct tgg ttc cga cgt aac aag     1754
Met Ala Ile Ala Phe Thr Leu Ala Thr Pro Trp Phe Arg Arg Asn Lys
                530                 535                 540

ctt aac tta cct aac ttc ctc aag aag ctt acc ggt ttc aac gcc ttt     1802
Leu Asn Leu Pro Asn Phe Leu Lys Lys Leu Thr Gly Phe Asn Ala Phe
            545                 550                 555

tgg tac acc cac cat ttg ttc atc att gtt tat gct ctt ctc att gtc     1850
Trp Tyr Thr His His Leu Phe Ile Ile Val Tyr Ala Leu Leu Ile Val
        560                 565                 570

cat ggt atc aag ctc tac ctc aca aag att tgg tat cag aag acg aca     1898
His Gly Ile Lys Leu Tyr Leu Thr Lys Ile Trp Tyr Gln Lys Thr Thr
    575                 580                 585

tgg atg tat ctt gct gta ccc atc ctt cta tat gca tct gag agg ctg     1946
Trp Met Tyr Leu Ala Val Pro Ile Leu Leu Tyr Ala Ser Glu Arg Leu
590                 595                 600                 605

ctc cgt gct ttc aga tca agc atc aaa ccg gtt aag atg atc aag gtg     1994
Leu Arg Ala Phe Arg Ser Ser Ile Lys Pro Val Lys Met Ile Lys Val
                610                 615                 620

gct gtt tac ccc ggg aac gtg ttg tct cta cac atg acg aag cca caa     2042
Ala Val Tyr Pro Gly Asn Val Leu Ser Leu His Met Thr Lys Pro Gln
            625                 630                 635

gga ttc aaa tac aaa agt gga cag ttc atg ttg gtg aac tgc cga gcc     2090
Gly Phe Lys Tyr Lys Ser Gly Gln Phe Met Leu Val Asn Cys Arg Ala
        640                 645                 650

gta tct cca ttc gaa tgg cat cct ttc tca atc aca tca gct ccc gga     2138
Val Ser Pro Phe Glu Trp His Pro Phe Ser Ile Thr Ser Ala Pro Gly
    655                 660                 665

gac gat tac ctg agc gta cat atc cgc act ctc ggt gac tgg aca cgt     2186
Asp Asp Tyr Leu Ser Val His Ile Arg Thr Leu Gly Asp Trp Thr Arg
670                 675                 680                 685

aag ctc agg acc gtt ttc tcc gag gtt tgc aaa cct cct acc gcc ggt     2234
Lys Leu Arg Thr Val Phe Ser Glu Val Cys Lys Pro Pro Thr Ala Gly
                690                 695                 700

aaa agc ggt ctt ctc cga gca gac gga gga gat gga aac ctc ccg ttc     2282
Lys Ser Gly Leu Leu Arg Ala Asp Gly Gly Asp Gly Asn Leu Pro Phe
            705                 710                 715

ccg aag gtc ctt atc gac ggt cca tac ggt gct ccc gca caa gac tac     2330
Pro Lys Val Leu Ile Asp Gly Pro Tyr Gly Ala Pro Ala Gln Asp Tyr
        720                 725                 730

aag aaa tac gac gtg gta ctc ctc gta ggt ctc ggc att gga gcc acg     2378
```

```
Lys Lys Tyr Asp Val Val Leu Leu Val Gly Leu Gly Ile Gly Ala Thr
    735                 740                 745

cct atg atc agt atc ctt aag gac atc atc aac aac atg aaa ggt cct     2426
Pro Met Ile Ser Ile Leu Lys Asp Ile Ile Asn Asn Met Lys Gly Pro
750                 755                 760                 765

gac cgc gac agc gac att gag aac aat aac agt aac aac aat agt aaa     2474
Asp Arg Asp Ser Asp Ile Glu Asn Asn Asn Ser Asn Asn Asn Ser Lys
                770                 775                 780

ggg ttt aag aca agg aaa gct tat ttc tac tgg gtg act agg gaa caa     2522
Gly Phe Lys Thr Arg Lys Ala Tyr Phe Tyr Trp Val Thr Arg Glu Gln
            785                 790                 795

gga tca ttc gag tgg ttc aag gga ata atg gac gag att tcg gag tta     2570
Gly Ser Phe Glu Trp Phe Lys Gly Ile Met Asp Glu Ile Ser Glu Leu
        800                 805                 810

gac gag gaa gga atc atc gag ctt cac aat tat tgc acg agt gtg tac     2618
Asp Glu Glu Gly Ile Ile Glu Leu His Asn Tyr Cys Thr Ser Val Tyr
    815                 820                 825

gag gaa ggt gat gca aga gtg gct ctc att gcc atg ctt cag tcg ttg     2666
Glu Glu Gly Asp Ala Arg Val Ala Leu Ile Ala Met Leu Gln Ser Leu
830                 835                 840                 845

caa cac gct aag aac ggt gtg gat gtt gtg tcg ggt aca cgt gtc aag     2714
Gln His Ala Lys Asn Gly Val Asp Val Val Ser Gly Thr Arg Val Lys
                850                 855                 860

tcc cac ttc gct aaa cct aac tgg aga caa gtc tac aag aag atc gct     2762
Ser His Phe Ala Lys Pro Asn Trp Arg Gln Val Tyr Lys Lys Ile Ala
            865                 870                 875

gtt caa cat ccc ggc aaa aga ata gga gtc ttc tac tgt gga atg cca     2810
Val Gln His Pro Gly Lys Arg Ile Gly Val Phe Tyr Cys Gly Met Pro
        880                 885                 890

gga atg ata aag gaa tta aaa aat cta gct ttg gat ttt tct cga aag     2858
Gly Met Ile Lys Glu Leu Lys Asn Leu Ala Leu Asp Phe Ser Arg Lys
    895                 900                 905

aca act acc aag ttt gac ttc cac aaa gag aac ttc tagattaatt         2904
Thr Thr Thr Lys Phe Asp Phe His Lys Glu Asn Phe
910                 915                 920

atatacgttg tagaaaaata aaacaagaaa caactataca aataaatatt tattttaaat   2964

tcttttcatt ttatgtaaaa ttatctgagt tatctttttt tgttaaaaaa aaaaaaaaaa   3024

aaaaaaaaaa a                                                        3035


<210> SEQ ID NO 14
<211> LENGTH: 921
<212> TYPE: PRT
<213> ORGANISM: Arabidopsis thaliana

<400> SEQUENCE: 14

Met Lys Met Arg Arg Gly Asn Ser Ser Asn Asp His Glu Leu Gly Ile
  1               5                  10                  15

Leu Arg Gly Ala Asn Ser Asp Thr Asn Ser Asp Thr Glu Ser Ile Ala
             20                  25                  30

Ser Asp Arg Gly Ala Phe Ser Gly Pro Leu Gly Arg Pro Lys Arg Ala
         35                  40                  45

Ser Lys Lys Asn Ala Arg Phe Ala Asp Asp Leu Pro Lys Arg Ser Asn
     50                  55                  60

Ser Val Ala Gly Gly Arg Gly Asp Asp Asp Glu Tyr Val Glu Ile Thr
 65                  70                  75                  80

Leu Asp Ile Arg Asp Asp Ser Val Ala Val His Ser Val Gln Gln Ala
                 85                  90                  95

Ala Gly Gly Gly Gly His Leu Glu Asp Pro Glu Leu Ala Leu Leu Thr
```

```
            100                 105                 110

Lys Lys Thr Leu Glu Ser Ser Leu Asn Asn Thr Thr Ser Leu Ser Phe
        115                 120                 125

Phe Arg Ser Thr Ser Ser Arg Ile Lys Asn Ala Ser Arg Glu Leu Arg
    130                 135                 140

Arg Val Phe Ser Arg Arg Pro Ser Pro Ala Val Arg Arg Phe Asp Arg
145                 150                 155                 160

Thr Ser Ser Ala Ala Ile His Ala Leu Lys Gly Leu Lys Phe Ile Ala
                165                 170                 175

Thr Lys Thr Ala Ala Trp Pro Ala Val Asp Gln Arg Phe Asp Lys Leu
            180                 185                 190

Ser Ala Asp Ser Asn Gly Leu Leu Leu Ser Ala Lys Phe Trp Glu Cys
        195                 200                 205

Leu Gly Met Asn Lys Glu Ser Lys Asp Phe Ala Asp Gln Leu Phe Arg
    210                 215                 220

Ala Leu Ala Arg Arg Asn Asn Val Ser Gly Asp Ala Ile Thr Lys Glu
225                 230                 235                 240

Gln Leu Arg Ile Phe Trp Glu Gln Ile Ser Asp Glu Ser Phe Asp Ala
                245                 250                 255

Lys Leu Gln Val Phe Phe Asp Met Val Asp Lys Asp Glu Asp Gly Arg
            260                 265                 270

Val Thr Glu Glu Glu Val Ala Glu Ile Ile Ser Leu Ser Ala Ser Ala
        275                 280                 285

Asn Lys Leu Ser Asn Ile Gln Lys Gln Ala Lys Glu Tyr Ala Ala Leu
    290                 295                 300

Ile Met Glu Glu Leu Asp Pro Asp Asn Ala Gly Phe Ile Met Ile Glu
305                 310                 315                 320

Asn Leu Glu Met Leu Leu Leu Gln Ala Pro Asn Gln Ser Val Arg Met
                325                 330                 335

Gly Asp Ser Arg Ile Leu Ser Gln Met Leu Ser Gln Lys Leu Arg Pro
            340                 345                 350

Ala Lys Glu Ser Asn Pro Leu Leu Arg Trp Ser Glu Lys Ile Lys Tyr
        355                 360                 365

Phe Ile Leu Asp Asn Trp Gln Arg Leu Trp Ile Met Met Leu Trp Leu
    370                 375                 380

Gly Ile Cys Gly Gly Leu Phe Thr Tyr Lys Phe Ile Gln Tyr Lys Asn
385                 390                 395                 400

Lys Ala Ala Tyr Gly Val Met Gly Tyr Cys Val Cys Val Ala Lys Gly
                405                 410                 415

Gly Ala Glu Thr Leu Lys Phe Asn Met Ala Leu Ile Leu Leu Pro Val
            420                 425                 430

Cys Arg Asn Thr Ile Thr Trp Leu Arg Asn Lys Thr Lys Leu Gly Thr
        435                 440                 445

Val Val Pro Phe Asp Asp Ser Leu Asn Phe His Lys Val Ile Ala Ser
    450                 455                 460

Gly Ile Val Val Gly Val Leu Leu His Ala Gly Ala His Leu Thr Cys
465                 470                 475                 480

Asp Phe Pro Arg Leu Ile Ala Ala Asp Glu Asp Thr Tyr Glu Pro Met
                485                 490                 495

Glu Lys Tyr Phe Gly Asp Gln Pro Thr Ser Tyr Trp Trp Phe Val Lys
            500                 505                 510

Gly Val Glu Gly Trp Thr Gly Ile Val Met Val Val Leu Met Ala Ile
        515                 520                 525
```

```
Ala Phe Thr Leu Ala Thr Pro Trp Phe Arg Arg Asn Lys Leu Asn Leu
    530                 535                 540

Pro Asn Phe Leu Lys Lys Leu Thr Gly Phe Asn Ala Phe Trp Tyr Thr
545                 550                 555                 560

His His Leu Phe Ile Ile Val Tyr Ala Leu Leu Ile Val His Gly Ile
                565                 570                 575

Lys Leu Tyr Leu Thr Lys Ile Trp Tyr Gln Lys Thr Thr Trp Met Tyr
            580                 585                 590

Leu Ala Val Pro Ile Leu Leu Tyr Ala Ser Glu Arg Leu Leu Arg Ala
        595                 600                 605

Phe Arg Ser Ser Ile Lys Pro Val Lys Met Ile Lys Val Ala Val Tyr
    610                 615                 620

Pro Gly Asn Val Leu Ser Leu His Met Thr Lys Pro Gln Gly Phe Lys
625                 630                 635                 640

Tyr Lys Ser Gly Gln Phe Met Leu Val Asn Cys Arg Ala Val Ser Pro
                645                 650                 655

Phe Glu Trp His Pro Phe Ser Ile Thr Ser Ala Pro Gly Asp Asp Tyr
            660                 665                 670

Leu Ser Val His Ile Arg Thr Leu Gly Asp Trp Thr Arg Lys Leu Arg
        675                 680                 685

Thr Val Phe Ser Glu Val Cys Lys Pro Pro Thr Ala Gly Lys Ser Gly
    690                 695                 700

Leu Leu Arg Ala Asp Gly Gly Asp Gly Asn Leu Pro Phe Pro Lys Val
705                 710                 715                 720

Leu Ile Asp Gly Pro Tyr Gly Ala Pro Ala Gln Asp Tyr Lys Lys Tyr
                725                 730                 735

Asp Val Val Leu Leu Val Gly Leu Gly Ile Gly Ala Thr Pro Met Ile
            740                 745                 750

Ser Ile Leu Lys Asp Ile Ile Asn Asn Met Lys Gly Pro Asp Arg Asp
        755                 760                 765

Ser Asp Ile Glu Asn Asn Asn Ser Asn Asn Asn Ser Lys Gly Phe Lys
    770                 775                 780

Thr Arg Lys Ala Tyr Phe Tyr Trp Val Thr Arg Glu Gln Gly Ser Phe
785                 790                 795                 800

Glu Trp Phe Lys Gly Ile Met Asp Glu Ile Ser Glu Leu Asp Glu Glu
                805                 810                 815

Gly Ile Ile Glu Leu His Asn Tyr Cys Thr Ser Val Tyr Glu Glu Gly
            820                 825                 830

Asp Ala Arg Val Ala Leu Ile Ala Met Leu Gln Ser Leu Gln His Ala
        835                 840                 845

Lys Asn Gly Val Asp Val Val Ser Gly Thr Arg Val Lys Ser His Phe
    850                 855                 860

Ala Lys Pro Asn Trp Arg Gln Val Tyr Lys Lys Ile Ala Val Gln His
865                 870                 875                 880

Pro Gly Lys Arg Ile Gly Val Phe Tyr Cys Gly Met Pro Gly Met Ile
                885                 890                 895

Lys Glu Leu Lys Asn Leu Ala Leu Asp Phe Ser Arg Lys Thr Thr Thr
            900                 905                 910

Lys Phe Asp Phe His Lys Glu Asn Phe
        915                 920
```

<210> SEQ ID NO 15
<211> LENGTH: 3338
<212> TYPE: DNA
<213> ORGANISM: Nicotiana tabacum

```
<220> FEATURE:
<221> NAME/KEY: CDS
<222> LOCATION: (313)..(3129)
<223> OTHER INFORMATION: coding for NADPH oxidase
<220> FEATURE:
<221> NAME/KEY: misc_feature
<222> LOCATION: (1952)..(1952)
<223> OTHER INFORMATION: n is a, c, g, or t

<400> SEQUENCE: 15

ggcacgagaa aatccccaat cttttatttg tttattaaaa ttagtacgcc aagaaagaaa     60

gaaagaaaga cagaaagact cggtcttctt tcttctcttg gtctgaaact ccaaaataga    120

ataccaatta ttaatctttt gtcatctttt tccttctcgc gttcatatat actggaatat    180

acatcttttt ttcaacctat cttctttcat tttcaagaat tcgggttcca taaatagtag    240

gttcactact tttatttcaa cctccttaaa gtttattcat tcatattttt tctcaaagaa    300

aaaactatag aa atg caa aat tcg gaa aat cat cat ccg cac cac cag cac    351
              Met Gln Asn Ser Glu Asn His His Pro His His Gln His
                1               5                   10

cac cat tcg gac aca gag ata att gga aat gat aga gcg tcg tac agt      399
His His Ser Asp Thr Glu Ile Ile Gly Asn Asp Arg Ala Ser Tyr Ser
     15                  20                  25

ggt ccg tta agc gga ccg tta aac aaa cga ggc ggc aaa aag agt gcg      447
Gly Pro Leu Ser Gly Pro Leu Asn Lys Arg Gly Gly Lys Lys Ser Ala
 30                  35                  40                  45

aga ttt aac att cct gaa tct acc gac atc gga acc agt gtc gga acc      495
Arg Phe Asn Ile Pro Glu Ser Thr Asp Ile Gly Thr Ser Val Gly Thr
                 50                  55                  60

ggc ggc aag tcc aat gat gat gcg tac gtt gaa atc act ctc gat gtc      543
Gly Gly Lys Ser Asn Asp Asp Ala Tyr Val Glu Ile Thr Leu Asp Val
             65                  70                  75

cgc gaa gat tcc gtc gct gtc cac agt gtc aaa act gcc ggc ggt gat      591
Arg Glu Asp Ser Val Ala Val His Ser Val Lys Thr Ala Gly Gly Asp
         80                  85                  90

gac gtg gaa gat ccc gag ctg gct tta ttg gct aaa ggc tta gag aag      639
Asp Val Glu Asp Pro Glu Leu Ala Leu Leu Ala Lys Gly Leu Glu Lys
     95                 100                 105

aag tcc act tta gga tct tca ctt gtt cga aat gct tcg tct aga att      687
Lys Ser Thr Leu Gly Ser Ser Leu Val Arg Asn Ala Ser Ser Arg Ile
110                 115                 120                 125

cgg caa gtg tca caa gag ctc agg cgt ttg gct tcc tta aat aaa cgc      735
Arg Gln Val Ser Gln Glu Leu Arg Arg Leu Ala Ser Leu Asn Lys Arg
                130                 135                 140

cca att cct act gga agg ttc gac agg aat aaa tca gct gct gct cat      783
Pro Ile Pro Thr Gly Arg Phe Asp Arg Asn Lys Ser Ala Ala Ala His
            145                 150                 155

gct ctt aaa ggt ctc aag ttt att agt aag acc gac ggc ggc gct ggt      831
Ala Leu Lys Gly Leu Lys Phe Ile Ser Lys Thr Asp Gly Gly Ala Gly
        160                 165                 170

tgg gcc gcc gtc gag aag cgg ttc gat gag att act gct tct act act      879
Trp Ala Ala Val Glu Lys Arg Phe Asp Glu Ile Thr Ala Ser Thr Thr
    175                 180                 185

ggt ttg ctt cct cgt gcc aaa ttt gga gaa tgt ata ggt atg aat aag      927
Gly Leu Leu Pro Arg Ala Lys Phe Gly Glu Cys Ile Gly Met Asn Lys
190                 195                 200                 205

gag tct aag gaa ttt gct gtt gag cta tat gat gcg cta gct cgg agg      975
Glu Ser Lys Glu Phe Ala Val Glu Leu Tyr Asp Ala Leu Ala Arg Arg
                210                 215                 220

aga aac att aca act gat tcc att aac aaa gca cag ctc aaa gag ttc     1023
Arg Asn Ile Thr Thr Asp Ser Ile Asn Lys Ala Gln Leu Lys Glu Phe
            225                 230                 235
```

```
tgg gac caa gtg gct gac caa agt ttt gat tct cgc ctt caa aca ttt      1071
Trp Asp Gln Val Ala Asp Gln Ser Phe Asp Ser Arg Leu Gln Thr Phe
        240                 245                 250

ttt gac atg gtt gat aaa gat gct gat ggt aga att aca gaa gaa gaa      1119
Phe Asp Met Val Asp Lys Asp Ala Asp Gly Arg Ile Thr Glu Glu Glu
    255                 260                 265

gtc aga gag att ata ggc ctt agc gcg tcg gcc aac agg ctg tca aca      1167
Val Arg Glu Ile Ile Gly Leu Ser Ala Ser Ala Asn Arg Leu Ser Thr
270                 275                 280                 285

atc cag aaa caa gct gat gaa tac gca gca atg atc atg gaa gag ttg      1215
Ile Gln Lys Gln Ala Asp Glu Tyr Ala Ala Met Ile Met Glu Glu Leu
                290                 295                 300

gat cct aac aac ctc gga tac att atg att gag aac ttg gaa atg ctt      1263
Asp Pro Asn Asn Leu Gly Tyr Ile Met Ile Glu Asn Leu Glu Met Leu
            305                 310                 315

tta ctg caa gca cca aat caa tca gtg caa aga gga ggc gaa agt cgg      1311
Leu Leu Gln Ala Pro Asn Gln Ser Val Gln Arg Gly Gly Glu Ser Arg
        320                 325                 330

aac ttg agt caa atg cta agt caa aaa cta aag cat aca caa gag aga      1359
Asn Leu Ser Gln Met Leu Ser Gln Lys Leu Lys His Thr Gln Glu Arg
    335                 340                 345

aat cca ata gta aga tgg tac aag agt ttc atg tac ttt ttg ctg gat      1407
Asn Pro Ile Val Arg Trp Tyr Lys Ser Phe Met Tyr Phe Leu Leu Asp
350                 355                 360                 365

aat tgg caa aga gtt tgg gta ttg tta ctg tgg att gga att atg gct      1455
Asn Trp Gln Arg Val Trp Val Leu Leu Leu Trp Ile Gly Ile Met Ala
                370                 375                 380

ggt cta ttt aca tgg aaa tat ata cag tat aaa gaa aaa gct gca tat      1503
Gly Leu Phe Thr Trp Lys Tyr Ile Gln Tyr Lys Glu Lys Ala Ala Tyr
            385                 390                 395

aaa gtc atg ggt ccc tgt gtg tgt ttt gcc aaa ggt gct gct gaa aca      1551
Lys Val Met Gly Pro Cys Val Cys Phe Ala Lys Gly Ala Ala Glu Thr
        400                 405                 410

ctc aag ctc aac atg gca att att tta ttt ccg gtt tgc aga aac acg      1599
Leu Lys Leu Asn Met Ala Ile Ile Leu Phe Pro Val Cys Arg Asn Thr
    415                 420                 425

atc aca tgg ctt cga aat aag acc aga tta ggt gct gct gtt cct ttt      1647
Ile Thr Trp Leu Arg Asn Lys Thr Arg Leu Gly Ala Ala Val Pro Phe
430                 435                 440                 445

gat gat aac ctt aat ttt cac aaa gtg ata gca gtg gca att gct ctt      1695
Asp Asp Asn Leu Asn Phe His Lys Val Ile Ala Val Ala Ile Ala Leu
                450                 455                 460

ggg gtt gga ata cac gga cta tct cac ttg aca tgt gat ttt cct cgg      1743
Gly Val Gly Ile His Gly Leu Ser His Leu Thr Cys Asp Phe Pro Arg
            465                 470                 475

ctt tta aat gct agt gaa gaa gaa tat gaa cca atg aag tac tat ttt      1791
Leu Leu Asn Ala Ser Glu Glu Glu Tyr Glu Pro Met Lys Tyr Tyr Phe
        480                 485                 490

gga gat cag cca gaa agc tat tgg tgg ttt ata aaa gga gta gaa ggg      1839
Gly Asp Gln Pro Glu Ser Tyr Trp Trp Phe Ile Lys Gly Val Glu Gly
    495                 500                 505

gta act gga att ata atg gtg gtt tta atg gca ata gca ttt act cta      1887
Val Thr Gly Ile Ile Met Val Val Leu Met Ala Ile Ala Phe Thr Leu
510                 515                 520                 525

gca acc cca tgg ttt aga agg aat aga gtt agt ttg cca aaa cca ttt      1935
Ala Thr Pro Trp Phe Arg Arg Asn Arg Val Ser Leu Pro Lys Pro Phe
                530                 535                 540

cac aaa ctc act gga tnt aat gcc ttt tgg tac tct cac cat ctc ttt      1983
His Lys Leu Thr Gly Xaa Asn Ala Phe Trp Tyr Ser His His Leu Phe
            545                 550                 555
```

```
gtt atc gtc tac act ctg ttc att gtg cat ggt gaa aag cta tac att     2031
Val Ile Val Tyr Thr Leu Phe Ile Val His Gly Glu Lys Leu Tyr Ile
        560                 565                 570

acc aaa gat tgg tac aag aga acc gac atg gat gta ctt tta act atc     2079
Thr Lys Asp Trp Tyr Lys Arg Thr Asp Met Asp Val Leu Leu Thr Ile
    575                 580                 585

cca atc ata ctc tat gct agt gaa agg ttg att agg gca ttc agg tca     2127
Pro Ile Ile Leu Tyr Ala Ser Glu Arg Leu Ile Arg Ala Phe Arg Ser
590                 595                 600                 605

agc att aaa gct gtt aag att ttg aag gtg gca gta tat cca gga aat     2175
Ser Ile Lys Ala Val Lys Ile Leu Lys Val Ala Val Tyr Pro Gly Asn
            610                 615                 620

gtg ttg gca ctt cac atg tca aaa cca cag ggc tac aaa tac aaa agt     2223
Val Leu Ala Leu His Met Ser Lys Pro Gln Gly Tyr Lys Tyr Lys Ser
            625                 630                 635

ggg caa tac atg ttt gtc aac tgt gct gca gtt tct cca ttt gag tgg     2271
Gly Gln Tyr Met Phe Val Asn Cys Ala Ala Val Ser Pro Phe Glu Trp
        640                 645                 650

cat cca ttt tca att act tcg gcc cca gga gat gac tat ctc agt gtc     2319
His Pro Phe Ser Ile Thr Ser Ala Pro Gly Asp Asp Tyr Leu Ser Val
    655                 660                 665

cat att cga act ctt ggt gat tgg acc agg caa ctt aaa act gtt ttc     2367
His Ile Arg Thr Leu Gly Asp Trp Thr Arg Gln Leu Lys Thr Val Phe
670                 675                 680                 685

tcc gag gtt tgc cag cca cca cct aat gga aaa agt gga ctc ctc aga     2415
Ser Glu Val Cys Gln Pro Pro Pro Asn Gly Lys Ser Gly Leu Leu Arg
            690                 695                 700

gct gac tac ttg caa gga gag aat aat cct aat ttc cca agg gtg tta     2463
Ala Asp Tyr Leu Gln Gly Glu Asn Asn Pro Asn Phe Pro Arg Val Leu
            705                 710                 715

ata gat gga cca tat gga gca cca gca caa gac tac aag aaa tat gag     2511
Ile Asp Gly Pro Tyr Gly Ala Pro Ala Gln Asp Tyr Lys Lys Tyr Glu
        720                 725                 730

gtg gtt ttg ttg gta ggt ctt gga att gga gct aca cca atg atc agt     2559
Val Val Leu Leu Val Gly Leu Gly Ile Gly Ala Thr Pro Met Ile Ser
    735                 740                 745

att gtt aaa gac att gtc aac aac atg aag gca atg gac gaa gaa gaa     2607
Ile Val Lys Asp Ile Val Asn Asn Met Lys Ala Met Asp Glu Glu Glu
750                 755                 760                 765

aat tcc ttg gaa gat gga cac aat aat aat atg gca cca aat tct agc     2655
Asn Ser Leu Glu Asp Gly His Asn Asn Asn Met Ala Pro Asn Ser Ser
            770                 775                 780

ccc aat att gca aaa aat aag ggt aat aaa tca ggt tca gca agt gga     2703
Pro Asn Ile Ala Lys Asn Lys Gly Asn Lys Ser Gly Ser Ala Ser Gly
            785                 790                 795

gga aat aat ttc aat aca agg aga gca tat ttc tat tgg gtt act aga     2751
Gly Asn Asn Phe Asn Thr Arg Arg Ala Tyr Phe Tyr Trp Val Thr Arg
        800                 805                 810

gaa caa ggt tca ttt gat tgg ttc aaa ggt ata atg aat gaa gct gct     2799
Glu Gln Gly Ser Phe Asp Trp Phe Lys Gly Ile Met Asn Glu Ala Ala
    815                 820                 825

gaa atg gac cat aag gga gta att gaa atg cat aat tat tgt act agt     2847
Glu Met Asp His Lys Gly Val Ile Glu Met His Asn Tyr Cys Thr Ser
830                 835                 840                 845

gtt tat gaa gaa ggt gat gct cgt tct gct ctt att act atg ctt cag     2895
Val Tyr Glu Glu Gly Asp Ala Arg Ser Ala Leu Ile Thr Met Leu Gln
            850                 855                 860

tct ctt cac cat gcc aaa aat ggt gtt gac att gtc tct ggc acc aga     2943
Ser Leu His His Ala Lys Asn Gly Val Asp Ile Val Ser Gly Thr Arg
            865                 870                 875
```

```
gtt aag tca cat ttt gct aaa cct aat tgg cgt aat gtc tac aaa cgc     2991
Val Lys Ser His Phe Ala Lys Pro Asn Trp Arg Asn Val Tyr Lys Arg
      880                 885                 890

att gct ctc aac cac cct gag gct aaa gtt ggg gtc ttc tat tgt ggg     3039
Ile Ala Leu Asn His Pro Glu Ala Lys Val Gly Val Phe Tyr Cys Gly
    895                 900                 905

gca cca gca ctg acc aaa gaa cta aga caa cac gcc ttg gat ttt tca     3087
Ala Pro Ala Leu Thr Lys Glu Leu Arg Gln His Ala Leu Asp Phe Ser
910                 915                 920                 925

cac aag aca tct acc aag ttt gat ttc cat aaa gaa aat ttt             3129
His Lys Thr Ser Thr Lys Phe Asp Phe His Lys Glu Asn Phe
                930                 935

tgagcaaaga atagaccatt aagcagagca ttaaaatttc atcaaaacag ctaaggacac   3189

aggttgtttt atagaagtct accaactctc cctattgtgt acagataatg ttgcacttca   3249

agttgatata tagttgtggt tgtgatgcta gtatattaca aaataataag attattttta   3309

tttgtagtaa aaaaaaaaaa aaaaaaaaa                                     3338
```

<210> SEQ ID NO 16
<211> LENGTH: 939
<212> TYPE: PRT
<213> ORGANISM: Nicotiana tabacum
<220> FEATURE:
<221> NAME/KEY: misc_feature
<222> LOCATION: (547)..(547)
<223> OTHER INFORMATION: The ‘Xaa’ at location 547 stands for Tyr, Cys, Ser, or Phe

<400> SEQUENCE: 16

```
Met Gln Asn Ser Glu Asn His His Pro His His Gln His His His Ser
  1               5                  10                  15

Asp Thr Glu Ile Ile Gly Asn Asp Arg Ala Ser Tyr Ser Gly Pro Leu
            20                  25                  30

Ser Gly Pro Leu Asn Lys Arg Gly Gly Lys Lys Ser Ala Arg Phe Asn
        35                  40                  45

Ile Pro Glu Ser Thr Asp Ile Gly Thr Ser Val Gly Thr Gly Gly Lys
     50                  55                  60

Ser Asn Asp Asp Ala Tyr Val Glu Ile Thr Leu Asp Val Arg Glu Asp
 65                  70                  75                  80

Ser Val Ala Val His Ser Val Lys Thr Ala Gly Gly Asp Asp Val Glu
                 85                  90                  95

Asp Pro Glu Leu Ala Leu Leu Ala Lys Gly Leu Glu Lys Lys Ser Thr
            100                 105                 110

Leu Gly Ser Ser Leu Val Arg Asn Ala Ser Ser Arg Ile Arg Gln Val
        115                 120                 125

Ser Gln Glu Leu Arg Arg Leu Ala Ser Leu Asn Lys Arg Pro Ile Pro
    130                 135                 140

Thr Gly Arg Phe Asp Arg Asn Lys Ser Ala Ala Ala His Ala Leu Lys
145                 150                 155                 160

Gly Leu Lys Phe Ile Ser Lys Thr Asp Gly Gly Ala Gly Trp Ala Ala
                165                 170                 175

Val Glu Lys Arg Phe Asp Glu Ile Thr Ala Ser Thr Thr Gly Leu Leu
            180                 185                 190

Pro Arg Ala Lys Phe Gly Glu Cys Ile Gly Met Asn Lys Glu Ser Lys
        195                 200                 205

Glu Phe Ala Val Glu Leu Tyr Asp Ala Leu Ala Arg Arg Arg Asn Ile
    210                 215                 220
```

```
Thr Thr Asp Ser Ile Asn Lys Ala Gln Leu Lys Glu Phe Trp Asp Gln
225                 230                 235                 240

Val Ala Asp Gln Ser Phe Asp Ser Arg Leu Gln Thr Phe Phe Asp Met
                245                 250                 255

Val Asp Lys Asp Ala Asp Gly Arg Ile Thr Glu Glu Glu Val Arg Glu
            260                 265                 270

Ile Ile Gly Leu Ser Ala Ser Ala Asn Arg Leu Ser Thr Ile Gln Lys
        275                 280                 285

Gln Ala Asp Glu Tyr Ala Ala Met Ile Met Glu Glu Leu Asp Pro Asn
    290                 295                 300

Asn Leu Gly Tyr Ile Met Ile Glu Asn Leu Glu Met Leu Leu Leu Gln
305                 310                 315                 320

Ala Pro Asn Gln Ser Val Gln Arg Gly Gly Glu Ser Arg Asn Leu Ser
                325                 330                 335

Gln Met Leu Ser Gln Lys Leu Lys His Thr Gln Glu Arg Asn Pro Ile
            340                 345                 350

Val Arg Trp Tyr Lys Ser Phe Met Tyr Phe Leu Leu Asp Asn Trp Gln
        355                 360                 365

Arg Val Trp Val Leu Leu Leu Trp Ile Gly Ile Met Ala Gly Leu Phe
    370                 375                 380

Thr Trp Lys Tyr Ile Gln Tyr Lys Glu Lys Ala Ala Tyr Lys Val Met
385                 390                 395                 400

Gly Pro Cys Val Cys Phe Ala Lys Gly Ala Ala Glu Thr Leu Lys Leu
                405                 410                 415

Asn Met Ala Ile Ile Leu Phe Pro Val Cys Arg Asn Thr Ile Thr Trp
            420                 425                 430

Leu Arg Asn Lys Thr Arg Leu Gly Ala Ala Val Pro Phe Asp Asp Asn
        435                 440                 445

Leu Asn Phe His Lys Val Ile Ala Val Ala Ile Ala Leu Gly Val Gly
    450                 455                 460

Ile His Gly Leu Ser His Leu Thr Cys Asp Phe Pro Arg Leu Leu Asn
465                 470                 475                 480

Ala Ser Glu Glu Glu Tyr Glu Pro Met Lys Tyr Tyr Phe Gly Asp Gln
                485                 490                 495

Pro Glu Ser Tyr Trp Trp Phe Ile Lys Gly Val Glu Gly Val Thr Gly
            500                 505                 510

Ile Ile Met Val Val Leu Met Ala Ile Ala Phe Thr Leu Ala Thr Pro
        515                 520                 525

Trp Phe Arg Arg Asn Arg Val Ser Leu Pro Lys Pro Phe His Lys Leu
    530                 535                 540

Thr Gly Xaa Asn Ala Phe Trp Tyr Ser His His Leu Phe Val Ile Val
545                 550                 555                 560

Tyr Thr Leu Phe Ile Val His Gly Glu Lys Leu Tyr Ile Thr Lys Asp
                565                 570                 575

Trp Tyr Lys Arg Thr Asp Met Asp Val Leu Leu Thr Ile Pro Ile Ile
            580                 585                 590

Leu Tyr Ala Ser Glu Arg Leu Ile Arg Ala Phe Arg Ser Ser Ile Lys
        595                 600                 605

Ala Val Lys Ile Leu Lys Val Ala Val Tyr Pro Gly Asn Val Leu Ala
    610                 615                 620

Leu His Met Ser Lys Pro Gln Gly Tyr Lys Tyr Lys Ser Gly Gln Tyr
625                 630                 635                 640

Met Phe Val Asn Cys Ala Ala Val Ser Pro Phe Glu Trp His Pro Phe
                645                 650                 655
```

```
Ser Ile Thr Ser Ala Pro Gly Asp Asp Tyr Leu Ser Val His Ile Arg
            660                 665                 670

Thr Leu Gly Asp Trp Thr Arg Gln Leu Lys Thr Val Phe Ser Glu Val
        675                 680                 685

Cys Gln Pro Pro Pro Asn Gly Lys Ser Gly Leu Leu Arg Ala Asp Tyr
    690                 695                 700

Leu Gln Gly Glu Asn Asn Pro Asn Phe Pro Arg Val Leu Ile Asp Gly
705                 710                 715                 720

Pro Tyr Gly Ala Pro Ala Gln Asp Tyr Lys Lys Tyr Glu Val Val Leu
                725                 730                 735

Leu Val Gly Leu Gly Ile Gly Ala Thr Pro Met Ile Ser Ile Val Lys
            740                 745                 750

Asp Ile Val Asn Asn Met Lys Ala Met Asp Glu Glu Glu Asn Ser Leu
        755                 760                 765

Glu Asp Gly His Asn Asn Asn Met Ala Pro Asn Ser Ser Pro Asn Ile
    770                 775                 780

Ala Lys Asn Lys Gly Asn Lys Ser Gly Ser Ala Ser Gly Gly Asn Asn
785                 790                 795                 800

Phe Asn Thr Arg Arg Ala Tyr Phe Tyr Trp Val Thr Arg Glu Gln Gly
                805                 810                 815

Ser Phe Asp Trp Phe Lys Gly Ile Met Asn Glu Ala Ala Glu Met Asp
            820                 825                 830

His Lys Gly Val Ile Glu Met His Asn Tyr Cys Thr Ser Val Tyr Glu
        835                 840                 845

Glu Gly Asp Ala Arg Ser Ala Leu Ile Thr Met Leu Gln Ser Leu His
    850                 855                 860

His Ala Lys Asn Gly Val Asp Ile Val Ser Gly Thr Arg Val Lys Ser
865                 870                 875                 880

His Phe Ala Lys Pro Asn Trp Arg Asn Val Tyr Lys Arg Ile Ala Leu
                885                 890                 895

Asn His Pro Glu Ala Lys Val Gly Val Phe Tyr Cys Gly Ala Pro Ala
            900                 905                 910

Leu Thr Lys Glu Leu Arg Gln His Ala Leu Asp Phe Ser His Lys Thr
        915                 920                 925

Ser Thr Lys Phe Asp Phe His Lys Glu Asn Phe
    930                 935


<210> SEQ ID NO 17
<211> LENGTH: 2532
<212> TYPE: DNA
<213> ORGANISM: Oryza sativa
<220> FEATURE:
<221> NAME/KEY: CDS
<222> LOCATION: (1)..(2529)
<223> OTHER INFORMATION: coding for NADPH oxidase

<400> SEQUENCE: 17

atg gcg tcg ccg tac gac cac cag tcg ccg cat gcg cag cac ccg tcg       48
Met Ala Ser Pro Tyr Asp His Gln Ser Pro His Ala Gln His Pro Ser
  1               5                  10                  15

ggg ttg ccg agg ccg ccg ggg gcg ggg gcg ggt gcg gcg gcg ggc ggg       96
Gly Leu Pro Arg Pro Pro Gly Ala Gly Ala Gly Ala Ala Ala Gly Gly
             20                  25                  30

ttc gcg cgg ggg ctg atg aag cag ccg tcg cgg ctg gcg tcc ggg gtg      144
Phe Ala Arg Gly Leu Met Lys Gln Pro Ser Arg Leu Ala Ser Gly Val
         35                  40                  45

agg cag ttc gcg tcg agg gtg tcg atg aag gtg ccg gag ggg gtg ggg      192
```

```
Arg Gln Phe Ala Ser Arg Val Ser Met Lys Val Pro Glu Gly Val Gly
     50                  55                  60

ggg atg cgg ccc ggt ggc ggg agg atg acg cgg atg cag tcc agc gcg      240
Gly Met Arg Pro Gly Gly Gly Arg Met Thr Arg Met Gln Ser Ser Ala
 65                  70                  75                  80

cag gtg ggg ctc cgg ggg ctc cgc ttc ctc gac aag acg tcc ggc ggg      288
Gln Val Gly Leu Arg Gly Leu Arg Phe Leu Asp Lys Thr Ser Gly Gly
                 85                  90                  95

aag gag ggg tgg aag tcc gtc gag cgc cgc ttc gac gag atg aac cgc      336
Lys Glu Gly Trp Lys Ser Val Glu Arg Arg Phe Asp Glu Met Asn Arg
            100                 105                 110

aac ggc cgc ctc ccc aag gag agc ttc ggc aag tgc atc ggc atg ggg      384
Asn Gly Arg Leu Pro Lys Glu Ser Phe Gly Lys Cys Ile Gly Met Gly
        115                 120                 125

gac tcc aag gag ttc gcc ggc gag ctg ttc gtg gcg ctg gcg cgg cgg      432
Asp Ser Lys Glu Phe Ala Gly Glu Leu Phe Val Ala Leu Ala Arg Arg
    130                 135                 140

agg aac ctg gag ccg gag gac ggc atc acc aag gag cag ctc aag gag      480
Arg Asn Leu Glu Pro Glu Asp Gly Ile Thr Lys Glu Gln Leu Lys Glu
145                 150                 155                 160

ttc tgg gag gag atg acc gac cag aac ttc gac tcg cgg ctt cgc att      528
Phe Trp Glu Glu Met Thr Asp Gln Asn Phe Asp Ser Arg Leu Arg Ile
                165                 170                 175

ttc ttt gac atg tgc gac aag aat ggc gat ggg atg ctc acg gaa gat      576
Phe Phe Asp Met Cys Asp Lys Asn Gly Asp Gly Met Leu Thr Glu Asp
            180                 185                 190

gag gtc aag gag gtt att ata ctg agt gcg tcg gcg aac aag ctg gcg      624
Glu Val Lys Glu Val Ile Ile Leu Ser Ala Ser Ala Asn Lys Leu Ala
        195                 200                 205

aag ctg aag gga cac gcg gcg acg tac gcg tcg ctg atc atg gag gag      672
Lys Leu Lys Gly His Ala Ala Thr Tyr Ala Ser Leu Ile Met Glu Glu
    210                 215                 220

ctg gac ccg gac gac cgc ggg tac atc gag atc tgg cag ctg gag acg      720
Leu Asp Pro Asp Asp Arg Gly Tyr Ile Glu Ile Trp Gln Leu Glu Thr
225                 230                 235                 240

ctg ctg cgc ggc atg gtg agc gcg cag gcg gcg ccg gag aag atg aag      768
Leu Leu Arg Gly Met Val Ser Ala Gln Ala Ala Pro Glu Lys Met Lys
                245                 250                 255

cgg acg acg tcg agc ctc gcg agg acg atg atc ccg tcg cgg tac cgg      816
Arg Thr Thr Ser Ser Leu Ala Arg Thr Met Ile Pro Ser Arg Tyr Arg
            260                 265                 270

agc ccg ctg aag cgg cac gtg tcc agg acg gtg gac ttc gtg cac gag      864
Ser Pro Leu Lys Arg His Val Ser Arg Thr Val Asp Phe Val His Glu
        275                 280                 285

aac tgg aag cgg atc tgg ctc gtc gcg ctg tgg ctc gcc gtc aac gtc      912
Asn Trp Lys Arg Ile Trp Leu Val Ala Leu Trp Leu Ala Val Asn Val
    290                 295                 300

ggc ctc ttc gcc tac aag ttc gag cag tac gag cgg cgc gcc gcg ttc      960
Gly Leu Phe Ala Tyr Lys Phe Glu Gln Tyr Glu Arg Arg Ala Ala Phe
305                 310                 315                 320

cag gtg atg ggc cac tgc gtg tgc gtg gcc aag ggc gcc gcc gag gtg     1008
Gln Val Met Gly His Cys Val Cys Val Ala Lys Gly Ala Ala Glu Val
                325                 330                 335

ctc aag ctc aac atg gcg ctc atc ctc ctc ccc gtg tgc cgg aac acg     1056
Leu Lys Leu Asn Met Ala Leu Ile Leu Leu Pro Val Cys Arg Asn Thr
            340                 345                 350

ctc acc acg ctc agg tcc acg gcg ctc agc cac gtc atc ccc ttc gac     1104
Leu Thr Thr Leu Arg Ser Thr Ala Leu Ser His Val Ile Pro Phe Asp
        355                 360                 365

gac aac atc aac ttc cac aag gtg atc gcg gcg acc atc gcc gcc gcc     1152
```

```
Asp Asn Ile Asn Phe His Lys Val Ile Ala Ala Thr Ile Ala Ala Ala
    370                 375                 380

acc gcc gtc cac acg ctg gcg cac gtc acc tgc gac ttc ccg agg ctg     1200
Thr Ala Val His Thr Leu Ala His Val Thr Cys Asp Phe Pro Arg Leu
385                 390                 395                 400

atc aac tgc ccc agc gac aag ttc atg gcg acg ctg ggg ccg aac ttc     1248
Ile Asn Cys Pro Ser Asp Lys Phe Met Ala Thr Leu Gly Pro Asn Phe
                405                 410                 415

ggg tac agg cag ccg acg tac gcc gac ctg ctg gag agc gcc ccc ggc     1296
Gly Tyr Arg Gln Pro Thr Tyr Ala Asp Leu Leu Glu Ser Ala Pro Gly
            420                 425                 430

gtc acc ggc atc ctc atg atc atc atc atg tcc ttc tcc ttc acg ctg     1344
Val Thr Gly Ile Leu Met Ile Ile Ile Met Ser Phe Ser Phe Thr Leu
        435                 440                 445

gcc acg cac tcc ttc cgc cgg agc gtc gtc aag ctg ccg tcg ccg ctg     1392
Ala Thr His Ser Phe Arg Arg Ser Val Val Lys Leu Pro Ser Pro Leu
    450                 455                 460

cac cac ctc gcc ggc ttc aac gcc ttc tgg tac gcg cac cac ctc ctg     1440
His His Leu Ala Gly Phe Asn Ala Phe Trp Tyr Ala His His Leu Leu
465                 470                 475                 480

gtg ctc gcc tac gtc ctc ctc gtc gtg cac tcc tac ttc ata ttc ctc     1488
Val Leu Ala Tyr Val Leu Leu Val Val His Ser Tyr Phe Ile Phe Leu
                485                 490                 495

acc agg gag tgg tac aag aaa acg aca tgg atg tac ctg ata gtc cca     1536
Thr Arg Glu Trp Tyr Lys Lys Thr Thr Trp Met Tyr Leu Ile Val Pro
            500                 505                 510

gtg ctc ttc tat gca tgc gag aga acg atc aga aaa gtt cga gag aac     1584
Val Leu Phe Tyr Ala Cys Glu Arg Thr Ile Arg Lys Val Arg Glu Asn
        515                 520                 525

aac tac cgc gtg agc atc gtc aag gca gcg att tac cca gga aat gtg     1632
Asn Tyr Arg Val Ser Ile Val Lys Ala Ala Ile Tyr Pro Gly Asn Val
    530                 535                 540

ctc tct ctt cac atg aag aag ccg ccg ggt ttc aag tac aag agc ggg     1680
Leu Ser Leu His Met Lys Lys Pro Pro Gly Phe Lys Tyr Lys Ser Gly
545                 550                 555                 560

atg tac ctg ttt gtg aag tgc cct gat gtc tct cct ttc gaa tgg cat     1728
Met Tyr Leu Phe Val Lys Cys Pro Asp Val Ser Pro Phe Glu Trp His
                565                 570                 575

ccc ttc tcc atc act tct gca cct gga gat gac tac ctg agt gtg cat     1776
Pro Phe Ser Ile Thr Ser Ala Pro Gly Asp Asp Tyr Leu Ser Val His
            580                 585                 590

atc cgt aca cta ggt gac tgg acg act gaa ctc aga aac ctg ttt ggg     1824
Ile Arg Thr Leu Gly Asp Trp Thr Thr Glu Leu Arg Asn Leu Phe Gly
        595                 600                 605

aag gct tgc gag gca cag gtt act tct aag aag gct acc ctt tca aga     1872
Lys Ala Cys Glu Ala Gln Val Thr Ser Lys Lys Ala Thr Leu Ser Arg
    610                 615                 620

ctt gaa act aca gtt gtg gcg gac gct cag aca gag gat act agg ttt     1920
Leu Glu Thr Thr Val Val Ala Asp Ala Gln Thr Glu Asp Thr Arg Phe
625                 630                 635                 640

cct aag gtc ctt att gat ggg ccc tat ggt gca ccg gcg caa aac tac     1968
Pro Lys Val Leu Ile Asp Gly Pro Tyr Gly Ala Pro Ala Gln Asn Tyr
                645                 650                 655

aag aag tat gac att ctt ttg ctt att ggt ctt gga att ggt gct act     2016
Lys Lys Tyr Asp Ile Leu Leu Leu Ile Gly Leu Gly Ile Gly Ala Thr
            660                 665                 670

cct ttc atc agc att ctg aag gat ctg ttg aac aac att aaa tcc aac     2064
Pro Phe Ile Ser Ile Leu Lys Asp Leu Leu Asn Asn Ile Lys Ser Asn
        675                 680                 685

gaa gag gtg gaa agc ata cat ggt tct gag ata ggc agc ttc aag aac     2112
```

```
Glu Glu Val Glu Ser Ile His Gly Ser Glu Ile Gly Ser Phe Lys Asn
    690                 695                 700

aat ggg cca gga aga gct tac ttc tac tgg gtg acc aga gag caa ggg      2160
Asn Gly Pro Gly Arg Ala Tyr Phe Tyr Trp Val Thr Arg Glu Gln Gly
705                 710                 715                 720

tcc ttc gag tgg ttt aaa gga gtc atg aac gat gtc gct gaa agt gat      2208
Ser Phe Glu Trp Phe Lys Gly Val Met Asn Asp Val Ala Glu Ser Asp
                725                 730                 735

cac aat aat att ata gag atg cac aat tac ctg acc agc gtg tat gaa      2256
His Asn Asn Ile Ile Glu Met His Asn Tyr Leu Thr Ser Val Tyr Glu
            740                 745                 750

gaa ggc gac gca agg tca gct ttg att gcc atg gtt cag tca ctt caa      2304
Glu Gly Asp Ala Arg Ser Ala Leu Ile Ala Met Val Gln Ser Leu Gln
        755                 760                 765

cat gcc aaa aat ggt gtg gat atc gtc tcc ggc agc agg att cgc aca      2352
His Ala Lys Asn Gly Val Asp Ile Val Ser Gly Ser Arg Ile Arg Thr
    770                 775                 780

cat ttt gcg agg cct aac tgg aga aag gtg ttc tct gac ttg gcg aat      2400
His Phe Ala Arg Pro Asn Trp Arg Lys Val Phe Ser Asp Leu Ala Asn
785                 790                 795                 800

gcc cac aaa aac tca cgc ata ggt gtt ttc tat tgt gga tcc cct aca      2448
Ala His Lys Asn Ser Arg Ile Gly Val Phe Tyr Cys Gly Ser Pro Thr
                805                 810                 815

ctc acg aaa caa ctc aag gat ctt tca aaa gaa ttc agc cag aca acc      2496
Leu Thr Lys Gln Leu Lys Asp Leu Ser Lys Glu Phe Ser Gln Thr Thr
            820                 825                 830

aca act aga ttc cac ttc cac aag gaa aac ttt taa                      2532
Thr Thr Arg Phe His Phe His Lys Glu Asn Phe
        835                 840


<210> SEQ ID NO 18
<211> LENGTH: 843
<212> TYPE: PRT
<213> ORGANISM: Oryza sativa

<400> SEQUENCE: 18

Met Ala Ser Pro Tyr Asp His Gln Ser Pro His Ala Gln His Pro Ser
  1               5                  10                  15

Gly Leu Pro Arg Pro Pro Gly Ala Gly Ala Gly Ala Ala Ala Gly Gly
            20                  25                  30

Phe Ala Arg Gly Leu Met Lys Gln Pro Ser Arg Leu Ala Ser Gly Val
        35                  40                  45

Arg Gln Phe Ala Ser Arg Val Ser Met Lys Val Pro Glu Gly Val Gly
    50                  55                  60

Gly Met Arg Pro Gly Gly Gly Arg Met Thr Arg Met Gln Ser Ser Ala
 65                  70                  75                  80

Gln Val Gly Leu Arg Gly Leu Arg Phe Leu Asp Lys Thr Ser Gly Gly
                85                  90                  95

Lys Glu Gly Trp Lys Ser Val Glu Arg Arg Phe Asp Glu Met Asn Arg
            100                 105                 110

Asn Gly Arg Leu Pro Lys Glu Ser Phe Gly Lys Cys Ile Gly Met Gly
        115                 120                 125

Asp Ser Lys Glu Phe Ala Gly Glu Leu Phe Val Ala Leu Ala Arg Arg
    130                 135                 140

Arg Asn Leu Glu Pro Glu Asp Gly Ile Thr Lys Glu Gln Leu Lys Glu
145                 150                 155                 160

Phe Trp Glu Glu Met Thr Asp Gln Asn Phe Asp Ser Arg Leu Arg Ile
                165                 170                 175
```

```
Phe Phe Asp Met Cys Asp Lys Asn Gly Asp Gly Met Leu Thr Glu Asp
            180                 185                 190

Glu Val Lys Glu Val Ile Ile Leu Ser Ala Ser Ala Asn Lys Leu Ala
        195                 200                 205

Lys Leu Lys Gly His Ala Ala Thr Tyr Ala Ser Leu Ile Met Glu Glu
    210                 215                 220

Leu Asp Pro Asp Asp Arg Gly Tyr Ile Glu Ile Trp Gln Leu Glu Thr
225                 230                 235                 240

Leu Leu Arg Gly Met Val Ser Ala Gln Ala Ala Pro Glu Lys Met Lys
                245                 250                 255

Arg Thr Thr Ser Ser Leu Ala Arg Thr Met Ile Pro Ser Arg Tyr Arg
            260                 265                 270

Ser Pro Leu Lys Arg His Val Ser Arg Thr Val Asp Phe Val His Glu
        275                 280                 285

Asn Trp Lys Arg Ile Trp Leu Val Ala Leu Trp Leu Ala Val Asn Val
    290                 295                 300

Gly Leu Phe Ala Tyr Lys Phe Glu Gln Tyr Glu Arg Arg Ala Ala Phe
305                 310                 315                 320

Gln Val Met Gly His Cys Val Cys Val Ala Lys Gly Ala Ala Glu Val
                325                 330                 335

Leu Lys Leu Asn Met Ala Leu Ile Leu Leu Pro Val Cys Arg Asn Thr
            340                 345                 350

Leu Thr Thr Leu Arg Ser Thr Ala Leu Ser His Val Ile Pro Phe Asp
        355                 360                 365

Asp Asn Ile Asn Phe His Lys Val Ile Ala Ala Thr Ile Ala Ala Ala
    370                 375                 380

Thr Ala Val His Thr Leu Ala His Val Thr Cys Asp Phe Pro Arg Leu
385                 390                 395                 400

Ile Asn Cys Pro Ser Asp Lys Phe Met Ala Thr Leu Gly Pro Asn Phe
                405                 410                 415

Gly Tyr Arg Gln Pro Thr Tyr Ala Asp Leu Leu Glu Ser Ala Pro Gly
            420                 425                 430

Val Thr Gly Ile Leu Met Ile Ile Ile Met Ser Phe Ser Phe Thr Leu
        435                 440                 445

Ala Thr His Ser Phe Arg Arg Ser Val Val Lys Leu Pro Ser Pro Leu
    450                 455                 460

His His Leu Ala Gly Phe Asn Ala Phe Trp Tyr Ala His His Leu Leu
465                 470                 475                 480

Val Leu Ala Tyr Val Leu Leu Val Val His Ser Tyr Phe Ile Phe Leu
                485                 490                 495

Thr Arg Glu Trp Tyr Lys Lys Thr Thr Trp Met Tyr Leu Ile Val Pro
            500                 505                 510

Val Leu Phe Tyr Ala Cys Glu Arg Thr Ile Arg Lys Val Arg Glu Asn
        515                 520                 525

Asn Tyr Arg Val Ser Ile Val Lys Ala Ala Ile Tyr Pro Gly Asn Val
    530                 535                 540

Leu Ser Leu His Met Lys Lys Pro Pro Gly Phe Lys Tyr Lys Ser Gly
545                 550                 555                 560

Met Tyr Leu Phe Val Lys Cys Pro Asp Val Ser Pro Phe Glu Trp His
                565                 570                 575

Pro Phe Ser Ile Thr Ser Ala Pro Gly Asp Asp Tyr Leu Ser Val His
            580                 585                 590

Ile Arg Thr Leu Gly Asp Trp Thr Thr Glu Leu Arg Asn Leu Phe Gly
        595                 600                 605
```

```
Lys Ala Cys Glu Ala Gln Val Thr Ser Lys Lys Ala Thr Leu Ser Arg
    610                 615                 620

Leu Glu Thr Thr Val Val Ala Asp Ala Gln Thr Glu Asp Thr Arg Phe
625                 630                 635                 640

Pro Lys Val Leu Ile Asp Gly Pro Tyr Gly Ala Pro Ala Gln Asn Tyr
                645                 650                 655

Lys Lys Tyr Asp Ile Leu Leu Leu Ile Gly Leu Gly Ile Gly Ala Thr
            660                 665                 670

Pro Phe Ile Ser Ile Leu Lys Asp Leu Leu Asn Asn Ile Lys Ser Asn
        675                 680                 685

Glu Glu Val Glu Ser Ile His Gly Ser Glu Ile Gly Ser Phe Lys Asn
    690                 695                 700

Asn Gly Pro Gly Arg Ala Tyr Phe Tyr Trp Val Thr Arg Glu Gln Gly
705                 710                 715                 720

Ser Phe Glu Trp Phe Lys Gly Val Met Asn Asp Val Ala Glu Ser Asp
                725                 730                 735

His Asn Asn Ile Ile Glu Met His Asn Tyr Leu Thr Ser Val Tyr Glu
            740                 745                 750

Glu Gly Asp Ala Arg Ser Ala Leu Ile Ala Met Val Gln Ser Leu Gln
        755                 760                 765

His Ala Lys Asn Gly Val Asp Ile Val Ser Gly Ser Arg Ile Arg Thr
    770                 775                 780

His Phe Ala Arg Pro Asn Trp Arg Lys Val Phe Ser Asp Leu Ala Asn
785                 790                 795                 800

Ala His Lys Asn Ser Arg Ile Gly Val Phe Tyr Cys Gly Ser Pro Thr
                805                 810                 815

Leu Thr Lys Gln Leu Lys Asp Leu Ser Lys Glu Phe Ser Gln Thr Thr
            820                 825                 830

Thr Thr Arg Phe His Phe His Lys Glu Asn Phe
        835                 840


<210> SEQ ID NO 19
<211> LENGTH: 2604
<212> TYPE: DNA
<213> ORGANISM: Arabidopsis thaliana
<220> FEATURE:
<221> NAME/KEY: CDS
<222> LOCATION: (1)..(2601)
<223> OTHER INFORMATION: coding for NADPH oxidase

<400> SEQUENCE: 19

atg tct aga gtg agt ttt gaa gtg tca gga ggc tat cac tct gat gca       48
Met Ser Arg Val Ser Phe Glu Val Ser Gly Gly Tyr His Ser Asp Ala
  1               5                  10                  15

gaa gcc gga aac agc gga cca atg agc ggt ggt caa tta cca ccg atc       96
Glu Ala Gly Asn Ser Gly Pro Met Ser Gly Gly Gln Leu Pro Pro Ile
             20                  25                  30

tat aaa aaa ccg ggg aac tcc aga ttc act gct gag aac agt cag aga      144
Tyr Lys Lys Pro Gly Asn Ser Arg Phe Thr Ala Glu Asn Ser Gln Arg
         35                  40                  45

aca cgt acg gca cca tac gtg gac ctc acg gta gat gta caa gac gat      192
Thr Arg Thr Ala Pro Tyr Val Asp Leu Thr Val Asp Val Gln Asp Asp
     50                  55                  60

aca gtc tct gta cat agc ttg aaa atg gaa ggt gga tct agc gtt gaa      240
Thr Val Ser Val His Ser Leu Lys Met Glu Gly Gly Ser Ser Val Glu
 65                  70                  75                  80

gag agt ccg gag ctt act ttg ctg aaa cga aac cgt ctt gag aag aaa      288
Glu Ser Pro Glu Leu Thr Leu Leu Lys Arg Asn Arg Leu Glu Lys Lys
```

```
                85                  90                  95

aca acg gtg gtg aaa cgt ttg gcg tct gtt tct cac gag ctt aag cgt      336
Thr Thr Val Val Lys Arg Leu Ala Ser Val Ser His Glu Leu Lys Arg
            100                 105                 110

ttg aca tct gtt tct ggt ggt att ggt gga aga aag ccg cct cga ccg      384
Leu Thr Ser Val Ser Gly Gly Ile Gly Gly Arg Lys Pro Pro Arg Pro
        115                 120                 125

gct aag tta gac cgg act aaa tcc gcc gcg agt caa gcg ttg aag gga      432
Ala Lys Leu Asp Arg Thr Lys Ser Ala Ala Ser Gln Ala Leu Lys Gly
    130                 135                 140

ctt aag ttc att agt aaa acc gac ggt ggc gcc ggt tgg tct gcc gtg      480
Leu Lys Phe Ile Ser Lys Thr Asp Gly Gly Ala Gly Trp Ser Ala Val
145                 150                 155                 160

gag aag cgg ttt aat cag att acc gcg act acc ggt gga cta ctt ctt      528
Glu Lys Arg Phe Asn Gln Ile Thr Ala Thr Thr Gly Gly Leu Leu Leu
                165                 170                 175

cgg aca aag ttc ggt gaa tgc ata gga atg act tca aag gat ttt gct      576
Arg Thr Lys Phe Gly Glu Cys Ile Gly Met Thr Ser Lys Asp Phe Ala
            180                 185                 190

ttg gaa ctg ttt gat gca ttg gct aga aga agg aat ata aca ggg gaa      624
Leu Glu Leu Phe Asp Ala Leu Ala Arg Arg Arg Asn Ile Thr Gly Glu
        195                 200                 205

gtg att gat gga gat caa cta aag gag ttt tgg gaa caa att aat gat      672
Val Ile Asp Gly Asp Gln Leu Lys Glu Phe Trp Glu Gln Ile Asn Asp
    210                 215                 220

caa agt ttt gat tct cgg ctt aag aca ttc ttt gac atg gtg gat aaa      720
Gln Ser Phe Asp Ser Arg Leu Lys Thr Phe Phe Asp Met Val Asp Lys
225                 230                 235                 240

gat gct gat ggt aga ctt aca gaa gac gaa gtt aga gag ttg gag agt      768
Asp Ala Asp Gly Arg Leu Thr Glu Asp Glu Val Arg Glu Leu Glu Ser
                245                 250                 255

ctt gag act ctg ctt ttg caa gcg gca aca cag tct gtg ata aca agt      816
Leu Glu Thr Leu Leu Leu Gln Ala Ala Thr Gln Ser Val Ile Thr Ser
            260                 265                 270

act ggg gag aga aag aat ctg agt cat atg atg agt cag agg ctt aag      864
Thr Gly Glu Arg Lys Asn Leu Ser His Met Met Ser Gln Arg Leu Lys
        275                 280                 285

cct acg ttt aac cgc aac ccg ttg aag cga tgg tac cgt ggt ctt aga      912
Pro Thr Phe Asn Arg Asn Pro Leu Lys Arg Trp Tyr Arg Gly Leu Arg
    290                 295                 300

ttc ttc ttg tta gac aac tgg caa aga tgt tgg gtt ata gtg cta tgg      960
Phe Phe Leu Leu Asp Asn Trp Gln Arg Cys Trp Val Ile Val Leu Trp
305                 310                 315                 320

ttc ata gtt atg gct ata ctc ttc acc tac aaa tat atc caa tac agg     1008
Phe Ile Val Met Ala Ile Leu Phe Thr Tyr Lys Tyr Ile Gln Tyr Arg
                325                 330                 335

cgt agc cct gtg tat cca gtg atg ggt gat tgt gtg tgc atg gct aaa     1056
Arg Ser Pro Val Tyr Pro Val Met Gly Asp Cys Val Cys Met Ala Lys
            340                 345                 350

ggt gct gca gaa aca gtg aag ctg aac atg gct ttg att ctc tta cct     1104
Gly Ala Ala Glu Thr Val Lys Leu Asn Met Ala Leu Ile Leu Leu Pro
        355                 360                 365

gtt tgt aga aac acc atc aca tgg ctt aga aat aag acc agg ttg ggt     1152
Val Cys Arg Asn Thr Ile Thr Trp Leu Arg Asn Lys Thr Arg Leu Gly
    370                 375                 380

cgt gtt gtc cca ttt gat gac aat ctc aac ttc cac aag gtt ata gcg     1200
Arg Val Val Pro Phe Asp Asp Asn Leu Asn Phe His Lys Val Ile Ala
385                 390                 395                 400

gtg ggg att ata gtt gga gta acg atg cac gcc ggg gca cat tta gcg     1248
Val Gly Ile Ile Val Gly Val Thr Met His Ala Gly Ala His Leu Ala
```

```
                405                 410                 415

tgt gat ttc ccg cgg tta cta cat gca act cca gag gca tat agg cct      1296
Cys Asp Phe Pro Arg Leu Leu His Ala Thr Pro Glu Ala Tyr Arg Pro
            420                 425                 430

tta aga cag ttt ttt ggg gat gag caa cca aag agc tac tgg cat ttt      1344
Leu Arg Gln Phe Phe Gly Asp Glu Gln Pro Lys Ser Tyr Trp His Phe
        435                 440                 445

gta aac tcg gta gaa ggt ata acc gga ctt gtg atg gtt ttg tta atg      1392
Val Asn Ser Val Glu Gly Ile Thr Gly Leu Val Met Val Leu Leu Met
    450                 455                 460

gcg att gca ttc aca cta gcc acg cct tgg ttc aga aga ggg aag cta      1440
Ala Ile Ala Phe Thr Leu Ala Thr Pro Trp Phe Arg Arg Gly Lys Leu
465                 470                 475                 480

aac tat ctt cca gga cca tta aag aaa cta gct agc ttc aat gcc ttc      1488
Asn Tyr Leu Pro Gly Pro Leu Lys Lys Leu Ala Ser Phe Asn Ala Phe
                485                 490                 495

tgg tac act cat cat ttg ttt gtc ata gtc tac att ctt ctt gtt gct      1536
Trp Tyr Thr His His Leu Phe Val Ile Val Tyr Ile Leu Leu Val Ala
            500                 505                 510

cat gga tac tac ttg tat ctc acc aga gac tgg cac aat aaa acg act      1584
His Gly Tyr Tyr Leu Tyr Leu Thr Arg Asp Trp His Asn Lys Thr Thr
        515                 520                 525

tgg atg tat ttg gtg gta cca gtg gtt cta tac gcg tgt gaa agg ttg      1632
Trp Met Tyr Leu Val Val Pro Val Val Leu Tyr Ala Cys Glu Arg Leu
    530                 535                 540

ata aga gca ttc agg tcg agc atc aag gcg gtg act att agg aaa gta      1680
Ile Arg Ala Phe Arg Ser Ser Ile Lys Ala Val Thr Ile Arg Lys Val
545                 550                 555                 560

gca gtt tat cca gga aac gtg ctg gca att cac ttg tca agg cct caa      1728
Ala Val Tyr Pro Gly Asn Val Leu Ala Ile His Leu Ser Arg Pro Gln
                565                 570                 575

aac ttc aaa tac aag agt ggt caa tac atg ttt gtt aac tgt gct gct      1776
Asn Phe Lys Tyr Lys Ser Gly Gln Tyr Met Phe Val Asn Cys Ala Ala
            580                 585                 590

gtt tct cca ttt gaa tgg cat cca ttt tca atc aca tct gca cca caa      1824
Val Ser Pro Phe Glu Trp His Pro Phe Ser Ile Thr Ser Ala Pro Gln
        595                 600                 605

gat gat tac cta agt gtt cac att aga gtt ctt ggg gat tgg aca cga      1872
Asp Asp Tyr Leu Ser Val His Ile Arg Val Leu Gly Asp Trp Thr Arg
    610                 615                 620

gct ctc aaa gga gtc ttc tct gag gtg tgt aag cca cca ccg gca gga      1920
Ala Leu Lys Gly Val Phe Ser Glu Val Cys Lys Pro Pro Pro Ala Gly
625                 630                 635                 640

gtt agt ggt ctg ctt aga gcc gac atg ttg cat ggt gca aat aat ccc      1968
Val Ser Gly Leu Leu Arg Ala Asp Met Leu His Gly Ala Asn Asn Pro
                645                 650                 655

gac ttc ccg aaa gtc ttg att gat ggt cca tat ggt gca cca gca caa      2016
Asp Phe Pro Lys Val Leu Ile Asp Gly Pro Tyr Gly Ala Pro Ala Gln
            660                 665                 670

gac tac aag aag tac gag gtg gtt cta cta gtt ggt ctc ggg att gga      2064
Asp Tyr Lys Lys Tyr Glu Val Val Leu Leu Val Gly Leu Gly Ile Gly
        675                 680                 685

gcc aca cca atg atc agt atc gtc aaa gac att gtt aat aac atc aag      2112
Ala Thr Pro Met Ile Ser Ile Val Lys Asp Ile Val Asn Asn Ile Lys
    690                 695                 700

gcc aag gaa caa gcc caa cta aac cga atg gag aat gga aca agc gaa      2160
Ala Lys Glu Gln Ala Gln Leu Asn Arg Met Glu Asn Gly Thr Ser Glu
705                 710                 715                 720

cca caa cga agt aag aaa gag agt ttc agg acc cgt aga gct tac ttc      2208
Pro Gln Arg Ser Lys Lys Glu Ser Phe Arg Thr Arg Arg Ala Tyr Phe
```

```
                725                 730                 735

tat tgg gtt acg cgt gag caa ggc tct ttc gat tgg ttc aag aac ata     2256
Tyr Trp Val Thr Arg Glu Gln Gly Ser Phe Asp Trp Phe Lys Asn Ile
            740                 745                 750

atg aac gaa gtc gcg gaa cga gat gcc aac cgc gtc atc gaa atg cat     2304
Met Asn Glu Val Ala Glu Arg Asp Ala Asn Arg Val Ile Glu Met His
        755                 760                 765

aac tat tgt aca agt gtc tat gaa gaa ggt gac gct cgt tcc gca ctt     2352
Asn Tyr Cys Thr Ser Val Tyr Glu Glu Gly Asp Ala Arg Ser Ala Leu
    770                 775                 780

ata cat atg ctt caa tca cta aac cat gca aag aac ggc gtc gac att     2400
Ile His Met Leu Gln Ser Leu Asn His Ala Lys Asn Gly Val Asp Ile
785                 790                 795                 800

gtc tct gga aca aga gtt atg tcc cat ttc gct aaa cct aat tgg aga     2448
Val Ser Gly Thr Arg Val Met Ser His Phe Ala Lys Pro Asn Trp Arg
                805                 810                 815

aat gtt tac aag cgt ata gct atg gat cat cct aac acc aaa gtt gga     2496
Asn Val Tyr Lys Arg Ile Ala Met Asp His Pro Asn Thr Lys Val Gly
            820                 825                 830

gtg ttt tac tgt gga gca cca gca ttg aca aag gag cta agg cat cta     2544
Val Phe Tyr Cys Gly Ala Pro Ala Leu Thr Lys Glu Leu Arg His Leu
        835                 840                 845

gct tta gat ttc acc cac aaa aca agc acc aga ttc tcc ttc cac aaa     2592
Ala Leu Asp Phe Thr His Lys Thr Ser Thr Arg Phe Ser Phe His Lys
    850                 855                 860

gag aat ttc taa                                                     2604
Glu Asn Phe
865


<210> SEQ ID NO 20
<211> LENGTH: 867
<212> TYPE: PRT
<213> ORGANISM: Arabidopsis thaliana

<400> SEQUENCE: 20

Met Ser Arg Val Ser Phe Glu Val Ser Gly Gly Tyr His Ser Asp Ala
  1               5                  10                  15

Glu Ala Gly Asn Ser Gly Pro Met Ser Gly Gly Gln Leu Pro Pro Ile
             20                  25                  30

Tyr Lys Lys Pro Gly Asn Ser Arg Phe Thr Ala Glu Asn Ser Gln Arg
         35                  40                  45

Thr Arg Thr Ala Pro Tyr Val Asp Leu Thr Val Asp Val Gln Asp Asp
     50                  55                  60

Thr Val Ser Val His Ser Leu Lys Met Glu Gly Gly Ser Ser Val Glu
 65                  70                  75                  80

Glu Ser Pro Glu Leu Thr Leu Leu Lys Arg Asn Arg Leu Glu Lys Lys
                 85                  90                  95

Thr Thr Val Val Lys Arg Leu Ala Ser Val Ser His Glu Leu Lys Arg
            100                 105                 110

Leu Thr Ser Val Ser Gly Gly Ile Gly Gly Arg Lys Pro Pro Arg Pro
        115                 120                 125

Ala Lys Leu Asp Arg Thr Lys Ser Ala Ala Ser Gln Ala Leu Lys Gly
    130                 135                 140

Leu Lys Phe Ile Ser Lys Thr Asp Gly Gly Ala Gly Trp Ser Ala Val
145                 150                 155                 160

Glu Lys Arg Phe Asn Gln Ile Thr Ala Thr Thr Gly Gly Leu Leu Leu
                165                 170                 175

Arg Thr Lys Phe Gly Glu Cys Ile Gly Met Thr Ser Lys Asp Phe Ala
```

```
            180                 185                 190

Leu Glu Leu Phe Asp Ala Leu Ala Arg Arg Arg Asn Ile Thr Gly Glu
        195                 200                 205

Val Ile Asp Gly Asp Gln Leu Lys Glu Phe Trp Glu Gln Ile Asn Asp
    210                 215                 220

Gln Ser Phe Asp Ser Arg Leu Lys Thr Phe Phe Asp Met Val Asp Lys
225                 230                 235                 240

Asp Ala Asp Gly Arg Leu Thr Glu Asp Glu Val Arg Glu Leu Glu Ser
                245                 250                 255

Leu Glu Thr Leu Leu Leu Gln Ala Ala Thr Gln Ser Val Ile Thr Ser
            260                 265                 270

Thr Gly Glu Arg Lys Asn Leu Ser His Met Met Ser Gln Arg Leu Lys
        275                 280                 285

Pro Thr Phe Asn Arg Asn Pro Leu Lys Arg Trp Tyr Arg Gly Leu Arg
    290                 295                 300

Phe Phe Leu Leu Asp Asn Trp Gln Arg Cys Trp Val Ile Val Leu Trp
305                 310                 315                 320

Phe Ile Val Met Ala Ile Leu Phe Thr Tyr Lys Tyr Ile Gln Tyr Arg
                325                 330                 335

Arg Ser Pro Val Tyr Pro Val Met Gly Asp Cys Val Cys Met Ala Lys
            340                 345                 350

Gly Ala Ala Glu Thr Val Lys Leu Asn Met Ala Leu Ile Leu Leu Pro
        355                 360                 365

Val Cys Arg Asn Thr Ile Thr Trp Leu Arg Asn Lys Thr Arg Leu Gly
    370                 375                 380

Arg Val Val Pro Phe Asp Asp Asn Leu Asn Phe His Lys Val Ile Ala
385                 390                 395                 400

Val Gly Ile Ile Val Gly Val Thr Met His Ala Gly Ala His Leu Ala
                405                 410                 415

Cys Asp Phe Pro Arg Leu Leu His Ala Thr Pro Glu Ala Tyr Arg Pro
            420                 425                 430

Leu Arg Gln Phe Phe Gly Asp Glu Gln Pro Lys Ser Tyr Trp His Phe
        435                 440                 445

Val Asn Ser Val Glu Gly Ile Thr Gly Leu Val Met Val Leu Leu Met
    450                 455                 460

Ala Ile Ala Phe Thr Leu Ala Thr Pro Trp Phe Arg Arg Gly Lys Leu
465                 470                 475                 480

Asn Tyr Leu Pro Gly Pro Leu Lys Lys Leu Ala Ser Phe Asn Ala Phe
                485                 490                 495

Trp Tyr Thr His His Leu Phe Val Ile Val Tyr Ile Leu Leu Val Ala
            500                 505                 510

His Gly Tyr Tyr Leu Tyr Leu Thr Arg Asp Trp His Asn Lys Thr Thr
        515                 520                 525

Trp Met Tyr Leu Val Val Pro Val Val Leu Tyr Ala Cys Glu Arg Leu
    530                 535                 540

Ile Arg Ala Phe Arg Ser Ser Ile Lys Ala Val Thr Ile Arg Lys Val
545                 550                 555                 560

Ala Val Tyr Pro Gly Asn Val Leu Ala Ile His Leu Ser Arg Pro Gln
                565                 570                 575

Asn Phe Lys Tyr Lys Ser Gly Gln Tyr Met Phe Val Asn Cys Ala Ala
            580                 585                 590

Val Ser Pro Phe Glu Trp His Pro Phe Ser Ile Thr Ser Ala Pro Gln
        595                 600                 605
```

```
Asp Asp Tyr Leu Ser Val His Ile Arg Val Leu Gly Asp Trp Thr Arg
    610                 615                 620

Ala Leu Lys Gly Val Phe Ser Glu Val Cys Lys Pro Pro Pro Ala Gly
625                 630                 635                 640

Val Ser Gly Leu Leu Arg Ala Asp Met Leu His Gly Ala Asn Asn Pro
                645                 650                 655

Asp Phe Pro Lys Val Leu Ile Asp Gly Pro Tyr Gly Ala Pro Ala Gln
            660                 665                 670

Asp Tyr Lys Lys Tyr Glu Val Val Leu Leu Val Gly Leu Gly Ile Gly
        675                 680                 685

Ala Thr Pro Met Ile Ser Ile Val Lys Asp Ile Val Asn Asn Ile Lys
    690                 695                 700

Ala Lys Glu Gln Ala Gln Leu Asn Arg Met Glu Asn Gly Thr Ser Glu
705                 710                 715                 720

Pro Gln Arg Ser Lys Lys Glu Ser Phe Arg Thr Arg Arg Ala Tyr Phe
                725                 730                 735

Tyr Trp Val Thr Arg Glu Gln Gly Ser Phe Asp Trp Phe Lys Asn Ile
            740                 745                 750

Met Asn Glu Val Ala Glu Arg Asp Ala Asn Arg Val Ile Glu Met His
        755                 760                 765

Asn Tyr Cys Thr Ser Val Tyr Glu Glu Gly Asp Ala Arg Ser Ala Leu
    770                 775                 780

Ile His Met Leu Gln Ser Leu Asn His Ala Lys Asn Gly Val Asp Ile
785                 790                 795                 800

Val Ser Gly Thr Arg Val Met Ser His Phe Ala Lys Pro Asn Trp Arg
                805                 810                 815

Asn Val Tyr Lys Arg Ile Ala Met Asp His Pro Asn Thr Lys Val Gly
            820                 825                 830

Val Phe Tyr Cys Gly Ala Pro Ala Leu Thr Lys Glu Leu Arg His Leu
        835                 840                 845

Ala Leu Asp Phe Thr His Lys Thr Ser Thr Arg Phe Ser Phe His Lys
    850                 855                 860

Glu Asn Phe
865


<210> SEQ ID NO 21
<211> LENGTH: 2709
<212> TYPE: DNA
<213> ORGANISM: Arabidopsis thaliana
<220> FEATURE:
<221> NAME/KEY: CDS
<222> LOCATION: (1)..(2706)
<223> OTHER INFORMATION: coding for NADPH oxidase

<400> SEQUENCE: 21

atg atg aat cga agt gaa atg caa aag tta ggt ttc gaa cac gtg aga       48
Met Met Asn Arg Ser Glu Met Gln Lys Leu Gly Phe Glu His Val Arg
  1               5                  10                  15

tac tac aca gag tcg ccg tac aac aga gga gag tcc tcg gcg aac gtg       96
Tyr Tyr Thr Glu Ser Pro Tyr Asn Arg Gly Glu Ser Ser Ala Asn Val
            20                  25                  30

gcg acg aca agc aac tat tac ggt gaa gat gaa cca tac gtg gag atc      144
Ala Thr Thr Ser Asn Tyr Tyr Gly Glu Asp Glu Pro Tyr Val Glu Ile
        35                  40                  45

acg cta gat atc cac gac gat tcc gtc tcc gtg tac ggc ttg aag tca      192
Thr Leu Asp Ile His Asp Asp Ser Val Ser Val Tyr Gly Leu Lys Ser
     50                  55                  60

ccg aac cat cga ggg gcc ggg tct aat tat gag gat caa tcg ctt ctc      240
```

```
Pro Asn His Arg Gly Ala Gly Ser Asn Tyr Glu Asp Gln Ser Leu Leu
 65                  70                  75                  80

aga caa ggt cgt tca ggg agg agt aac tcg gta ttg aaa cgc ttg gct      288
Arg Gln Gly Arg Ser Gly Arg Ser Asn Ser Val Leu Lys Arg Leu Ala
                 85                  90                  95

tct tct gtt tcc acc gga ata aca cga gtt gct tct tct gtt tct tcg      336
Ser Ser Val Ser Thr Gly Ile Thr Arg Val Ala Ser Ser Val Ser Ser
            100                 105                 110

tct tcc gcg aga aaa cca ccg cgg ccg cag ctg gct aag ctg cgc cgt      384
Ser Ser Ala Arg Lys Pro Pro Arg Pro Gln Leu Ala Lys Leu Arg Arg
        115                 120                 125

tcg aaa tct aga gca gag cta gct ctc aaa ggt ctt aaa ttc atc acc      432
Ser Lys Ser Arg Ala Glu Leu Ala Leu Lys Gly Leu Lys Phe Ile Thr
    130                 135                 140

aag act gat ggt gtc act ggt tgg cct gaa gtt gag aaa cgg ttt tat      480
Lys Thr Asp Gly Val Thr Gly Trp Pro Glu Val Glu Lys Arg Phe Tyr
145                 150                 155                 160

gtg atg aca atg act aat aac gga tta tta cac cga tcc aga ttc ggt      528
Val Met Thr Met Thr Asn Asn Gly Leu Leu His Arg Ser Arg Phe Gly
                165                 170                 175

gaa tgt ata ggg atg aaa tcg acg gag ttt gcg ttg gca ttg ttc gat      576
Glu Cys Ile Gly Met Lys Ser Thr Glu Phe Ala Leu Ala Leu Phe Asp
            180                 185                 190

gct tta gcg agg agg gaa aac gta agc gga gat tca ata aac atg aat      624
Ala Leu Ala Arg Arg Glu Asn Val Ser Gly Asp Ser Ile Asn Met Asn
        195                 200                 205

gag ctt aaa gag ttc tgg aag cag atc act gat caa gat ttt gat tca      672
Glu Leu Lys Glu Phe Trp Lys Gln Ile Thr Asp Gln Asp Phe Asp Ser
    210                 215                 220

agg cta cga act ttc ttc gcc atg gtc gat aag gat tcg gat ggg cgg      720
Arg Leu Arg Thr Phe Phe Ala Met Val Asp Lys Asp Ser Asp Gly Arg
225                 230                 235                 240

ttg aat gaa gcc gaa gta aga gag att ata act tta agt gct tct gca      768
Leu Asn Glu Ala Glu Val Arg Glu Ile Ile Thr Leu Ser Ala Ser Ala
                245                 250                 255

aac gag ttg gat aac att cgg aga caa gct gat gaa tat gct gct ttg      816
Asn Glu Leu Asp Asn Ile Arg Arg Gln Ala Asp Glu Tyr Ala Ala Leu
            260                 265                 270

att atg gaa gaa ctc gat cct tat cat tat gga tac atc atg ata gag      864
Ile Met Glu Glu Leu Asp Pro Tyr His Tyr Gly Tyr Ile Met Ile Glu
        275                 280                 285

aat ctc gag ata ctt cta ttg caa gcg ccg atg cag gat gtg aga gat      912
Asn Leu Glu Ile Leu Leu Leu Gln Ala Pro Met Gln Asp Val Arg Asp
    290                 295                 300

gga gag agt aag aag cta agc aag atg cta agt cag aat ctc atg gtt      960
Gly Glu Ser Lys Lys Leu Ser Lys Met Leu Ser Gln Asn Leu Met Val
305                 310                 315                 320

ccg cag agt agg aat ctc ggg gca cgt ttt tgc aga ggg atg aag tat     1008
Pro Gln Ser Arg Asn Leu Gly Ala Arg Phe Cys Arg Gly Met Lys Tyr
                325                 330                 335

ttt ttg ttt gat aat tgg aag aga gtg tgg gtg atg gct cta tgg ata     1056
Phe Leu Phe Asp Asn Trp Lys Arg Val Trp Val Met Ala Leu Trp Ile
            340                 345                 350

ggt gct atg gcg ggt ttg ttc acg tgg aag ttt atg gag tat cga aaa     1104
Gly Ala Met Ala Gly Leu Phe Thr Trp Lys Phe Met Glu Tyr Arg Lys
        355                 360                 365

aga tcc gct tac gaa gtc atg gga gtt tgt gtt tgt ata gct aaa gga     1152
Arg Ser Ala Tyr Glu Val Met Gly Val Cys Val Cys Ile Ala Lys Gly
    370                 375                 380

gct gca gag acg ctt aaa cta aac atg gct atg att ttg tta cca gtt     1200
```

```
Ala Ala Glu Thr Leu Lys Leu Asn Met Ala Met Ile Leu Leu Pro Val
385                 390                 395                 400

tgt agg aac acc atc act tgg ctg cgg acc aaa acc aag tta agt gct      1248
Cys Arg Asn Thr Ile Thr Trp Leu Arg Thr Lys Thr Lys Leu Ser Ala
                405                 410                 415

att gtt cct ttc gat gac agc ctc aat ttt cac aag gtc ata gct ata      1296
Ile Val Pro Phe Asp Asp Ser Leu Asn Phe His Lys Val Ile Ala Ile
            420                 425                 430

gga att tca gtt gga gtt gga atc cat gct aca tct cac tta gca tgt      1344
Gly Ile Ser Val Gly Val Gly Ile His Ala Thr Ser His Leu Ala Cys
        435                 440                 445

gat ttc ccc cga ctg ata gct gca gac gaa gat cag tat gag cca atg      1392
Asp Phe Pro Arg Leu Ile Ala Ala Asp Glu Asp Gln Tyr Glu Pro Met
    450                 455                 460

gag aag tat ttt ggg cca cag aca aag aga tat ttg gac ttt gtt caa      1440
Glu Lys Tyr Phe Gly Pro Gln Thr Lys Arg Tyr Leu Asp Phe Val Gln
465                 470                 475                 480

tcg gta gaa gga gtt acc ggg att gga atg gtt gta cta atg acc ata      1488
Ser Val Glu Gly Val Thr Gly Ile Gly Met Val Val Leu Met Thr Ile
                485                 490                 495

gcc ttt aca ttg gct aca aca tgg ttc aga cgt aat aag ctc aac ctt      1536
Ala Phe Thr Leu Ala Thr Thr Trp Phe Arg Arg Asn Lys Leu Asn Leu
            500                 505                 510

cct gga cca ctg aag aaa ata aca ggc ttc aat gcc ttc tgg tac tct      1584
Pro Gly Pro Leu Lys Lys Ile Thr Gly Phe Asn Ala Phe Trp Tyr Ser
        515                 520                 525

cac cac tta ttt gtt atc gtc tac tcg ctt ctt gtc gtt cat gga ttc      1632
His His Leu Phe Val Ile Val Tyr Ser Leu Leu Val Val His Gly Phe
    530                 535                 540

tac gta tac ctc atc atc gag cca tgg tac aag aaa acg aca tgg atg      1680
Tyr Val Tyr Leu Ile Ile Glu Pro Trp Tyr Lys Lys Thr Thr Trp Met
545                 550                 555                 560

tat ttg atg gta ccg gtg gtt ctt tac ttg tgt gaa agg ctg att cgt      1728
Tyr Leu Met Val Pro Val Val Leu Tyr Leu Cys Glu Arg Leu Ile Arg
                565                 570                 575

gca ttc agg tca agc gtc gag gct gtt tca gtg cta aag gtt gct gtg      1776
Ala Phe Arg Ser Ser Val Glu Ala Val Ser Val Leu Lys Val Ala Val
            580                 585                 590

tta cca ggg aat gtc ttg tcg ctt cac ttg tca aga cca agc aac ttc      1824
Leu Pro Gly Asn Val Leu Ser Leu His Leu Ser Arg Pro Ser Asn Phe
        595                 600                 605

aga tac aag agt gga caa tac atg tat ctc aac tgt tct gca gtt tct      1872
Arg Tyr Lys Ser Gly Gln Tyr Met Tyr Leu Asn Cys Ser Ala Val Ser
    610                 615                 620

aca tta gaa tgg cat cca ttc tca att acc tca gct cca gga gat gac      1920
Thr Leu Glu Trp His Pro Phe Ser Ile Thr Ser Ala Pro Gly Asp Asp
625                 630                 635                 640

tac ctc agt gtc cac atc agg gtt tta gga gac tgg act aag caa tta      1968
Tyr Leu Ser Val His Ile Arg Val Leu Gly Asp Trp Thr Lys Gln Leu
                645                 650                 655

aga tca tta ttc tct gag gtg tgc aag cca cgc cct cct gat gaa cac      2016
Arg Ser Leu Phe Ser Glu Val Cys Lys Pro Arg Pro Pro Asp Glu His
            660                 665                 670

aga ctg aac aga gcc gac tcg aag cac tgg gat tac atc cct gac ttt      2064
Arg Leu Asn Arg Ala Asp Ser Lys His Trp Asp Tyr Ile Pro Asp Phe
        675                 680                 685

cca aga atc cta att gat ggt cca tat gga gca cca gca caa gac tac      2112
Pro Arg Ile Leu Ile Asp Gly Pro Tyr Gly Ala Pro Ala Gln Asp Tyr
    690                 695                 700

aag aag ttt gaa gtt gtt ctg cta gtg ggt cta gga atc ggt gcc act      2160
```

```
Lys Lys Phe Glu Val Val Leu Leu Val Gly Leu Gly Ile Gly Ala Thr
705                 710                 715                 720

ccg atg atc agc ata gtg agt gac ata atc aat aac ttg aaa ggc gtg     2208
Pro Met Ile Ser Ile Val Ser Asp Ile Ile Asn Asn Leu Lys Gly Val
                725                 730                 735

gaa gaa ggc agt aac cga aga cag tca ccg atc cat aat atg gtc aca     2256
Glu Glu Gly Ser Asn Arg Arg Gln Ser Pro Ile His Asn Met Val Thr
            740                 745                 750

cct cct gtt tct cca tca aga aaa agt gag acg ttc aga acc aag aga     2304
Pro Pro Val Ser Pro Ser Arg Lys Ser Glu Thr Phe Arg Thr Lys Arg
        755                 760                 765

gct tac ttc tac tgg gtc aca aga gag cag ggg tcg ttt gac tgg ttc     2352
Ala Tyr Phe Tyr Trp Val Thr Arg Glu Gln Gly Ser Phe Asp Trp Phe
    770                 775                 780

aag aac gtg atg gac gaa gtg act gaa aca gac cgc aaa aac gta att     2400
Lys Asn Val Met Asp Glu Val Thr Glu Thr Asp Arg Lys Asn Val Ile
785                 790                 795                 800

gag ctg cat aat tac tgc acc agc gtt tac gag gaa ggg gac gcg agg     2448
Glu Leu His Asn Tyr Cys Thr Ser Val Tyr Glu Glu Gly Asp Ala Arg
                805                 810                 815

tct gca ctt atc acg atg ctc cag tct cta aac cat gct aag cat gga     2496
Ser Ala Leu Ile Thr Met Leu Gln Ser Leu Asn His Ala Lys His Gly
            820                 825                 830

gtg gac gtt gtg tca gga aca cgt gtc atg tcc cat ttc gct agg cca     2544
Val Asp Val Val Ser Gly Thr Arg Val Met Ser His Phe Ala Arg Pro
        835                 840                 845

aac tgg aga agc gtt ttc aaa agg atc gct gtg aat cat cct aag act     2592
Asn Trp Arg Ser Val Phe Lys Arg Ile Ala Val Asn His Pro Lys Thr
    850                 855                 860

aga gtc gga gtg ttt tat tgt gga gca gct ggg tta gtg aaa gag tta     2640
Arg Val Gly Val Phe Tyr Cys Gly Ala Ala Gly Leu Val Lys Glu Leu
865                 870                 875                 880

cga cac tta tca ctg gat ttc tct cat aag acc tcc acc aag ttc atc     2688
Arg His Leu Ser Leu Asp Phe Ser His Lys Thr Ser Thr Lys Phe Ile
                885                 890                 895

ttc cat aaa gag aat ttc taa                                         2709
Phe His Lys Glu Asn Phe
            900


<210> SEQ ID NO 22
<211> LENGTH: 902
<212> TYPE: PRT
<213> ORGANISM: Arabidopsis thaliana

<400> SEQUENCE: 22

Met Met Asn Arg Ser Glu Met Gln Lys Leu Gly Phe Glu His Val Arg
  1               5                  10                  15

Tyr Tyr Thr Glu Ser Pro Tyr Asn Arg Gly Glu Ser Ser Ala Asn Val
             20                  25                  30

Ala Thr Thr Ser Asn Tyr Tyr Gly Glu Asp Glu Pro Tyr Val Glu Ile
         35                  40                  45

Thr Leu Asp Ile His Asp Asp Ser Val Ser Val Tyr Gly Leu Lys Ser
     50                  55                  60

Pro Asn His Arg Gly Ala Gly Ser Asn Tyr Glu Asp Gln Ser Leu Leu
 65                  70                  75                  80

Arg Gln Gly Arg Ser Gly Arg Ser Asn Ser Val Leu Lys Arg Leu Ala
                 85                  90                  95

Ser Ser Val Ser Thr Gly Ile Thr Arg Val Ala Ser Ser Val Ser Ser
            100                 105                 110
```

```
Ser Ser Ala Arg Lys Pro Pro Arg Pro Gln Leu Ala Lys Leu Arg Arg
        115                 120                 125

Ser Lys Ser Arg Ala Glu Leu Ala Leu Lys Gly Leu Lys Phe Ile Thr
    130                 135                 140

Lys Thr Asp Gly Val Thr Gly Trp Pro Glu Val Glu Lys Arg Phe Tyr
145                 150                 155                 160

Val Met Thr Met Thr Asn Asn Gly Leu Leu His Arg Ser Arg Phe Gly
                165                 170                 175

Glu Cys Ile Gly Met Lys Ser Thr Glu Phe Ala Leu Ala Leu Phe Asp
            180                 185                 190

Ala Leu Ala Arg Arg Glu Asn Val Ser Gly Asp Ser Ile Asn Met Asn
        195                 200                 205

Glu Leu Lys Glu Phe Trp Lys Gln Ile Thr Asp Gln Asp Phe Asp Ser
    210                 215                 220

Arg Leu Arg Thr Phe Phe Ala Met Val Asp Lys Asp Ser Asp Gly Arg
225                 230                 235                 240

Leu Asn Glu Ala Glu Val Arg Glu Ile Ile Thr Leu Ser Ala Ser Ala
                245                 250                 255

Asn Glu Leu Asp Asn Ile Arg Arg Gln Ala Asp Glu Tyr Ala Ala Leu
            260                 265                 270

Ile Met Glu Glu Leu Asp Pro Tyr His Tyr Gly Tyr Ile Met Ile Glu
        275                 280                 285

Asn Leu Glu Ile Leu Leu Leu Gln Ala Pro Met Gln Asp Val Arg Asp
    290                 295                 300

Gly Glu Ser Lys Lys Leu Ser Lys Met Leu Ser Gln Asn Leu Met Val
305                 310                 315                 320

Pro Gln Ser Arg Asn Leu Gly Ala Arg Phe Cys Arg Gly Met Lys Tyr
                325                 330                 335

Phe Leu Phe Asp Asn Trp Lys Arg Val Trp Val Met Ala Leu Trp Ile
            340                 345                 350

Gly Ala Met Ala Gly Leu Phe Thr Trp Lys Phe Met Glu Tyr Arg Lys
        355                 360                 365

Arg Ser Ala Tyr Glu Val Met Gly Val Cys Val Cys Ile Ala Lys Gly
    370                 375                 380

Ala Ala Glu Thr Leu Lys Leu Asn Met Ala Met Ile Leu Leu Pro Val
385                 390                 395                 400

Cys Arg Asn Thr Ile Thr Trp Leu Arg Thr Lys Thr Lys Leu Ser Ala
                405                 410                 415

Ile Val Pro Phe Asp Asp Ser Leu Asn Phe His Lys Val Ile Ala Ile
            420                 425                 430

Gly Ile Ser Val Gly Val Gly Ile His Ala Thr Ser His Leu Ala Cys
        435                 440                 445

Asp Phe Pro Arg Leu Ile Ala Ala Asp Glu Asp Gln Tyr Glu Pro Met
    450                 455                 460

Glu Lys Tyr Phe Gly Pro Gln Thr Lys Arg Tyr Leu Asp Phe Val Gln
465                 470                 475                 480

Ser Val Glu Gly Val Thr Gly Ile Gly Met Val Val Leu Met Thr Ile
                485                 490                 495

Ala Phe Thr Leu Ala Thr Thr Trp Phe Arg Arg Asn Lys Leu Asn Leu
            500                 505                 510

Pro Gly Pro Leu Lys Lys Ile Thr Gly Phe Asn Ala Phe Trp Tyr Ser
        515                 520                 525

His His Leu Phe Val Ile Val Tyr Ser Leu Leu Val Val His Gly Phe
    530                 535                 540
```

```
Tyr Val Tyr Leu Ile Ile Glu Pro Trp Tyr Lys Lys Thr Thr Trp Met
545                 550                 555                 560

Tyr Leu Met Val Pro Val Val Leu Tyr Leu Cys Glu Arg Leu Ile Arg
                565                 570                 575

Ala Phe Arg Ser Ser Val Glu Ala Val Ser Val Leu Lys Val Ala Val
            580                 585                 590

Leu Pro Gly Asn Val Leu Ser Leu His Leu Ser Arg Pro Ser Asn Phe
        595                 600                 605

Arg Tyr Lys Ser Gly Gln Tyr Met Tyr Leu Asn Cys Ser Ala Val Ser
    610                 615                 620

Thr Leu Glu Trp His Pro Phe Ser Ile Thr Ser Ala Pro Gly Asp Asp
625                 630                 635                 640

Tyr Leu Ser Val His Ile Arg Val Leu Gly Asp Trp Thr Lys Gln Leu
                645                 650                 655

Arg Ser Leu Phe Ser Glu Val Cys Lys Pro Arg Pro Pro Asp Glu His
            660                 665                 670

Arg Leu Asn Arg Ala Asp Ser Lys His Trp Asp Tyr Ile Pro Asp Phe
        675                 680                 685

Pro Arg Ile Leu Ile Asp Gly Pro Tyr Gly Ala Pro Ala Gln Asp Tyr
    690                 695                 700

Lys Lys Phe Glu Val Val Leu Leu Val Gly Leu Gly Ile Gly Ala Thr
705                 710                 715                 720

Pro Met Ile Ser Ile Val Ser Asp Ile Ile Asn Asn Leu Lys Gly Val
                725                 730                 735

Glu Glu Gly Ser Asn Arg Arg Gln Ser Pro Ile His Asn Met Val Thr
            740                 745                 750

Pro Pro Val Ser Pro Ser Arg Lys Ser Glu Thr Phe Arg Thr Lys Arg
        755                 760                 765

Ala Tyr Phe Tyr Trp Val Thr Arg Glu Gln Gly Ser Phe Asp Trp Phe
    770                 775                 780

Lys Asn Val Met Asp Glu Val Thr Glu Thr Asp Arg Lys Asn Val Ile
785                 790                 795                 800

Glu Leu His Asn Tyr Cys Thr Ser Val Tyr Glu Glu Gly Asp Ala Arg
                805                 810                 815

Ser Ala Leu Ile Thr Met Leu Gln Ser Leu Asn His Ala Lys His Gly
            820                 825                 830

Val Asp Val Val Ser Gly Thr Arg Val Met Ser His Phe Ala Arg Pro
        835                 840                 845

Asn Trp Arg Ser Val Phe Lys Arg Ile Ala Val Asn His Pro Lys Thr
    850                 855                 860

Arg Val Gly Val Phe Tyr Cys Gly Ala Ala Gly Leu Val Lys Glu Leu
865                 870                 875                 880

Arg His Leu Ser Leu Asp Phe Ser His Lys Thr Ser Thr Lys Phe Ile
                885                 890                 895

Phe His Lys Glu Asn Phe
            900
```

<210> SEQ ID NO 23
<211> LENGTH: 20
<212> TYPE: DNA
<213> ORGANISM: Artificial sequence
<220> FEATURE:
<223> OTHER INFORMATION: Description of the artificial sequence:
oligonucleotide primer

```
<400> SEQUENCE: 23

garcaaggct cttttgattg                                          20


<210> SEQ ID NO 24
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 24

gaaatgctcc ttatggaatt c                                        21


<210> SEQ ID NO 25
<211> LENGTH: 6
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (3)..(3)
<223> OTHER INFORMATION: Xaa is Lys or Arg
<220> FEATURE:
<221> NAME/KEY: misc_feature
<222> LOCATION: (6)..(6)
<223> OTHER INFORMATION: Xaa is Lys or Arg

<400> SEQUENCE: 25

Ala Leu Xaa Gly Leu Xaa
  1               5


<210> SEQ ID NO 26
<211> LENGTH: 10
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (3)..(3)
<223> OTHER INFORMATION: Xaa is Asn or Asp
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is Arg or Lys
<220> FEATURE:
<221> NAME/KEY: misc_feature
<222> LOCATION: (8)..(8)
<223> OTHER INFORMATION: Xaa is Ile, Leu or Val
<220> FEATURE:
<221> NAME/KEY: misc_feature
<222> LOCATION: (9)..(9)
<223> OTHER INFORMATION: Xaa is Thr or Asn

<400> SEQUENCE: 26

Asp Lys Xaa Xaa Asp Gly Xaa Xaa Xaa Glu
  1               5                  10


<210> SEQ ID NO 27
<211> LENGTH: 6
<212> TYPE: PRT
<213> ORGANISM: Unknown
<220> FEATURE:
<223> OTHER INFORMATION: motif
```

<400> SEQUENCE: 27

Leu Ser Ala Ser Ala Asn
1 5

<210> SEQ ID NO 28
<211> LENGTH: 7
<212> TYPE: PRT
<213> ORGANISM: Unknown
<220> FEATURE:
<223> OTHER INFORMATION: motif

<400> SEQUENCE: 28

Ile Met Glu Glu Leu Asp Pro
1 5

<210> SEQ ID NO 29
<211> LENGTH: 14
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa is Phe or Leu
<220> FEATURE:
<221> NAME/KEY: misc_feature
<222> LOCATION: (6)..(6)
<223> OTHER INFORMATION: Xaa is Ile or Leu
<220> FEATURE:
<221> NAME/KEY: misc_feature
<222> LOCATION: (7)..(7)
<223> OTHER INFORMATION: Xaa is Ile or Val
<220> FEATURE:
<221> NAME/KEY: misc_feature
<222> LOCATION: (9)..(9)
<223> OTHER INFORMATION: Xaa is any amino acid

<400> SEQUENCE: 29

Lys Xaa Asn Met Ala Xaa Xaa Leu Xaa Pro Val Cys Arg Asn
1 5 10

<210> SEQ ID NO 30
<211> LENGTH: 8
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (1)..(1)
<223> OTHER INFORMATION: Xaa is Glu or Gln

<400> SEQUENCE: 30

Xaa Trp His Pro Phe Ser Ile Thr
1 5

<210> SEQ ID NO 31
<211> LENGTH: 13
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa is Ala or Ser
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is Gln or Tyr
<220> FEATURE:
<221> NAME/KEY: misc_feature
<222> LOCATION: (8)..(8)
<223> OTHER INFORMATION: Xaa is Leu or Ile
<220> FEATURE:
<221> NAME/KEY: misc_feature
<222> LOCATION: (10)..(10)
<223> OTHER INFORMATION: Xaa is Ile or Val
<220> FEATURE:
<221> NAME/KEY: misc_feature
<222> LOCATION: (12)..(12)
<223> OTHER INFORMATION: Xaa is Val, Ile or Leu

<400> SEQUENCE: 31

Ser Xaa Pro Xaa Asp Asp Xaa Xaa Ser Xaa His Xaa Arg
1 5 10

<210> SEQ ID NO 32
<211> LENGTH: 11
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (6)..(6)
<223> OTHER INFORMATION: Xaa is Ser or Ala

<400> SEQUENCE: 32

Asp Gly Pro Tyr Gly Xaa Pro Ala Gly Asp Tyr
1 5 10

<210> SEQ ID NO 33
<211> LENGTH: 10
<212> TYPE: PRT
<213> ORGANISM: Unknown
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa is Ile or Val

<400> SEQUENCE: 33

Leu Xaa Gly Leu Gly Ile Gly Ala Thr Pro
1 5 10

<210> SEQ ID NO 34
<211> LENGTH: 11
<212> TYPE: PRT
<213> ORGANISM: Unknown
<220> FEATURE:
<223> OTHER INFORMATION: motif

<400> SEQUENCE: 34

Phe Tyr Trp Val Thr Arg Glu Gln Gly Ser Phe
1 5 10

<210> SEQ ID NO 35
<211> LENGTH: 6
<212> TYPE: PRT
<213> ORGANISM: Unknown
<220> FEATURE:
<223> OTHER INFORMATION: motif -continued

```
<400> SEQUENCE: 35

Gly Val Phe Tyr Cys Gly
  1             5


<210> SEQ ID NO 36
<211> LENGTH: 10
<212> TYPE: DNA
<213> ORGANISM: Unknown
<220> FEATURE:
<223> OTHER INFORMATION: promoter element

<400> SEQUENCE: 36

tcatcttctt                                                            10
```